(12) United States Patent
Yamatani et al.

(10) Patent No.: US 12,052,915 B2
(45) Date of Patent: Jul. 30, 2024

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventors: Akinori Yamatani, Yokohama (JP); Ikuo Sasaki, Yokohama (JP); Makoto Yamamoto, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 607 days.

(21) Appl. No.: 16/931,273

(22) Filed: Jul. 16, 2020

(65) Prior Publication Data

US 2021/0119138 A1     Apr. 22, 2021

(30) Foreign Application Priority Data

Oct. 16, 2019    (KR) ........................ 10-2019-0128247

(51) Int. Cl.
| | |
|---|---|
| *H10K 85/60* | (2023.01) |
| *C07D 235/06* | (2006.01) |
| *C07D 235/18* | (2006.01) |
| *C07D 235/20* | (2006.01) |
| *C07D 235/24* | (2006.01) |

(Continued)

(52) U.S. Cl.
CPC ......... *H10K 85/654* (2023.02); *C07D 235/06* (2013.01); *C07D 235/18* (2013.01); *C07D 235/20* (2013.01); *C07D 235/24* (2013.01); *C07D 235/30* (2013.01); *H10K 50/11* (2023.02);

(Continued)

(58) Field of Classification Search
CPC ............. H01L 51/0067; H01L 51/0072; H01L 51/5012; H01L 51/5048; C07D 235/06; C07D 235/18; C07D 235/20; C07D 235/24; C07D 235/30; H10K 85/654; H10K 85/6572; H10K 50/11; H10K 50/14

See application file for complete search history.

(56) References Cited

U.S. PATENT DOCUMENTS

| | | |
|---|---|---|
| 6,780,529 B2 | 8/2004 | Kimura |
| 8,119,814 B2 | 2/2012 | Shin et al. |

(Continued)

FOREIGN PATENT DOCUMENTS

| | | |
|---|---|---|
| CN | 103952009 A | 7/2014 |
| CN | 106967052 A | 7/2017 |

(Continued)

*Primary Examiner* — Aaron J Gray
(74) *Attorney, Agent, or Firm* — Lewis Roca Rothgerber Christie LLP

(57) ABSTRACT

An organic electroluminescence device according to an embodiment of the present disclosure includes a first electrode, a second electrode facing the first electrode, and a plurality of organic layers between the first electrode and the second electrode, wherein at least one organic layer of the plurality of organic layers includes a polycyclic compound containing two aromatic 6-membered rings which are linked by a single bond, and a plurality of benzimidazole groups which are substituted at the two aromatic 6-membered rings, wherein each of the two aromatic 6-membered rings includes a carbon atom or a nitrogen atom as an atom for forming a ring.

20 Claims, 2 Drawing Sheets

(51) Int. Cl.
*C07D 235/30* (2006.01)
*H10K 50/11* (2023.01)
*H10K 50/14* (2023.01)
*H10K 85/40* (2023.01)

(52) U.S. Cl.
CPC ......... *H10K 50/14* (2023.02); *H10K 85/6572* (2023.02); *H10K 85/40* (2023.02)

(56) References Cited

U.S. PATENT DOCUMENTS

| | | |
|---|---|---|
| 9,265,767 B2 | 2/2016 | Chesworth et al. |
| 10,497,878 B2 | 12/2019 | Yasuda et al. |
| 2005/0101772 A1 | 5/2005 | Schottek et al. |
| 2011/0114888 A1* | 5/2011 | Akino ................ C09K 11/06 |
| | | 252/301.16 |
| 2011/0224204 A1 | 9/2011 | Chesworth et al. |
| 2011/0257235 A1 | 10/2011 | Crandall et al. |
| 2015/0255730 A1* | 9/2015 | Chuang .............. C07D 235/20 |
| | | 548/266.2 |
| 2016/0254461 A1* | 9/2016 | Inoue ................ C07F 15/0033 |
| | | 257/40 |
| 2018/0162843 A1* | 6/2018 | Parham ............ H10K 85/6572 |
| 2019/0165282 A1 | 5/2019 | Parham et al. |
| 2020/0055822 A1 | 2/2020 | Wirges et al. |

FOREIGN PATENT DOCUMENTS

| | | |
|---|---|---|
| CN | 107021926 A | 8/2017 |
| CN | 107056783 A | 8/2017 |
| CN | 107417668 A | 12/2017 |
| EP | 3 070 144 A1 | 9/2016 |
| JP | 2002-338579 A | 11/2002 |
| JP | 2006-100394 A | 4/2006 |
| KR | 10-1528241 B1 | 6/2015 |
| KR | 10-1628438 B1 | 6/2016 |
| KR | 10-2017-0058619 A | 5/2017 |
| KR | 10-1806464 B1 | 12/2017 |
| WO | WO 00/001676 A1 | 1/2000 |
| WO | WO 02/066486 A1 | 8/2002 |
| WO | WO 2009/157429 A1 | 12/2009 |
| WO | WO 2009/158467 A1 | 12/2009 |
| WO | WO 2009/158473 A1 | 12/2009 |
| WO | WO 2010/025558 A1 | 3/2010 |
| WO | WO 2017/082246 A1 | 5/2017 |
| WO | WO 2017/150930 A1 | 9/2017 |
| WO | WO 2017/178311 A1 | 10/2017 |
| WO | WO 2018/033610 A1 | 2/2018 |
| WO | WO 2018/157981 A1 | 9/2018 |

* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATIONS

This application claims priority to and the benefit of Korean Patent Application No. 10-2019-0128247, filed on Oct. 16, 2019, the entire contents of which are incorporated herein by reference.

BACKGROUND

1. Field

Embodiments the present disclosure herein relate to an organic electroluminescence device and a polycyclic compound used therein.

2. Description of the Related Art

Recently, the development of an organic electroluminescence display as an image display is being actively conducted. The organic electroluminescence display is referred to as a self-luminescent display in which holes and electrons injected from a first electrode and a second electrode recombine in an emission layer to generate an exciton, and the generated exciton returns (e.g., transitions) to a ground state and emits light to attain display.

In the application of an organic electroluminescence device to a display, a low driving voltage, high luminous efficiency, and long service life of the organic electroluminescence device are beneficial, and development of a thermally activated delayed fluorescence (TADF) material which is capable of stably attaining these requirements is being continuously studied.

SUMMARY

Embodiments of the present disclosure herein provide an organic electroluminescence device exhibiting high efficiency and long service life.

Embodiments of the present disclosure herein also provide a polycyclic compound applied in the organic electroluminescence device to achieve high efficiency and long service life.

An embodiment of the present disclosure provides an organic electroluminescence device including a first electrode, a second electrode facing the first electrode, and a plurality of organic layers between the first electrode and the second electrode, wherein at least one organic layer of the plurality of organic layers includes a polycyclic compound containing two aromatic 6-membered rings which are linked by a single bond, and a plurality of benzimidazole groups which are substituted at the two aromatic 6-membered rings, wherein each of the two aromatic 6-membered rings includes a carbon atom or a nitrogen atom as an atom for forming a ring, wherein the first electrode and the second electrode each independently include at least one selected from Ag, Mg, Cu, Al, Pt, Pd, Au, Ni, Nd, Ir, Cr, Li, Ca, LiF/Ca, LiF/Al, Mo, Ti, In, Sn, Zn, a compound of two or more thereof, a mixture of two or more thereof, and oxides thereof.

In an embodiment, at least one of the plurality of benzimidazole groups may be substituted at the ortho-position of any one between the two aromatic 6-membered rings with respect to the single bond.

In an embodiment, the number of the plurality of benzimidazole groups may be 2 to 4.

In an embodiment, each of the plurality of benzimidazole groups may be substituted at the ortho-position or the meta-position of a respective one of the two aromatic 6-membered rings with respect to the single bond.

In an embodiment, the lowest triplet excitation energy level (T1 level) of the polycyclic compound may be 2.8 eV or more.

In an embodiment, the plurality of organic layers may include a hole transport region, an emission layer, and an electron transport region, wherein the emission layer may include the polycyclic compound.

In an embodiment, the emission layer may have phosphorescence luminescence or thermally activated delayed fluorescence luminescence characteristics.

In an embodiment, the maximum luminous wavelength of the emission layer may be 440 nm to 500 nm.

In an embodiment, the plurality of organic layers may include a hole transport region, an emission layer, and an electron transport region, and the electron transport region may include the polycyclic compound.

In an embodiment, the polycyclic compound represented by Formula 1 below:

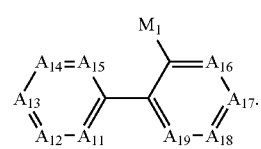

[Formula 1]

In Formula 1 above, $A_{11}$ to $A_{19}$ may be each independently N or CR, R may be a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 6 to 30 carbon atoms for forming a ring, or $M_2$, or may be combined with an adjacent group to form a ring. At least one selected from among $A_{11}$ to $A_{15}$ may be $CM_2$.

$M_1$ and $M_2$ may be each independently represented by Formula 2 below:

[Formula 2]

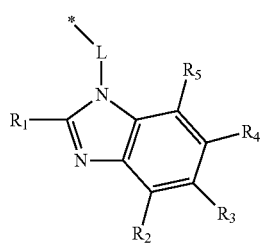

In Formula 2 above, $R_1$ to $R_5$ may be each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring, and L may be a direct linkage, a substituted or unsubstituted arylene group having 6 to 30 carbon atoms for forming a ring, or a substituted or unsubstituted heteroarylene group having 2 to 30 carbon atoms.

In an embodiment, the polycyclic compound represented by Formula 1 above may be represented by any one selected from among Formula 1-1 to Formula 1-7 below:

[Formula 1-1]

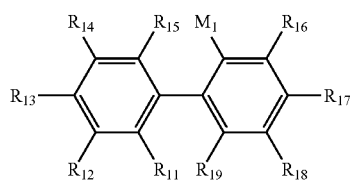

[Formula 1-2]

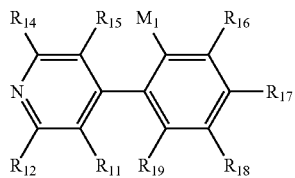

[Formula 1-3]

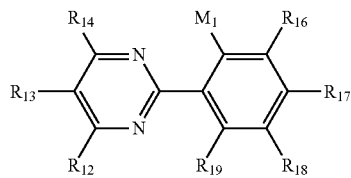

[Formula 1-4]

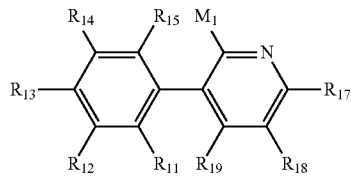

[Formula 1-5]

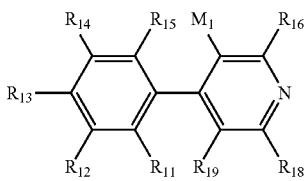

[Formula 1-6]

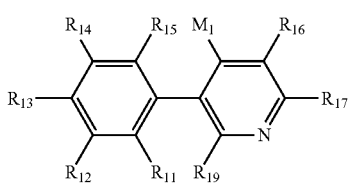

[Formula 1-7]

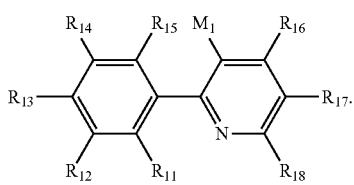

In Formula 1-1 to Formula 1-7 above, $R_{11}$ to $R_{19}$ may be each independently a hydrogen atom, or represented by Formula 2. At least one selected from among $R_{11}$ to $R_{19}$ may be represented by Formula 2.

$M_1$ may be the same as that defined with respect to Formula 1.

In an embodiment, the substituent represented by Formula 2 above may be represented by any one selected from among Formula 2-1 to Formula 2-4 below:

[Formula 2-1]

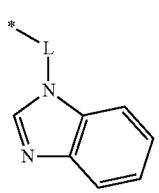

[Formula 2-2]

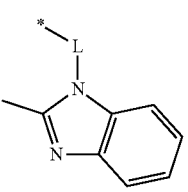

[Formula 2-3]

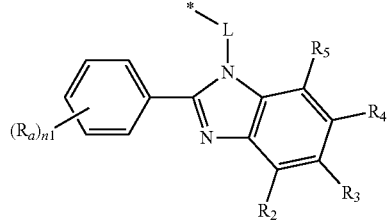

[Formula 2-4]

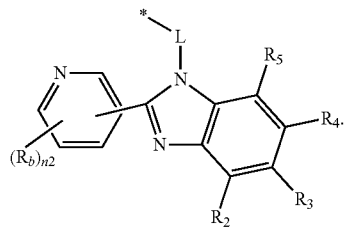

In Formula 2-1 to Formula 2-4 above, $R_a$ and $R_b$ may be each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or may be combined with an adjacent group to form a ring.

$n_1$ and $n_2$ may be each independently an integer of 0 to 4.

$R_2$ to $R_5$ and L may be the same as those defined with respect to Formula 2.

In an embodiment, one to three selected from among $A_{11}$ to $A_{19}$ above may be $CM_2$.

In an embodiment, the polycyclic compound represented by Formula 1 above may be any one selected from among compounds represented by Compound Group 1 below:

[Compound Group 1]

1

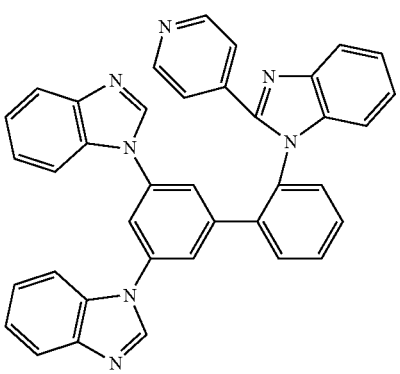

2

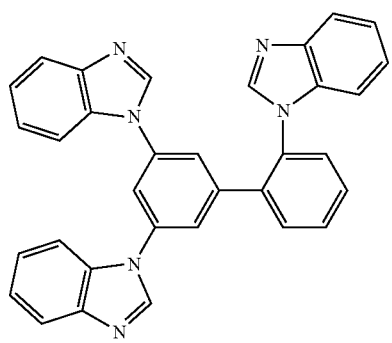

3

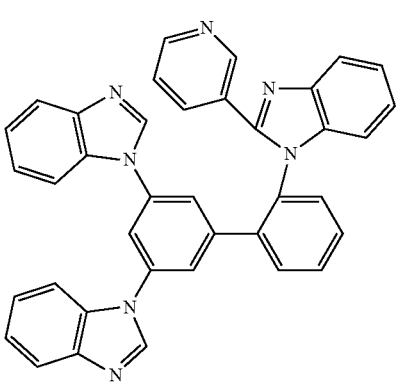

4

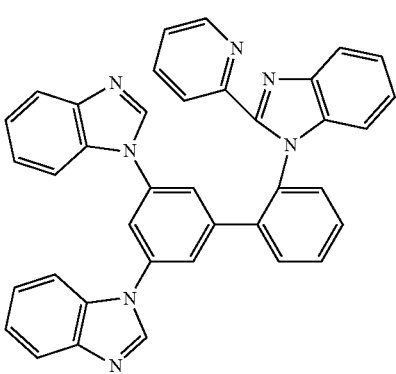

5

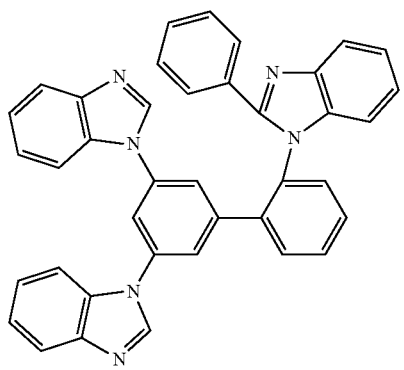

6

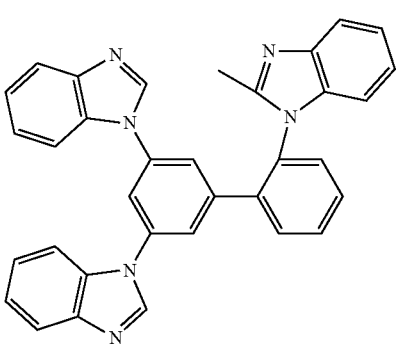

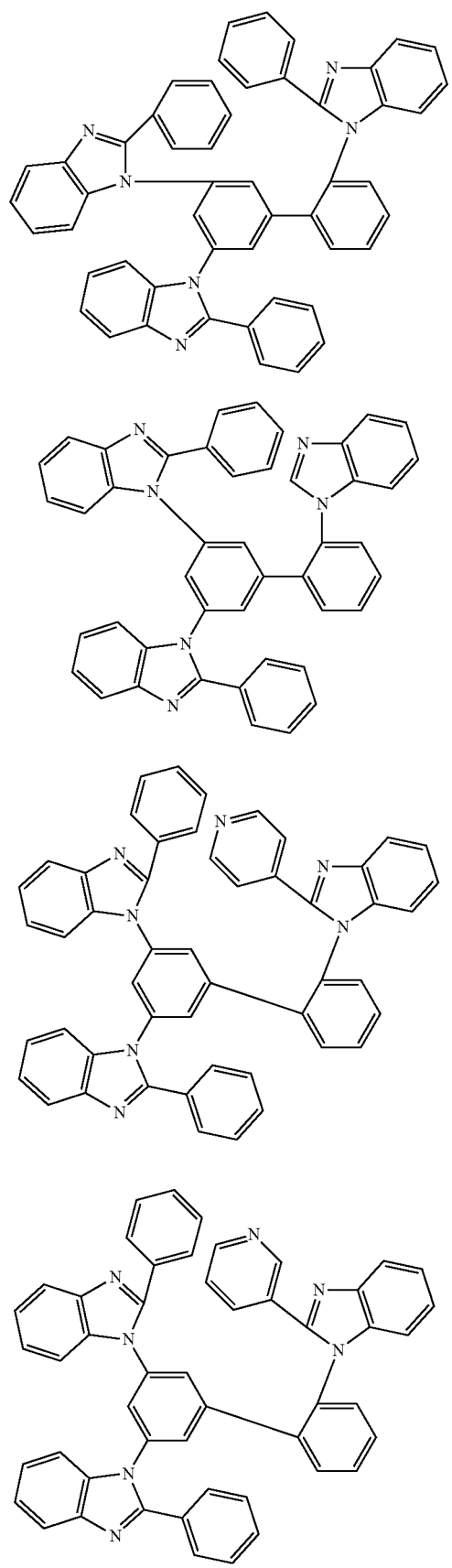
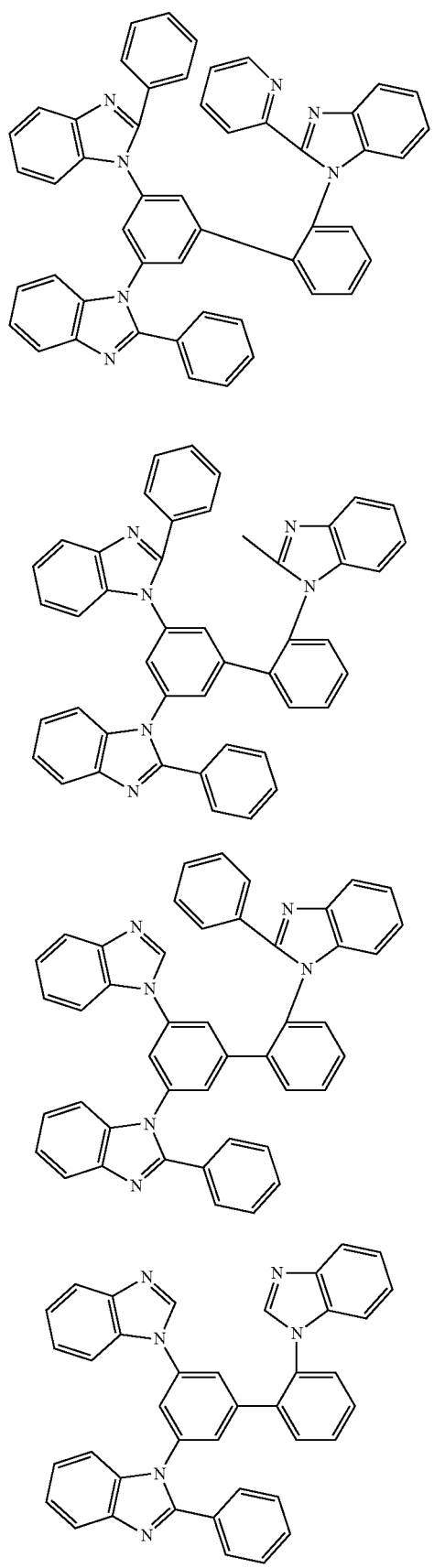

15
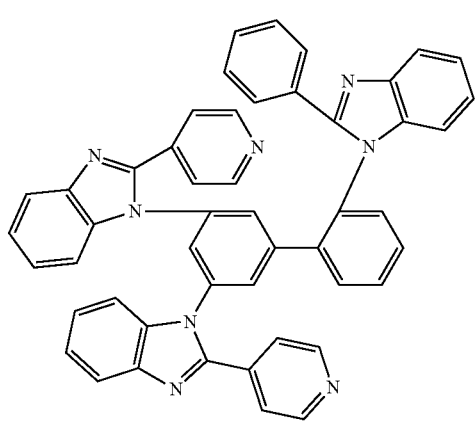
16
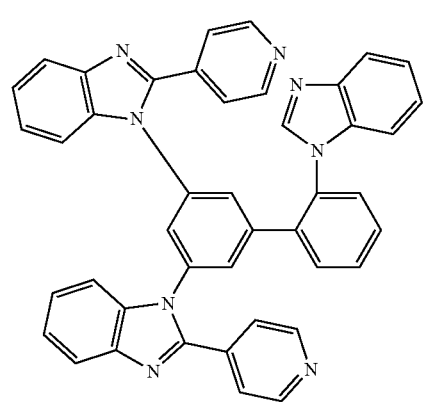
17
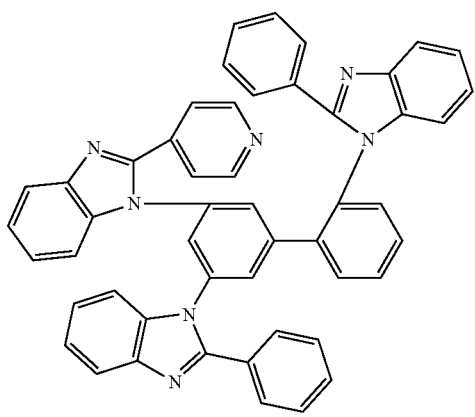
18
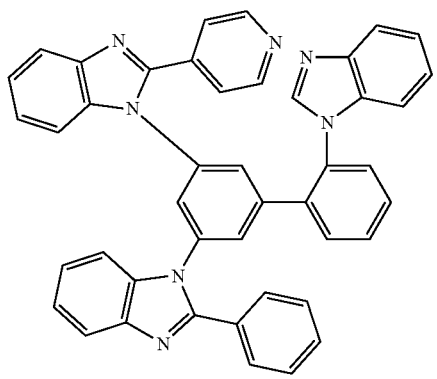
19
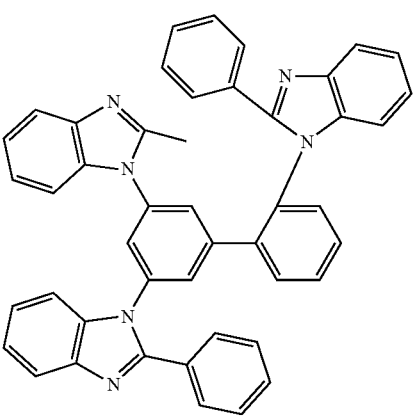
20
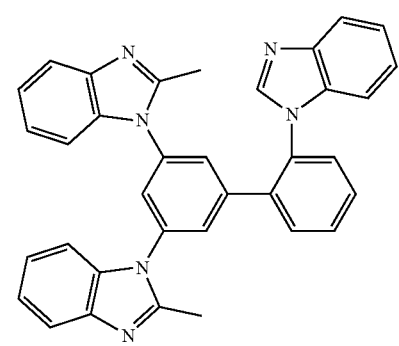
21
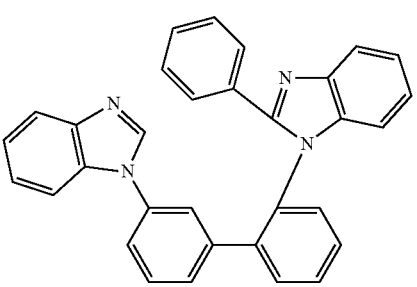
22
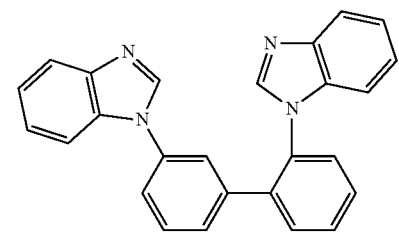
23
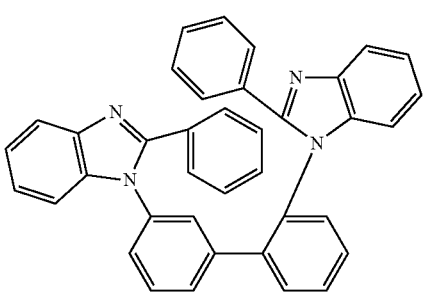

24
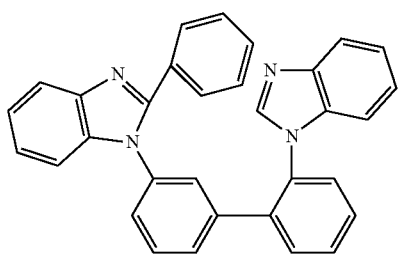
25
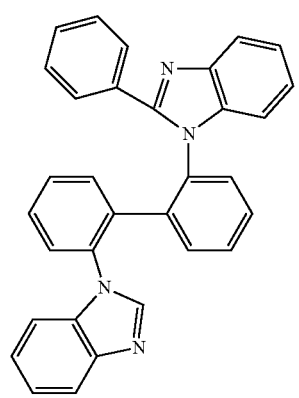
26
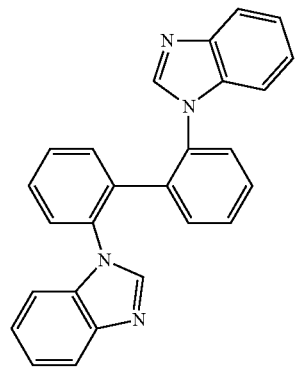
27
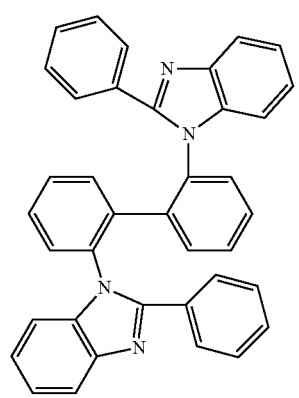
28
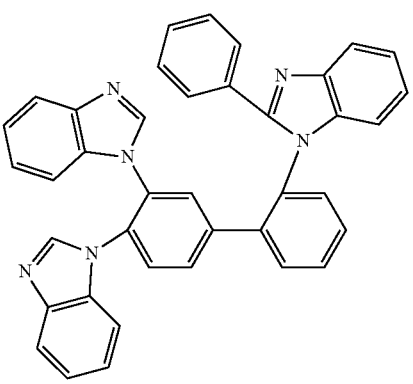
29
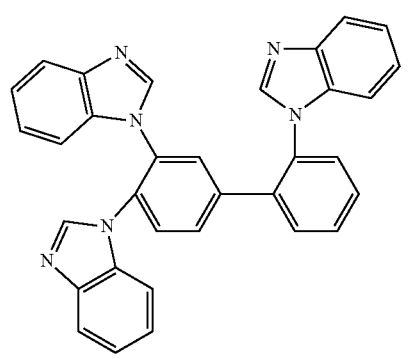
30
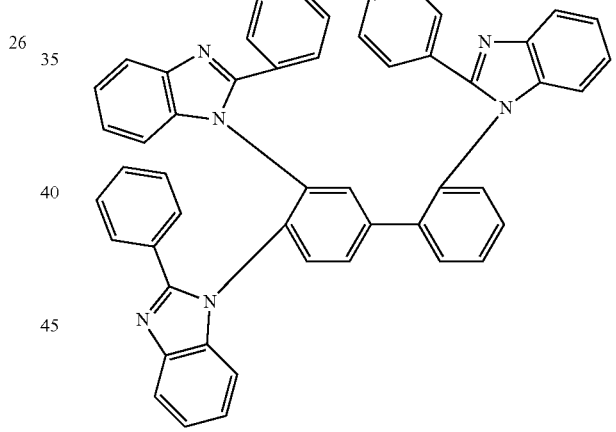
31
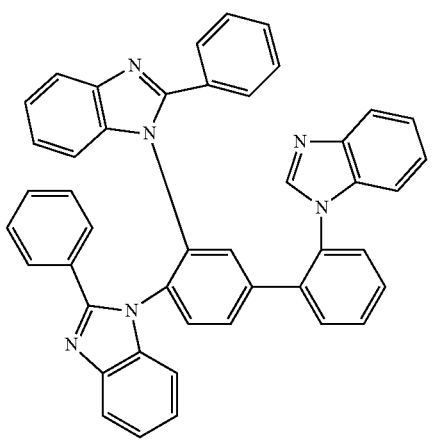

32
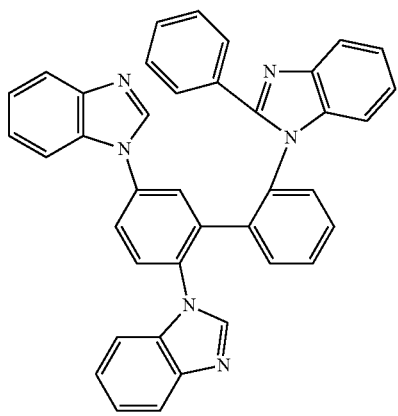
33
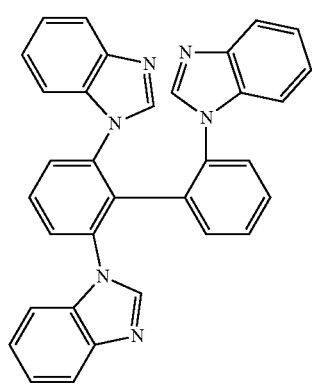
34
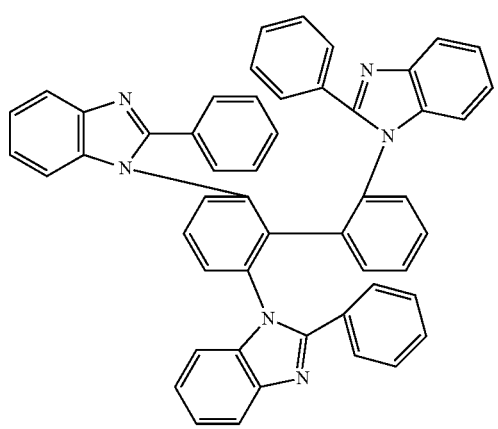
35
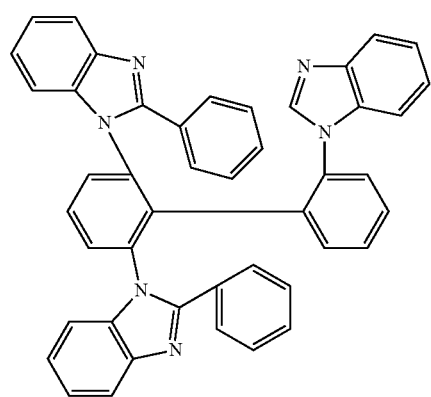
36
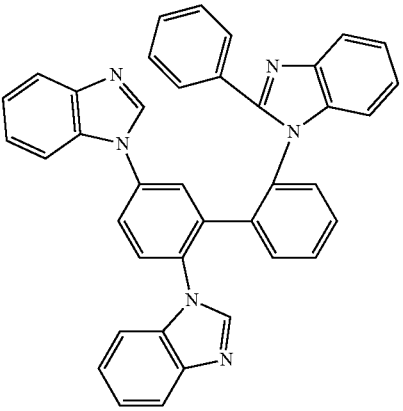
37
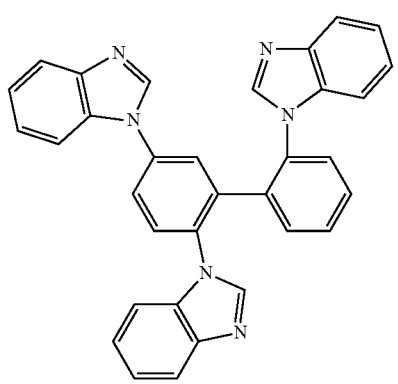
38
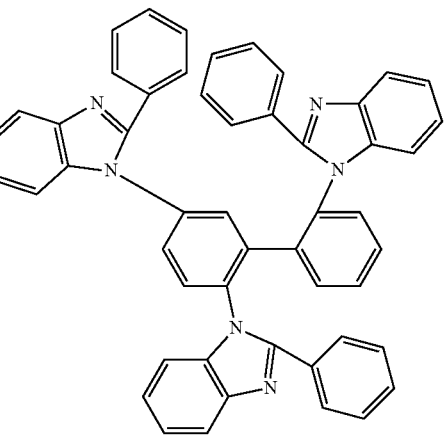

-continued
39
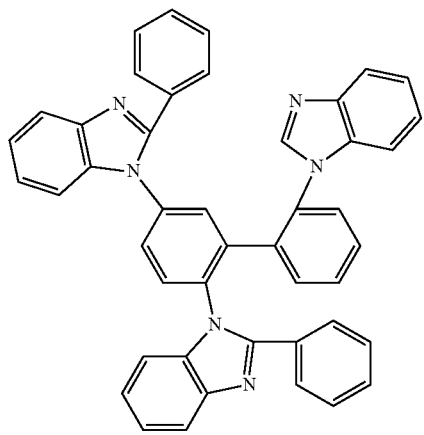
40
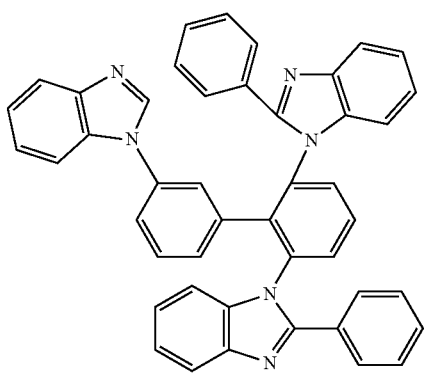
41
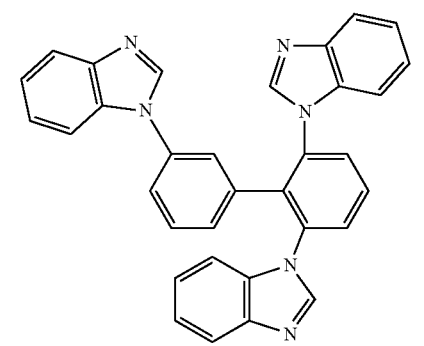
42
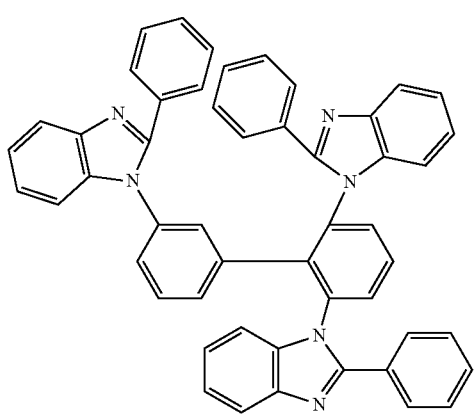
-continued
43
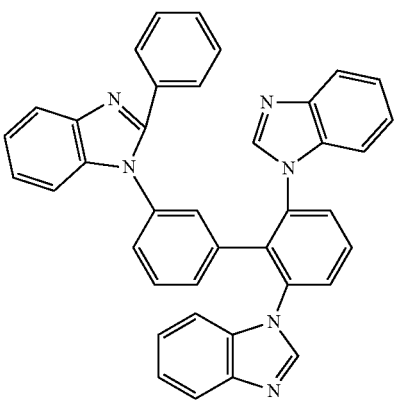
44
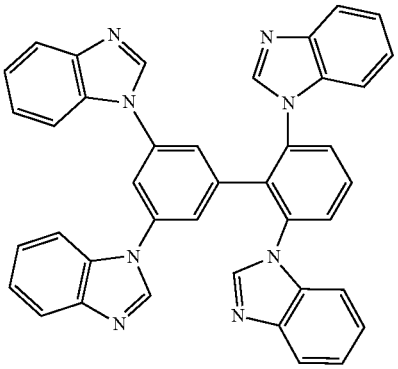
45
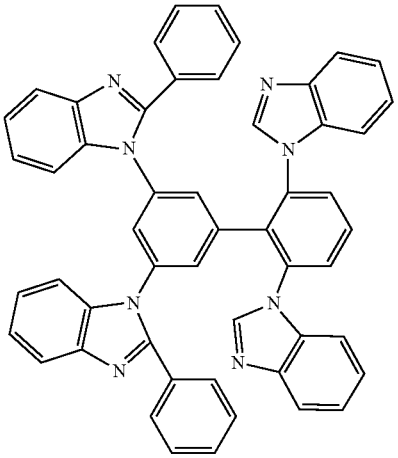
46
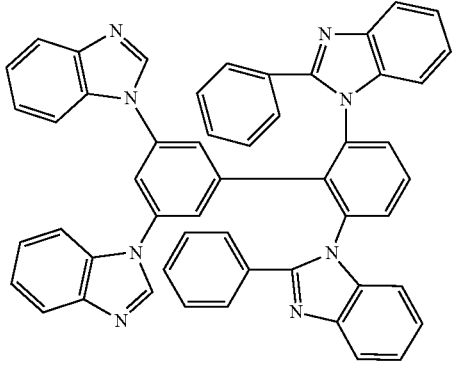

47
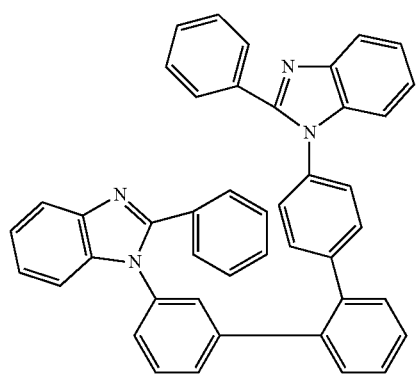
48
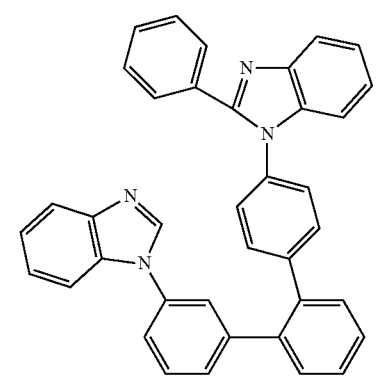
49
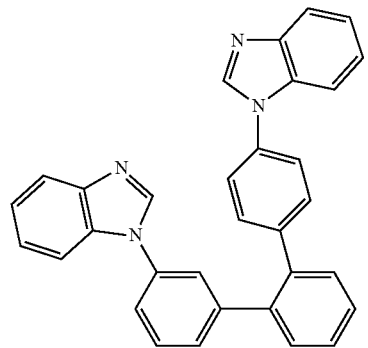
50
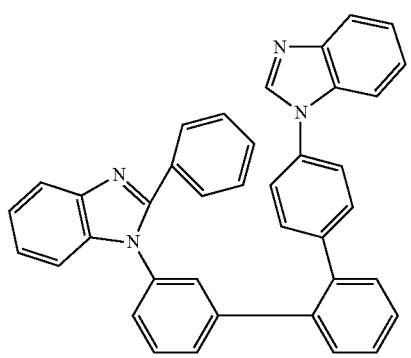
51
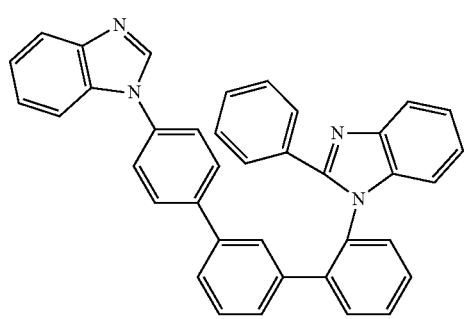
52
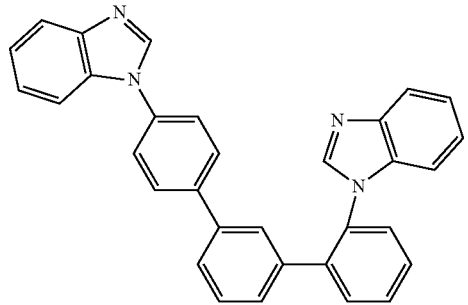
52
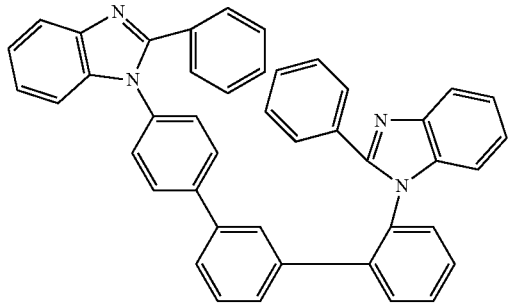
53
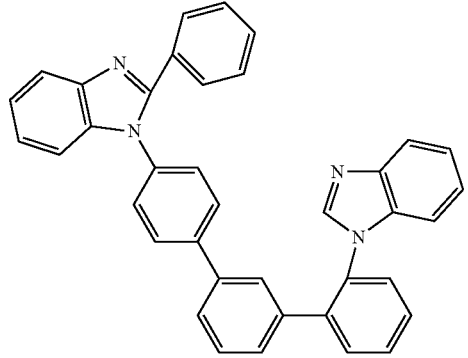

54
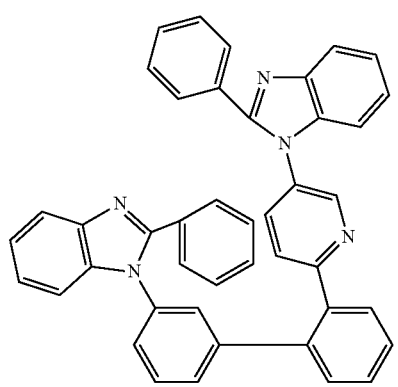
55
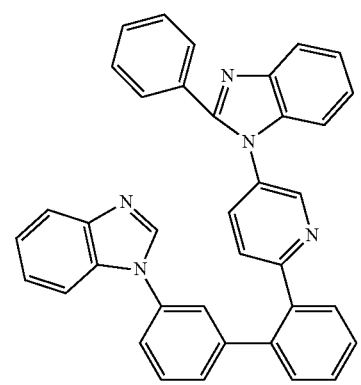
56
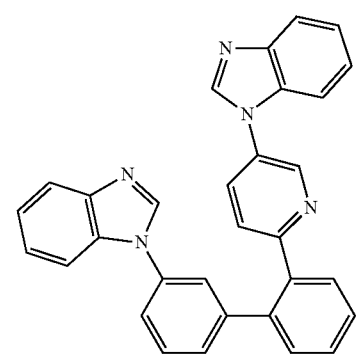
57
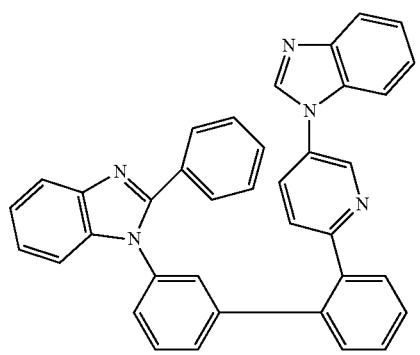
58
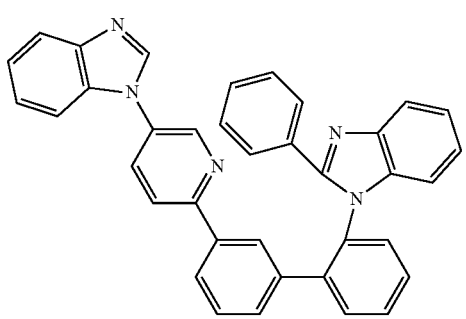
59
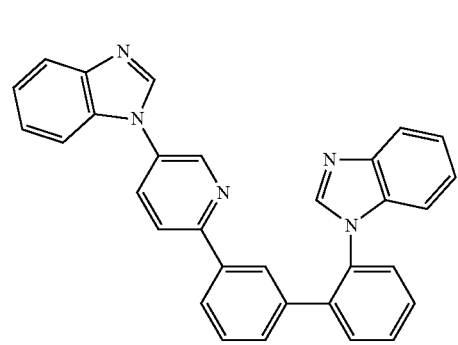
60
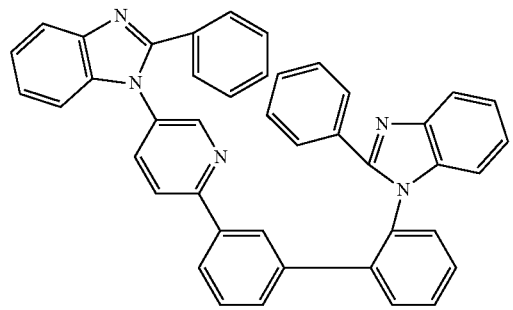
61
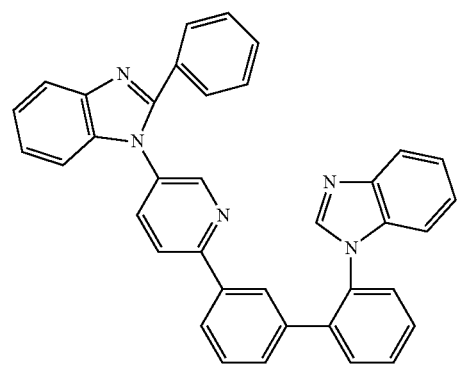

62
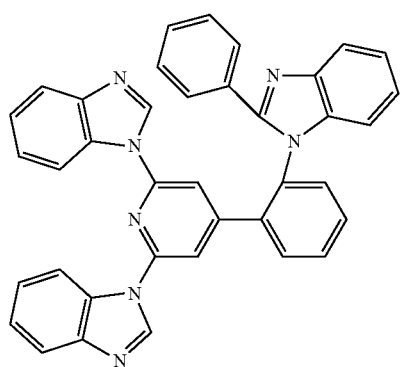
63
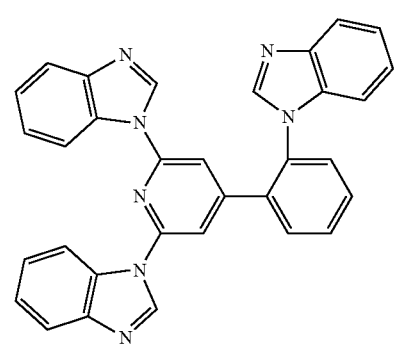
64
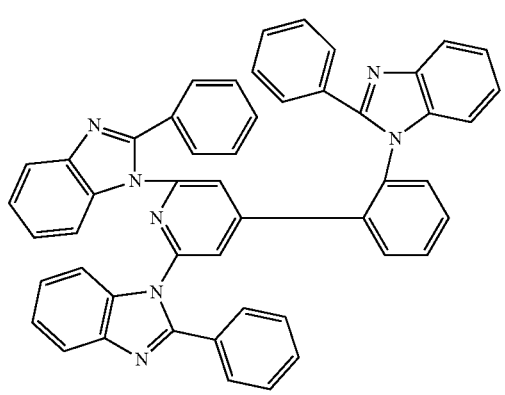
65
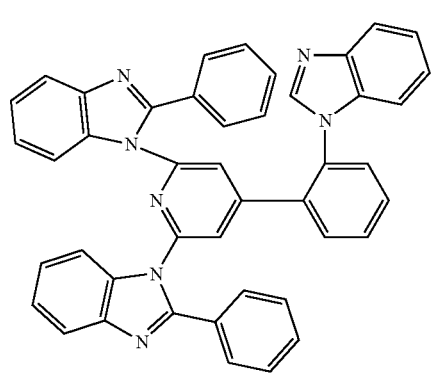
66
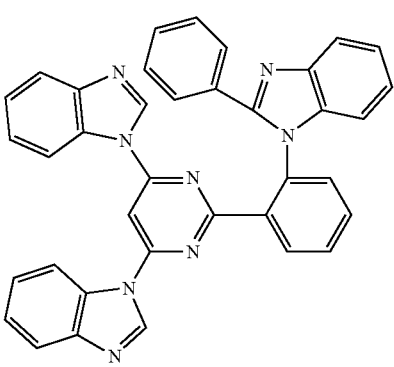
67
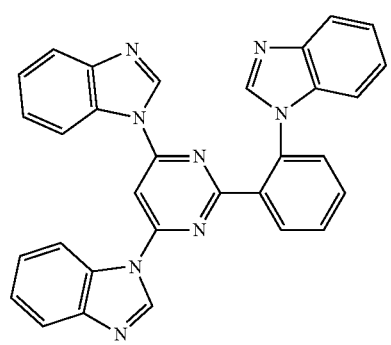
68
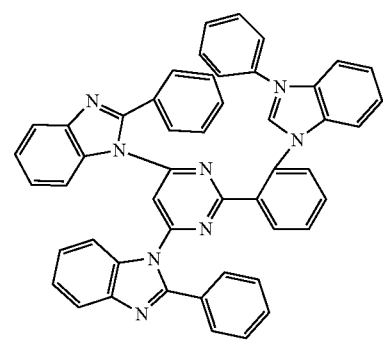
69
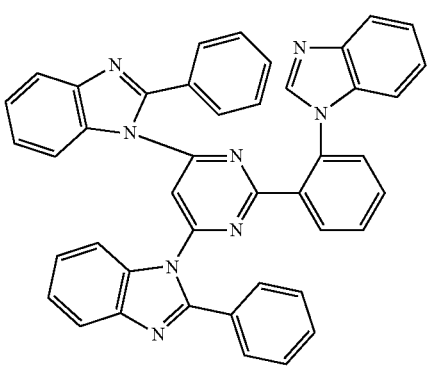

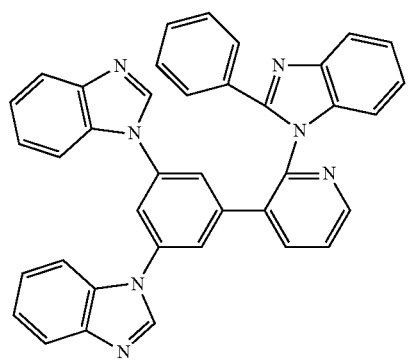
70
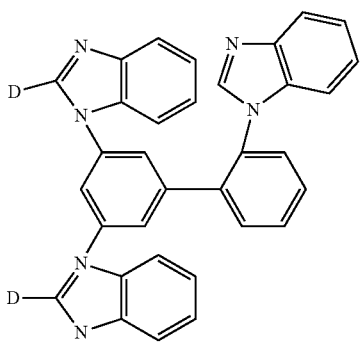
74
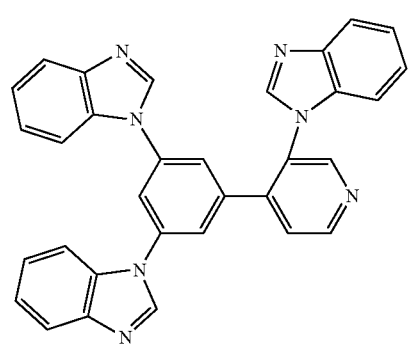
71
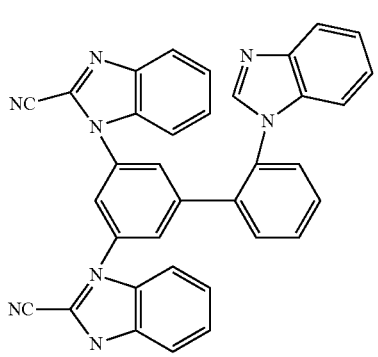
75
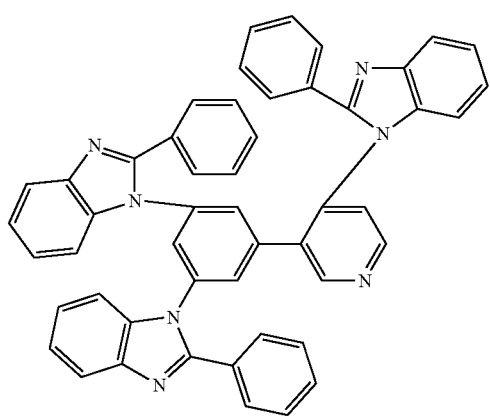
72
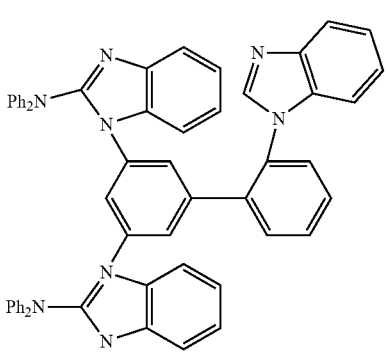
76
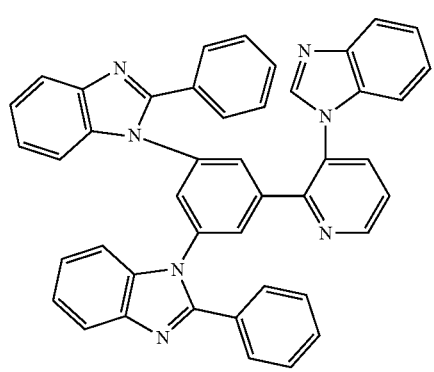
73
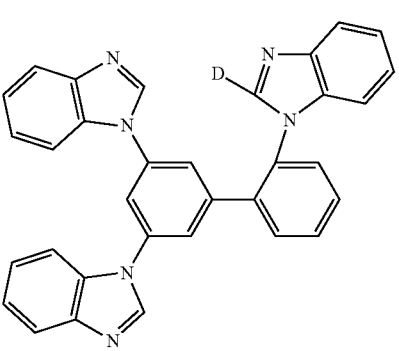
77

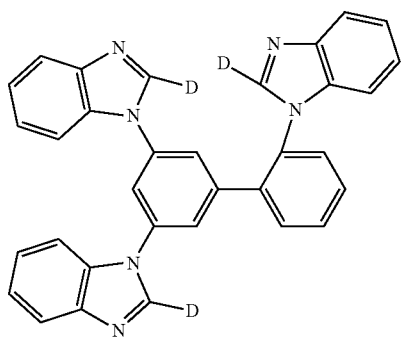

78

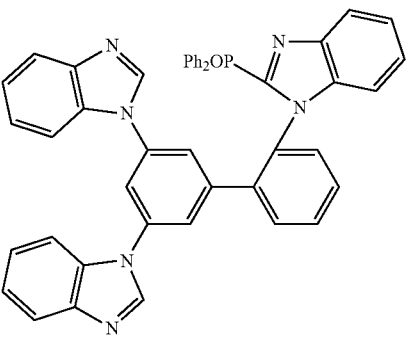

82

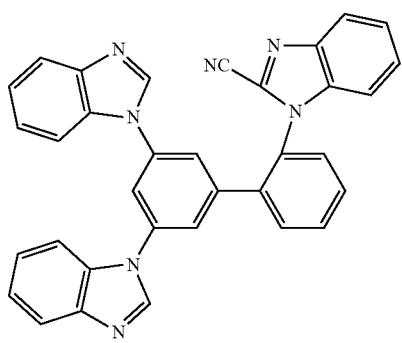

79

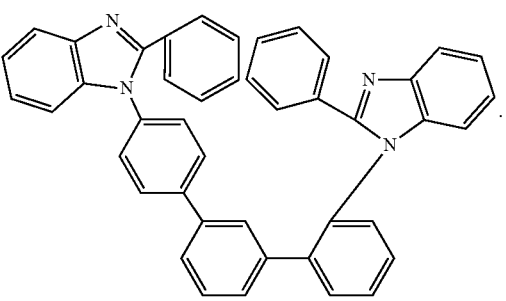

83

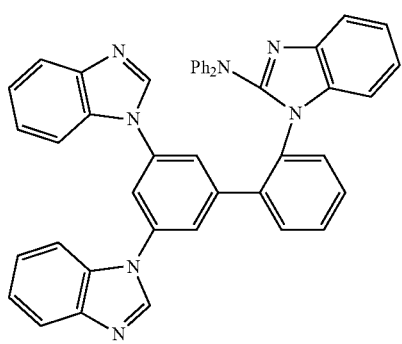

80

81

BRIEF DESCRIPTION OF THE DRAWINGS

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
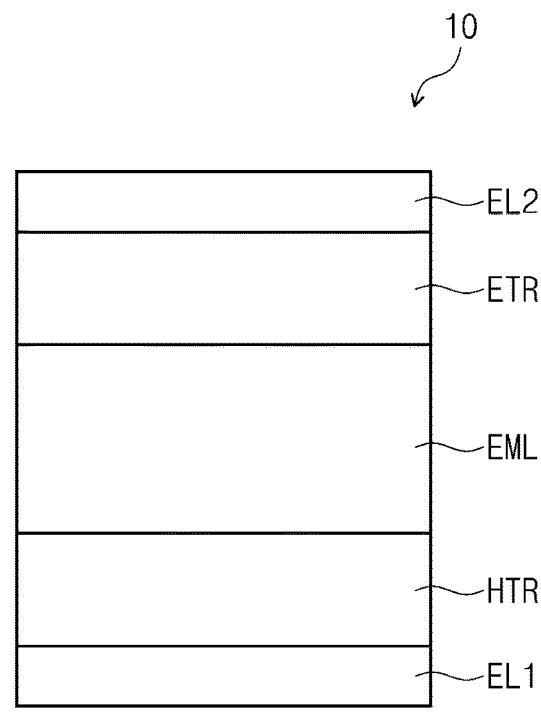
FIG. 1 is a cross-sectional view schematically illustrating an organic electroluminescence device according to an embodiment of the present disclosure.

Because embodiments of the present disclosure may have various modifications and diverse shapes, only certain embodiments are illustrated in the drawings and are described in the detailed description. However, this does not intend to limit the present disclosure within certain embodiments, and it should be understood that the present disclosure covers all the modifications, equivalents, and replacements within the spirit and technical scope of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

When explaining each of the drawings, like reference numerals are used for referring to similar elements. In the accompanying drawings, the dimensions of each structure may be exaggeratingly illustrated for clarity of the present disclosure. Although the terms such as first and second are used herein to describe various components, these components should not be limited by these terms. The terms are only used to distinguish one component from other components. For example, a first component may be referred to as a second component, and similarly a second component may be referred to as a first component without departing from the scope of the present disclosure. The expression of a singular form may include plural forms unless definitely indicating a particular case in terms of the context.

In the present application, it will be understood that the meaning of "comprise" or "have" specifies the presence of a feature, a fixed number, a step, a process, an element, a component, or a combination thereof disclosed in the specification, but does not exclude the possibility of presence or addition of one or more other features, fixed numbers, steps, processes, elements, components, or combination thereof.

As used herein, the term "and/or" includes any and all combinations of one or more of the associated listed items.

In the present application, when a layer, a film, a region, or a plate is referred to as being "above" or "in an upper portion" another layer, film, region, or plate, it can be directly on the layer, film, region, or plate, or intervening layers, films, regions, or plates may also be present. On the contrary to this, when a layer, a film, a region, or a plate is referred to as being "under", "in a lower portion of" another layer, film, region, or plate, it can be directly under the layer, film, region, or plate, or intervening layers, films, regions, or plates may also be present. In addition, it will be understood that when a layer, a film, a region, or a plate is referred to as being 'on' another layer, film, region, or plate, it can be not only on the layer, film, region, or plate, but also under the layer, film, region, or plate.

Hereinafter, an organic electroluminescence device according to an embodiment of the present disclosure and a polycyclic compound included in the same according to an embodiment will be explained referring to the drawings.

FIGS. 1 to 4 are cross-sectional views schematically illustrating an organic electroluminescence device according to an embodiment of the present disclosure. Referring to FIGS. 1 to 4, in an organic electroluminescence device 10 according to an embodiment of the present disclosure, a first electrode EL1 and a second electrode EL2 face each other, and an emission layer EML may be between the first electrode EL1 and the second electrode EL2.

Furthermore, the organic electroluminescence device 10 of an embodiment further includes a plurality of organic layers between the first electrode EL1 and the second electrode EL2 as well as the emission layer EML. The plurality of organic layers may include a hole transport region HTR, and an electron transport region ETR. For example, the organic electroluminescence device 10 according to an embodiment of the present disclosure may include a first electrode EL1, a hole transport region HTR, an emission layer EML, an electron transport region ETR, and a second electrode EL2 which are laminated sequentially. In addition, the organic electroluminescence device 10 of an embodiment may include a capping layer CPL on the second electrode EL2.

The organic electroluminescence device 10 of an embodiment may include a polycyclic compound according to an embodiment described below in the plurality of organic layers between the first electrode EL1 and the second electrode EL2. For example, the polycyclic compound according to an embodiment described below may be included in the emission layer EML or the electron transport region ETR. However, embodiments of the present disclosure are not limited thereto, and the organic electroluminescence device 10 of an embodiment may include the polycyclic compound according to an embodiment described below in the hole transport region HTR which is one of the plurality of organic layers between the first electrode EL1 and the second electrode EL2, or may include the polycyclic compound according to an embodiment described below in the capping layer CPL on the second electrode EL2, as well as in the emission layer EML and the electron transport region ETR.

Figure 2:
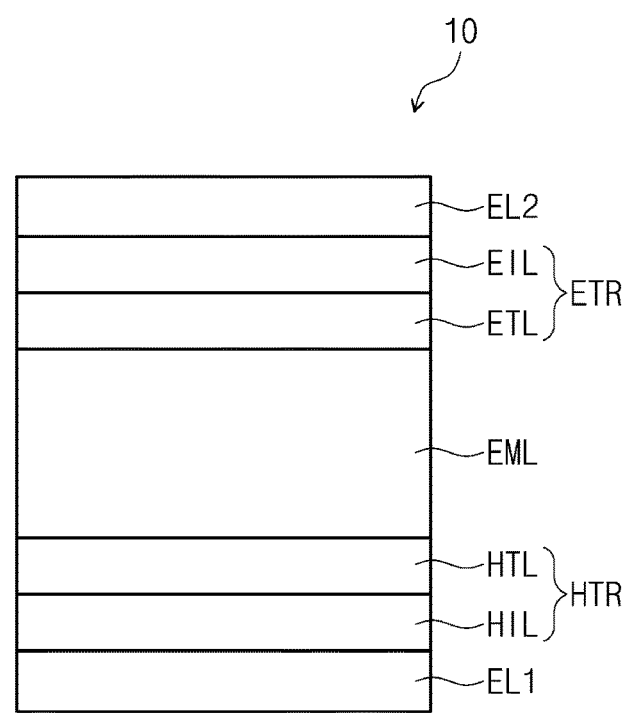
FIG. 2 is a cross-sectional view schematically illustrating an organic electroluminescence device according to an embodiment of the present disclosure.
Figure 3:
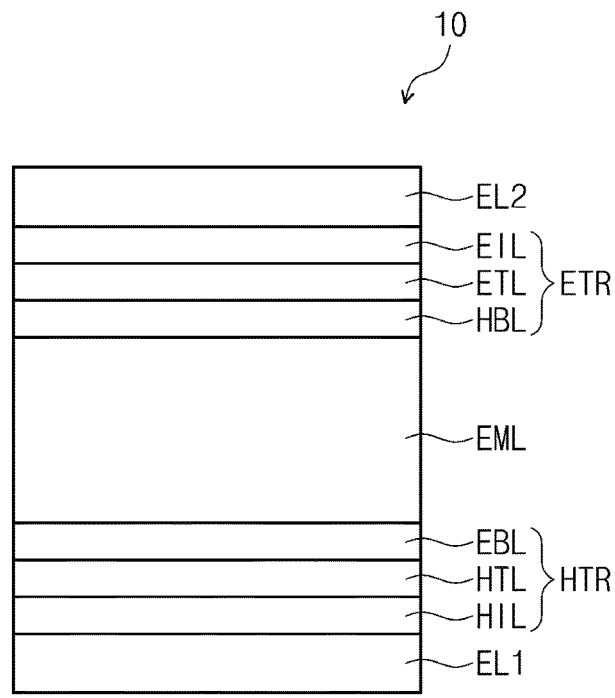
FIG. 3 is a cross-sectional view schematically illustrating an organic electroluminescence device according to an embodiment of the present disclosure.
Figure 4:
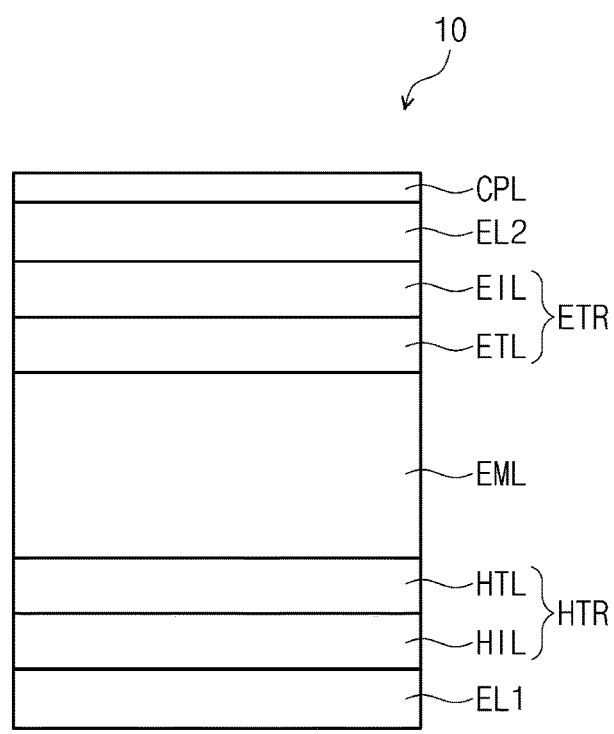
FIG. 4 is a cross-sectional view schematically illustrating an organic electroluminescence device according to an embodiment of the present disclosure.

In some embodiments, when compared with FIG. 1, FIG. 2 shows a cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. Furthermore, when compared with FIG. 1, FIG. 3 shows a cross-sectional view of an organic electroluminescence device 10 of an embodiment, wherein the hole transport region HTR includes a hole injection layer HIL, a hole transport layer HTL, and an electron blocking layer EBL, the electron transport region ETR includes an electron injection layer EIL, an electron transport layer ETL, and a hole blocking layer HBL. When compared with FIG. 2, FIG. 4 shows a cross-sectional view of an organic electroluminescence device 10 of an embodiment including the capping layer CPL on the second electrode EL2.

The first electrode EL1 has conductivity (e.g., electrical conductivity). The first electrode EL1 may be formed of a metal alloy or a conductive compound. The first electrode EL1 may be an anode. In addition, the first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide, for example, indium tin oxide (ITO), indium zinc oxide (IZO), zinc oxide (ZnO), or indium tin zinc oxide (ITZO). When the first electrode EL1 is the transflective electrode or the reflective electrode, the first electrode EL1 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) thereof. In some embodiments, the first electrode EL1 may have a multi-layered structure including a reflective layer or transflective layer and a transparent conductive layer formed of indium tin oxide (ITO), indium zinc oxide (IZO), zinc oxide (ZnO), or indium tin zinc oxide (ITZO). For example, the first electrode EL1 may have, but is not limited to, a three-layer structure of ITO/Ag/ITO. The first electrode EL1 may have a thickness from about 1,000 Å to about 10,000 Å, for example, from about 1,000 Å to about 3,000 Å.

The hole transport region HTR is provided on the first electrode EL1. The hole transport region HTR may include at least one selected from among the hole injection layer HIL, the hole transport layer HTL, the hole buffer layer, and the electron blocking layer EBL. The hole transport region HTR may have a thickness, for example, from about 50 Å to about 15,000 Å.

The hole transport region HTR may have a multilayer structure having a single layer formed of a single material, a single layer formed of materials different from each other, or a plurality of layers formed of materials different from each other.

For example, the hole transport region HTR may have a single layer structure of a hole injection layer HIL or a hole transport layer HTL, or a single layer structure formed of a hole injection material and a hole transport material. In addition, the hole transport region HTR may have a single layer structure formed of a plurality of different materials, or a structure of the hole injection layer HIL/the hole transport layer HTL, the hole injection layer HIL/the hole transport layer HTL/the hole buffer layer, the hole injection layer HIL/the hole buffer layer, the hole transport layer HTL/the hole buffer layer, or the hole injection layer HIL/the hole transport layer HTL/the electron blocking layer EBL which are sequentially laminated from the first electrode EL1, but embodiments are not limited thereto.

The hole transport region HTR may be formed by using various suitable methods such as a vacuum deposition method, a spin coating method, a casting method, a Langmuir-Blodgett (LB) method, an inject printing method, a laser printing method, and/or a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-[tris(3-methylphenyl)phenylamino]triphenylamine] (m-MTDATA), 4,4',4''-tris(N,N-diphenylamino)triphenylamine (TDATA), 4,4',4''-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-I-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorene derivatives, N,N'-bis(3-methylphenyl)-N,N'-diphenyl-[1,1-biphenyl]-4,4'-diamine (TPD), triphenylamine derivatives such as 4,4',4''-tris(N-carbazolyl) triphenylamine (TCTA), N,N'-di(naphthalene-I-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-Bis(N-carbazolyl)benzene (mCP), etc.

The hole transport region HTR may have a thickness from about 50 Å to about 10,000 Å, for example, from about 100 Å to about 5,000 Å. The hole injection layer HIL may have a thickness, for example, from about 30 Å to about 1,000 Å, the hole transport layer HTL may have a thickness from about 30 Å to about 1,000 Å. For example, the electron blocking layer EBL may have a thickness from about 10 Å to about 1,000 Å. When the thickness of each of the hole transport region HTR, the hole injection layer HIL, the hole transport layer HTL, and the electron blocking layer EBL satisfies the above-described range, suitable or satisfactory hole transport characteristics may be achieved without a substantial increase in driving voltage.

The hole transport region HTR may further include a charge generating material in addition to the above-described materials to improve conductivity (e.g., electrical conductivity). The charge generating material may be uniformly or non-uniformly dispersed into the hole transport region HTR. The charge generating material may be, for example, a p-dopant. The p-dopant may be one of quinone derivatives, metal oxides, and cyano group-containing compounds, but is not limited thereto. For example, non-limiting examples of the p-dopant may include, but are not limited to, quinone derivatives such as tetracyanoquinodimethane (TCNQ) and 2,3,5,6-tetrafluoro-tetracyanoquinodimethane (F4-TCNQ), metal oxides such as tungsten oxides and molybdenum oxides.

As described above, the hole transport region HTR may further include at least one of the hole buffer layer or the electron blocking layer EBL in addition to the hole injection layer HIL and the hole transport layer HTL. The hole buffer layer may compensate a resonance distance according to the wavelength of light emitted from the emission layer EML to increase luminous efficiency. A material that can be contained in the hole transport region HTR may be used as a material to be contained in the hole buffer layer. The electron blocking layer EBL is a layer that blocks or reduces the injection of electrons from the electron transport region ETR to the hole transport region HTR.

The emission layer EML is on the hole transport region HTR. The emission layer EML may have a thickness, for example, from about 100 Å to about 1,000 Å, or from about 100 Å to about 300 Å. The emission layer EML may have a multilayer structure having a single layer formed of a single material, a single layer formed of materials different from each other, or a plurality of layers formed of materials different from each other.

The emission layer EML may include the polycyclic compound of an embodiment. The polycyclic compound of an embodiment includes two aromatic includes two aromatic 6-membered rings which are linked by a single bond, and a plurality of benzimidazole groups which are substituted at the two aromatic 6-membered rings. The aromatic 6-membered ring may refer to an aromatic ring having six atoms for forming a ring.

In an embodiment, each of the two aromatic 6-membered rings of the polycyclic compound includes a carbon atom or a nitrogen atom as an atom for forming a ring. For example, all atoms for forming a ring of the two aromatic 6-membered rings may be a carbon atom. In other words, the two aromatic 6-membered rings may be biphenyl. However, embodiments are not limited thereto, and an atom for forming a ring of the two aromatic 6-membered rings may include one or more nitrogen atoms. For example, any one ring of the two aromatic 6-membered rings may be pyridine or pyrimidine. However, embodiments are not limited thereto.

The polycyclic compound of an embodiment may include a plurality of benzimidazole groups as a substituent. For example, the polycyclic compound may include 2 to 4 of benzimidazole groups as a substituent. However, embodiments are not limited thereto.

At least one of the plurality of benzimidazole groups may be substituted at the ortho-position at a respective one of the aromatic 6-membered rings. In the present description, the substituted position (e.g., the substituted positions of the polycyclic compound), such as the ortho position is defined with respect to a single bond which links the two aromatic 6-membered rings. For example, with respect to a single bond which links the two aromatic 6-membered rings, the plurality of benzimidazole groups may be substituted at the ortho-position and the meta-position of at least one of the two aromatic 6-membered rings. In the polycyclic compound of an embodiment, the benzimidazole group may not be substituted at the para-position of the two aromatic 6-membered rings. For example, the polycyclic compound may not have a benzimidazole group at one or both of the para-positions of the two aromatic 6-membered rings, and/or the polycyclic compound may not have a substituent (e.g., may have only hydrogen) at one or both of the para-positions of the two aromatic 6-membered rings. However, embodiments are not limited thereto.

In the present description, the term "substituted or unsubstituted" may mean substituted or unsubstituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the present description, the expression "being bonded to an adjacent group to form a ring" may mean being bonded to an adjacent group to form a substituted or unsubstituted hydrocarbon ring, or a substituted or unsubstituted heterocyclic ring. The hydrocarbon ring includes an aliphatic hydrocarbon ring and an aromatic hydrocarbon ring. The heterocyclic ring includes an aliphatic heterocyclic ring and an aromatic heterocyclic ring. The hydrocarbon ring and the heterocyclic ring may be monocyclic or polycyclic. In addition, a ring formed by being bonded to an adjacent group may be linked to another ring to form a spiro structure.

In the present description, the term "adjacent group" may mean a substituent which is substituted for an atom directly linked to an atom for which the substituent is substituted, another substituent which is substituted for an atom for which the substituent is substituted, or a substituent sterically closest to the substituent. For example, two methyl groups in 1,2-dimethylbenzene may be interpreted as "adjacent groups" to each other, and two ethyl groups in 1,1-diethylcyclopentane may be interpreted as "adjacent groups" to each other.

In the present description, examples of the halogen atom may include a fluorine atom, a chlorine atom, a bromine atom, and an iodine atom.

In the present description, the alkyl group may be a linear, branched or cyclic type (e.g., may be a linear, branched, or cyclic alkyl group). The number of carbons in the alkyl group may be 1 to 50, 1 to 30, 1 to 20, 1 to 10, or 1 to 6. Examples of the alkyl group may include, but are not limited to, methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc.

In the present description, the term "hydrocarbon ring group" refers to any functional group or substituent derived from an aliphatic hydrocarbon ring. The hydrocarbon ring group may be a saturated hydrocarbon ring group having carbon atoms for forming a ring of 5 to 20.

In the present description, the term "aryl group" refers to an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include, but are not limited to, a phenyl group, a naphthyl group, a fluorenyl group, an anthracenyl group, a phenanthryl group, a biphenyl group, a terphenyl group, a quaterphenyl group, a quinqphenyl group, a sexiphenyl group, a triphenylenyl group, a pyrenyl group, a benzofluoranthenyl group, a chrysenyl group, etc.

In the present description, the fluorenyl group may be substituted, and two substituents may be combined with each other to form a spiro structure. Examples of the substituted fluorenyl group may be as shown below. However, an embodiment of the present disclosure is not limited thereto.

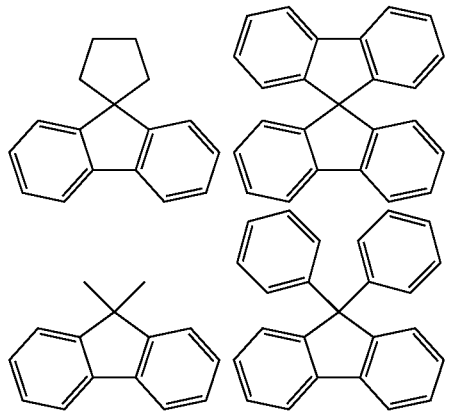

In the present description, the term "heterocyclic group" refers to any functional group or substituent derived a ring including one or more selected from among B, O, N, P, Si, and Se as a heteroatom. The heterocyclic group includes an aliphatic heterocyclic group and an aromatic heterocyclic group. The aromatic heterocyclic group may be a heteroaryl group. The aliphatic heterocyclic ring and the aromatic heterocyclic ring may be monocyclic or polycyclic.

In the case where the heterocyclic group includes two or more heteroatoms, two or more heteroatoms may be the same as or different from each other. The heterocyclic group may be a monocyclic heterocyclic group or a polycyclic heterocyclic group, and include a heteroaryl group. The number of carbons for forming a ring of the heterocyclic group may be 2 to 30, 2 to 20, or 2 to 10.

The number of carbons for forming a ring of the aliphatic heterocyclic group may be 2 to 30, 2 to 20, or 2 to 10. Examples of the aliphatic heterocyclic group may include, but are not limited to, oxirane group, thiirane group, pyrrolidine group, piperidine group, tetrahydrofuran group, tetrahydrothiophene group, thiane group, tetrahydropyran group, 1,4-dioxane group, etc.

In the case where the heteroaryl group includes two or more heteroatoms, two or more heteroatoms may be the same as or different from each other. The heteroaryl group may be a monocyclic heterocyclic group or a polycyclic heterocyclic group. The number of carbons for forming a ring of the heteroaryl group may be 2 to 30, 2 to 20, or 2 to 10. Examples of the heteroaryl group may include, but are not limited to, thiophene group, furan group, pyrrole group, imidazole group, triazole group, pyridine group, bipyridine group, pyrimidine group, triazine group, triazole, acridyl group, pyridazine group, pyrazinyl group, quinoline group, quinazoline group, quinoxaline group, phenoxazine group, phthalazine group, pyrido pyrimidine group, pyrido pyrazine group, pyrazino pyrazine group, isoquinoline group, indole group, carbazole group, N-arylcarbazole group, N-heteroarylcarbazole group, N-alkylcarbazole group, benzoxazole group, benzoimidazole group, benzothiazole group, benzocarbazole group, benzothiophene group, dibenzothiophene group, thienothiophene group, benzofuran group, phenanthroline group, thiazole group, isooxazole group, oxazole group, oxadiazole group, thiadiazole group, phenothiazine group, dibenzosilole group, dibenzofuran group, etc.

In the present description, the above description with respect to the aryl group may be applied to an arylene group except that the arylene group is a divalent group. The above description with respect to the heteroaryl group except may be applied to a heteroarylene group except that the heteroarylene group is a divalent group.

In the present description, the alkenyl group may be a linear or branched chain (e.g., may be a linear or branched alkenyl group). The number of carbons is 2 to 30, 2 to 20 or 2 to 10, but is not limited thereto. Examples of the alkenyl group include, but are not limited to, a vinyl group, 1-butenyl group, 1-pentenyl group, 1,3-butadienyl aryl group, styrenyl group, styryl vinyl group, etc.

In the present description, the carbon number of the amine group may be 1 to 30, but is not particularly limited thereto. The amine group may include an alkyl amine group and an aryl amine group. Examples of the amine group may include, but are not limited to, methylamine group, dimethylamine group, phenylamine group, diphenylamine group, naphthylamine group, 9-methyl-anthracenylamine group, triphenylamine group, etc.

In the present description, the alkyl group in alkylamine group is the same as the examples of the alkyl group described above.

In the present description, the aryl group in arylamine group is the same as the examples of the aryl group described above.

In the present description, the term "direct linkage" may mean a single bond.

In some embodiments, in the present description, "-*" means the position to be linked.

A polycyclic compound in an embodiment may be represented by Formula 1 below:

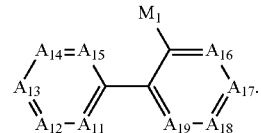

[Formula 1]

In Formula 1 above, $A_{11}$ to $A_{19}$ are each independently N or CR, For example, all of $R_{11}$ to $R_{19}$ may be CR. For example, Formula 1 may be a substituted biphenyl group. However, embodiments are not limited thereto, $A_{11}$ to $A_{19}$ may include one nitrogen atom or two nitrogen atoms. In this case, Formula 1 may include pyridine or pyrimidine. However, embodiments are not limited thereto.

R may be a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 6 to 30 carbon atoms for forming a ring, or $M_2$, or may be combined with an adjacent group to form a ring.

At least one selected from among $A_{11}$ to $A_{15}$ is $CM_2$. In an embodiment, one to three selected from among $A_{11}$ to $A_{19}$ above may be $CM_2$. For example, each of the two aromatic 6-membered rings includes at least one of benzimidazole groups.

In some embodiments, $M_1$ and $M_2$ are each independently represented by Formula 2 below:

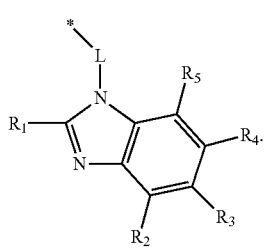

[Formula 2]

In Formula 2 above, $R_1$ to $R_5$ may be each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or may be combined with an adjacent group to form a ring. In some embodiments, $R_1$ of an embodiment may be deuterium, a cyano group, a substituted amine group, a substituted silyl group, a substituted phosphine oxide group. For example, the substituted amine group may be an amine group which is substituted with a phenyl group. The substituted silyl group may be a silyl group which is substituted with a phenyl group. The substituted phosphine oxide group may be a phosphine oxide group which is substituted with a phenyl group. In some embodiments, $R_1$ of an embodiment may be an alkyl group. For example, $R_1$ may be a methyl group. In some embodiments, $R_1$ of an embodiment may be an aromatic 6-membered ring. For example, $R_1$ may be a phenyl group or a pyridinyl group. However, embodiments are not limited thereto.

L is a direct linkage, a substituted or unsubstituted arylene group having 6 to 30 carbon atoms, or a substituted or unsubstituted heteroarylene group having 2 to 30 carbon atoms. For example, L may be a direct linkage, a phenylene group, or a pyridinyl group. However, embodiments are not limited thereto.

In embodiment, the polycyclic compound represented Formula 1 may be represented by any one selected from among Formula 1-1 to Formula 1-7 below:

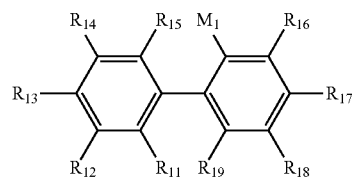

[Formula 1-1]

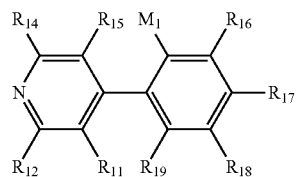

[Formula 1-2]

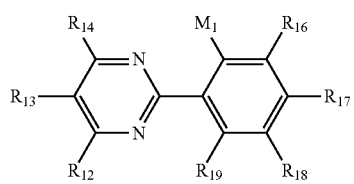

[Formula 1-3]

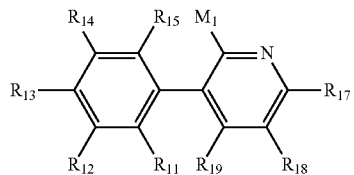

[Formula 1-4]

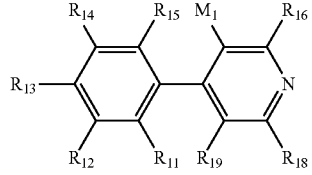

[Formula 1-5]

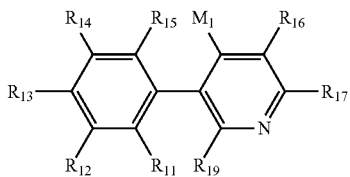

[Formula 1-6]

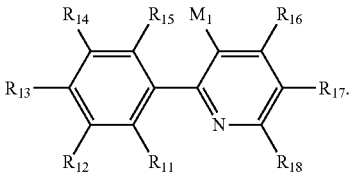

[Formula 1-7]

In Formula 1-1 to Formula 1-7 above, $R_{11}$ to $R_{19}$ may be each independently a hydrogen atom, or represented by Formula 2. At least one selected from among $R_{11}$ to $R_{19}$ is represented by Formula 2. For example, a substituent represented by Formula 2 may be substituted at the ortho-position or meta-position with respect to a single bond which links the aromatic 6-membered ring.

In Formula 1-1 to Formula 1-7 above, $M_1$ is the same as that defined with respect to Formula 1. By $M_1$, the polycyclic compound of an embodiment includes at least one of substituents which are represented by Formula 2 and which are substituted at the ortho-position.

In embodiment, the substituent represented by Formula 2 may be represented by any one selected from among Formula 2-1 to Formula 2-4 below:

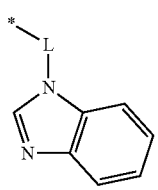

[Formula 2-1]

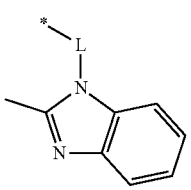

[Formula 2-2]

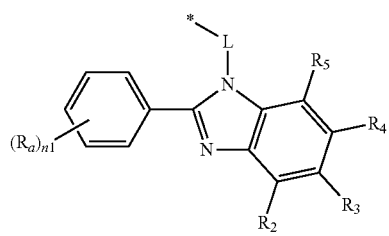

[Formula 2-3]

[Formula 2-4]

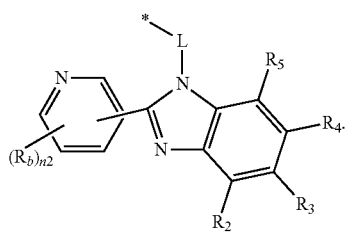

In Formula 2-1 to Formula 2-4 above, $R_a$ and $R_b$ may be each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or may be combined with an adjacent group to form a ring.

$n_1$ and $n_2$ may be each independently an integer of 0 to 4. For example, $n_1$ may be 0. For example, $n_2$ may be 0. However, embodiments are not limited thereto. When $n_1$ is an integer of 2 or more, a plurality of $R_a$'s may be the same as or different from each other. When $n_2$ is an integer of 2 or more, a plurality of $R_b$'s may be the same as or different from each other.

In Formula 2-1 to Formula 2-4 above, $R_2$ to $R_5$ and L are the same as those defined with respect to Formula 2.

In embodiment, the polycyclic compound represented by Formula 1 may be any one selected from among compounds represented by Compound Group 1 below:

[Compound Group 1]

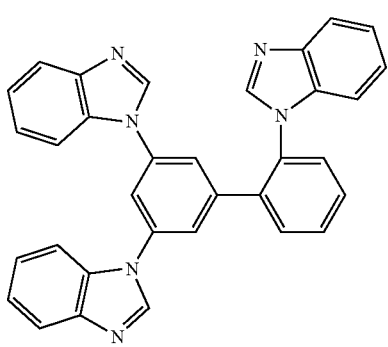

1

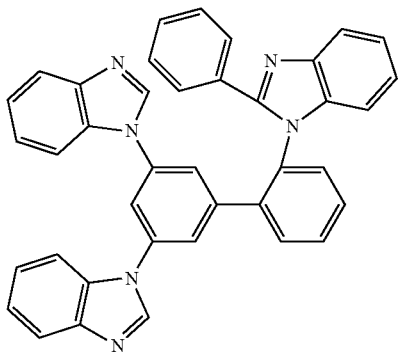

2

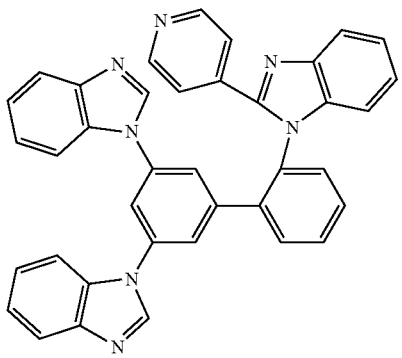

3

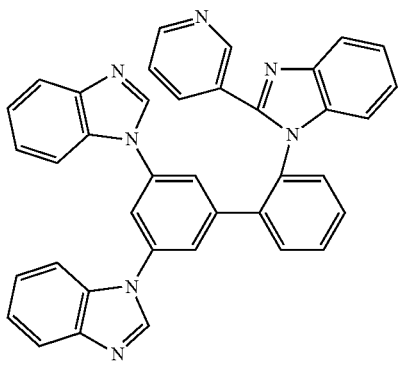

4

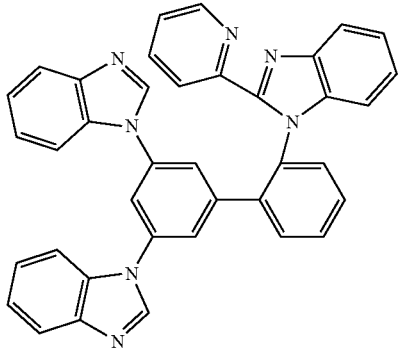

5

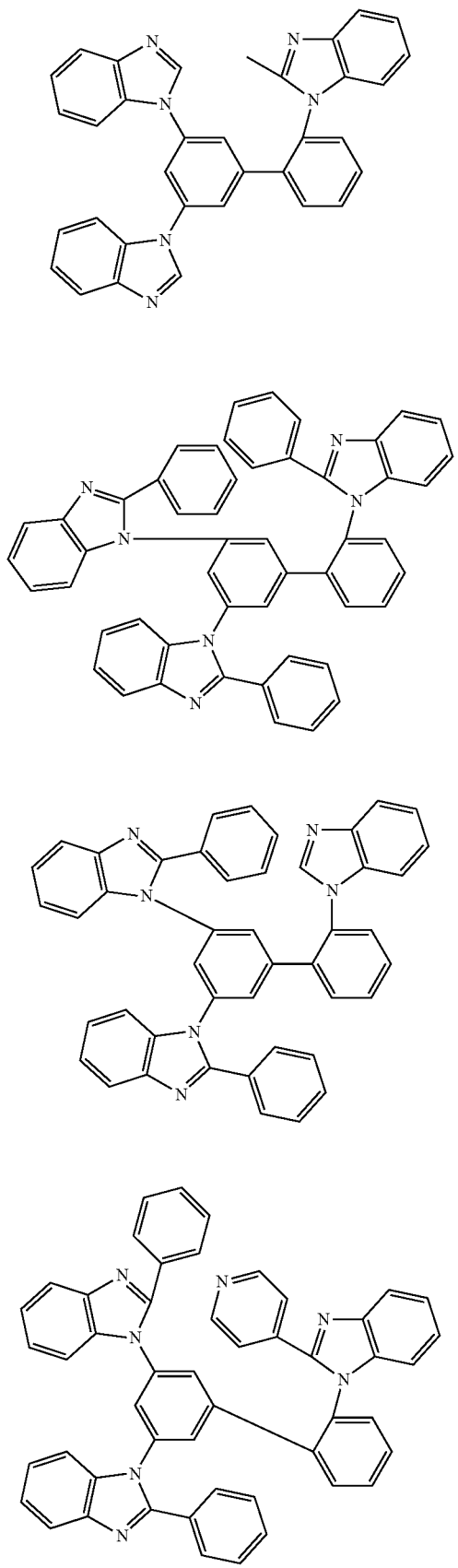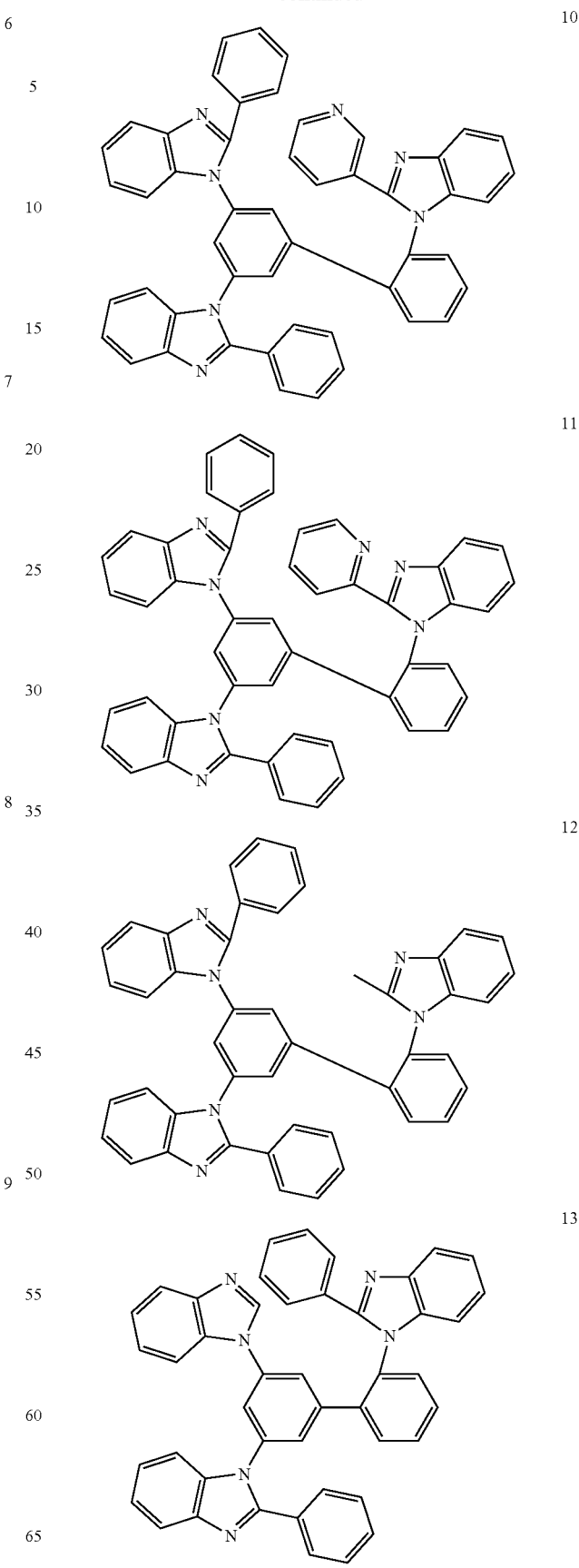

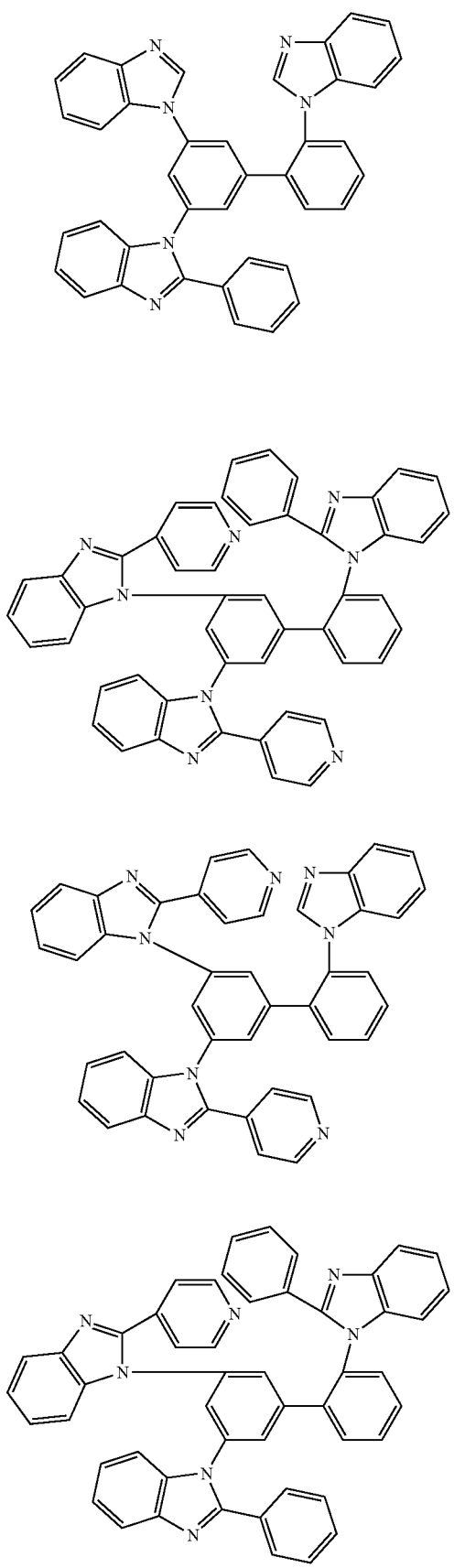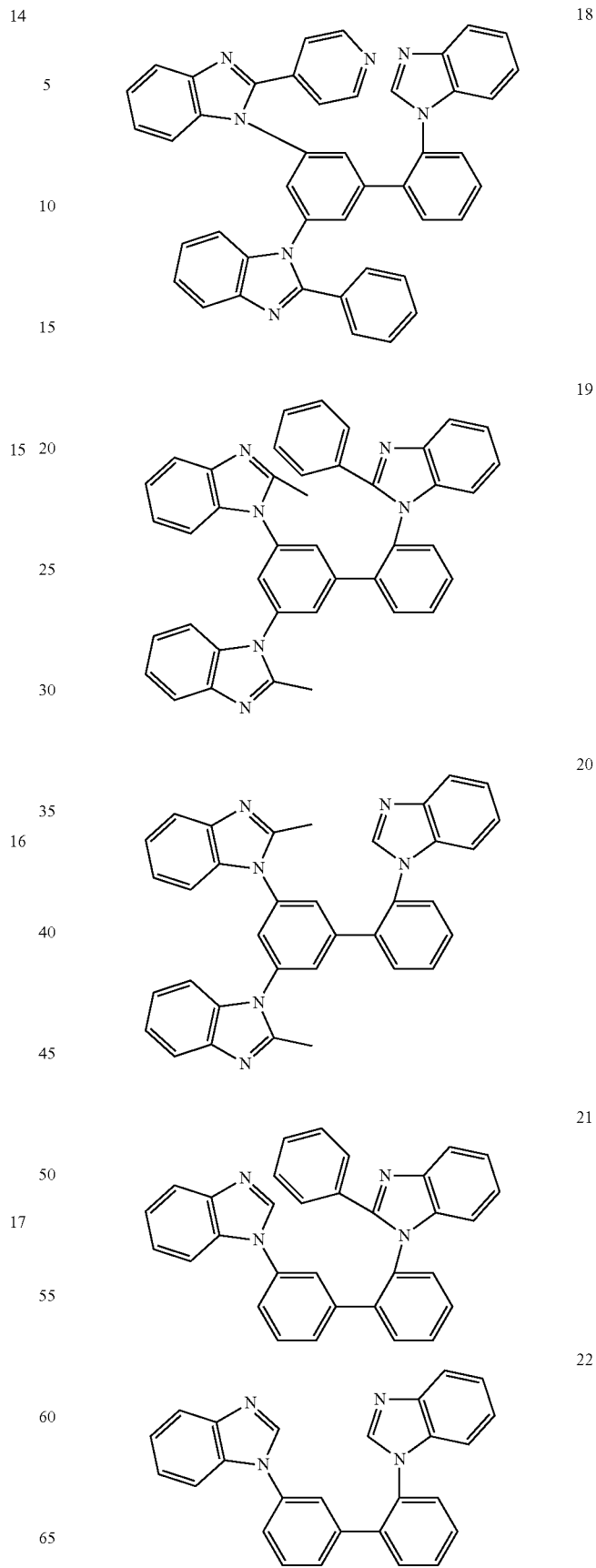

23
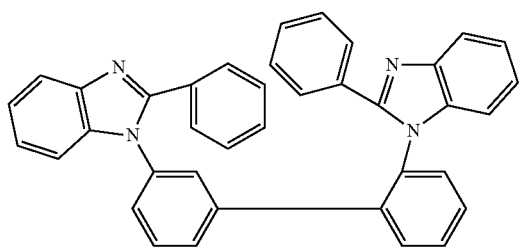
24
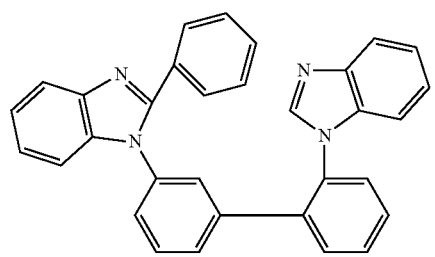
25
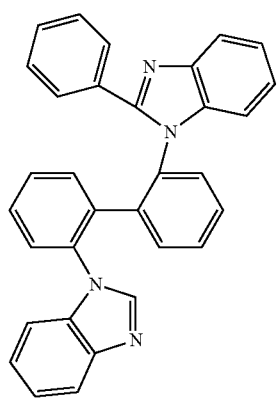
26
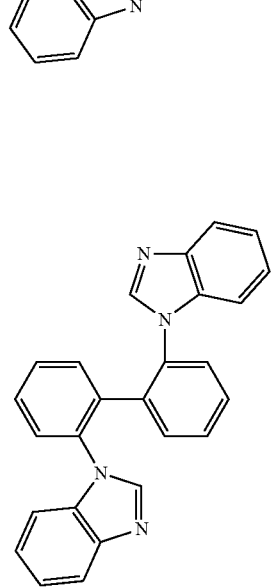
27
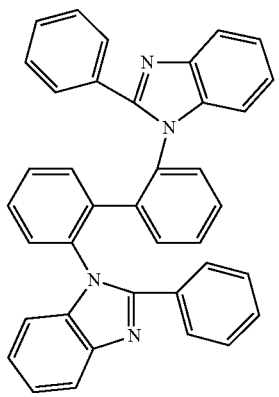
28
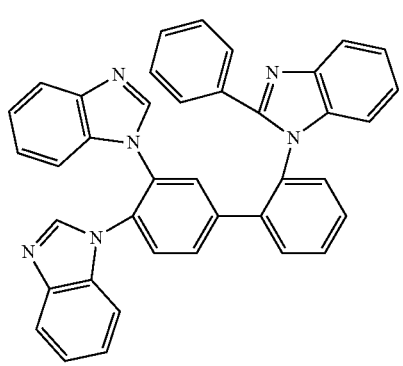
29
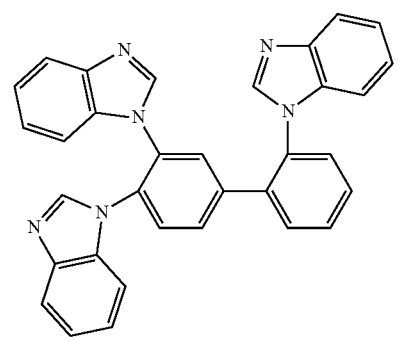
30
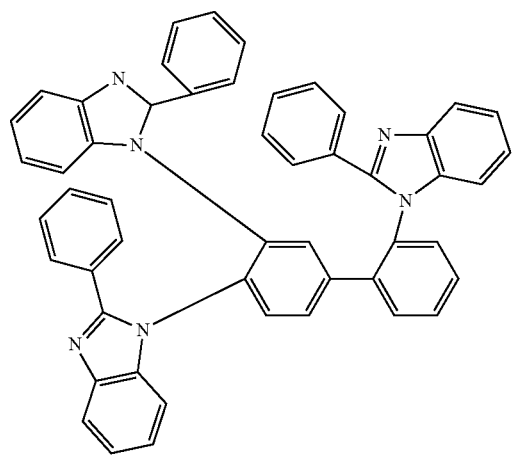

31
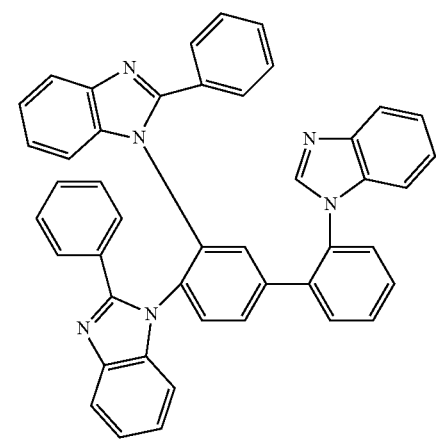
32
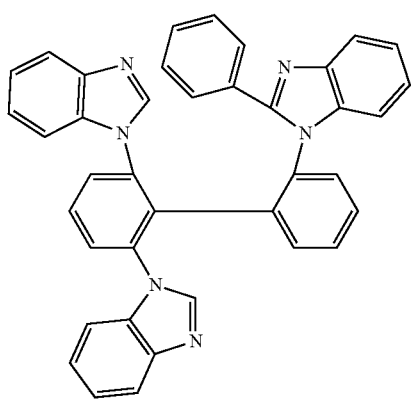
33
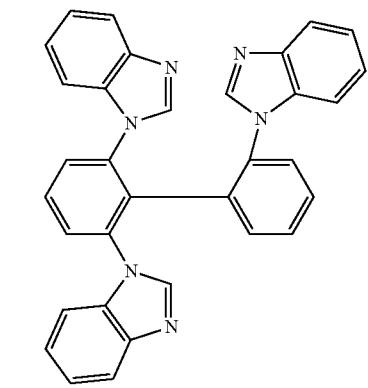
34
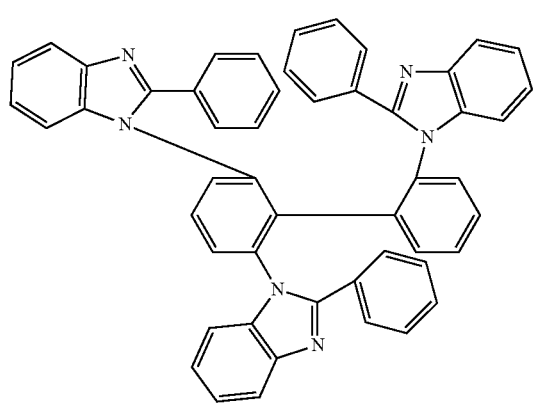
35
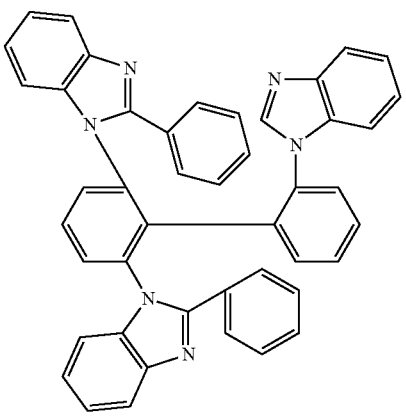
36
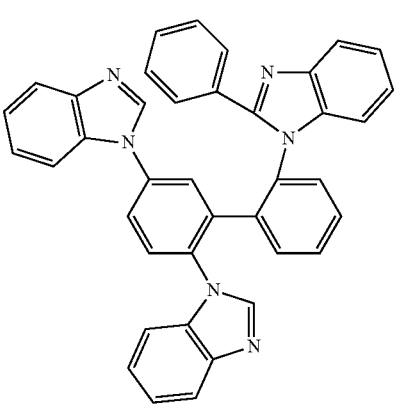
37
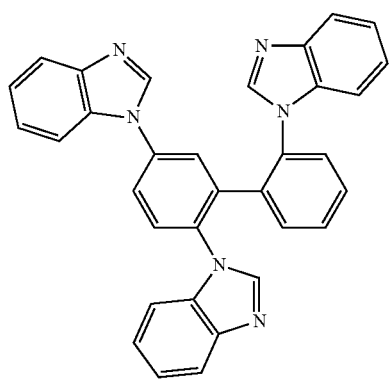
38
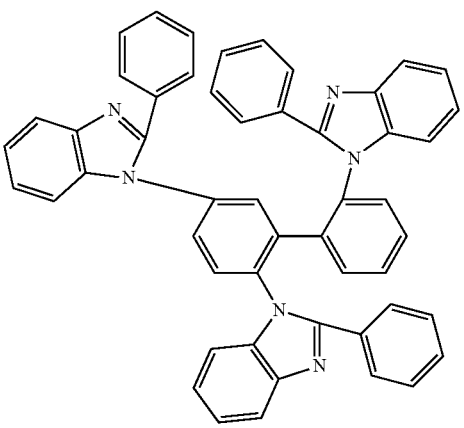

39
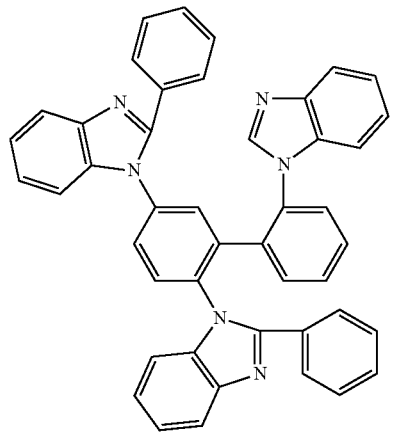
40
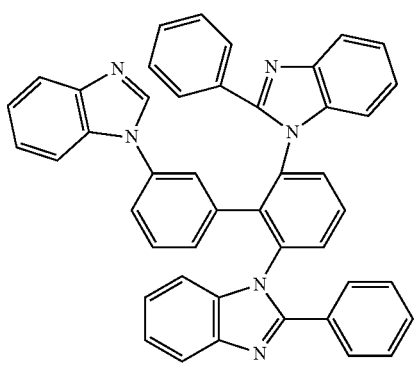
41
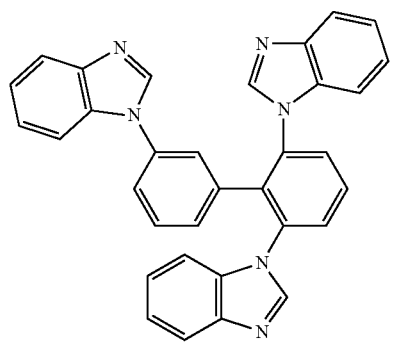
42
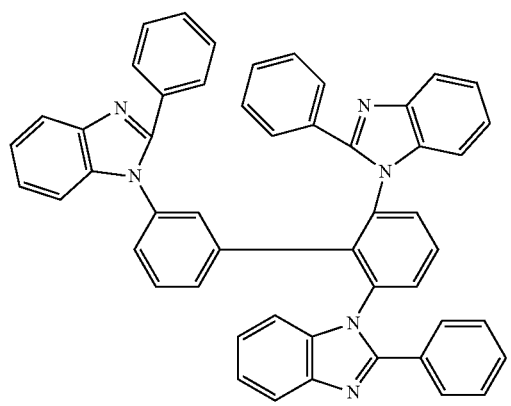
43
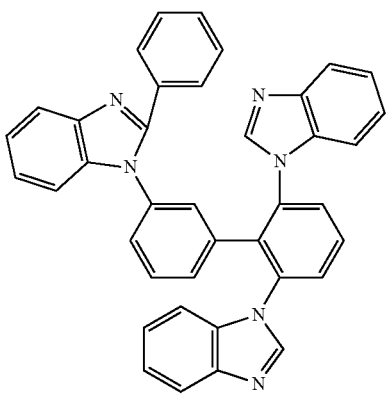
44
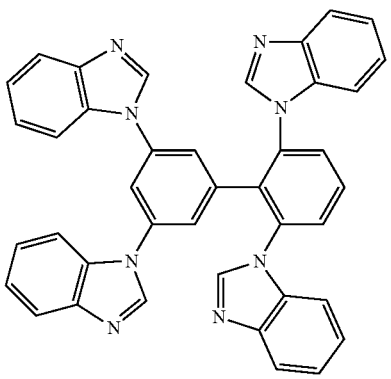
45
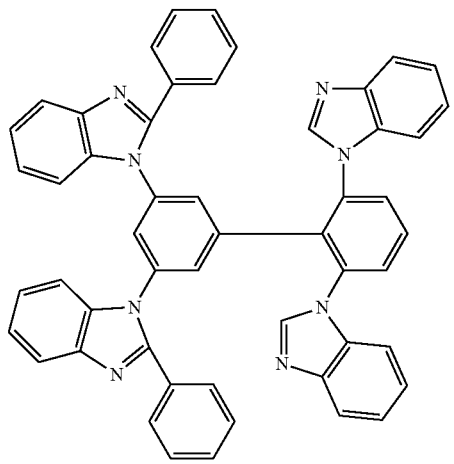
46
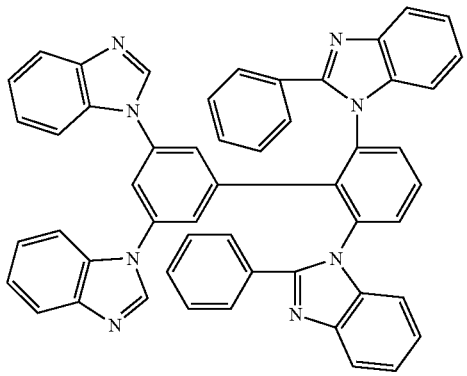

47
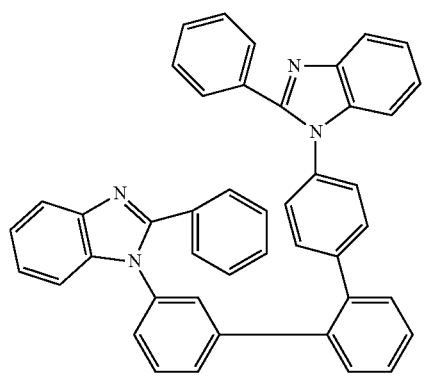
48
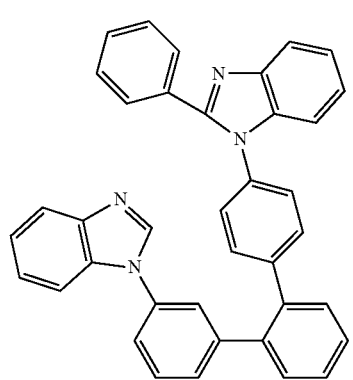
49
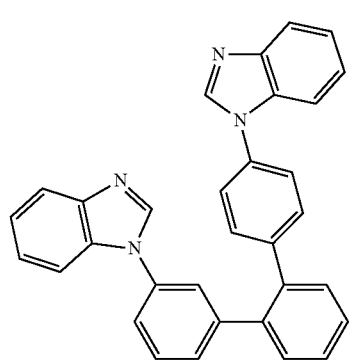
50
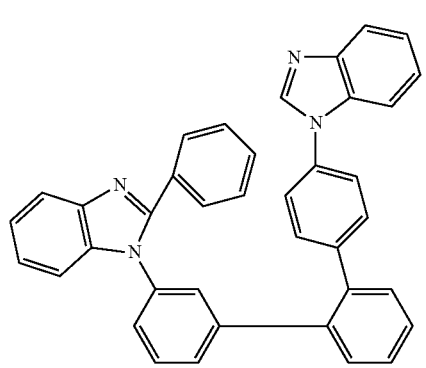
51
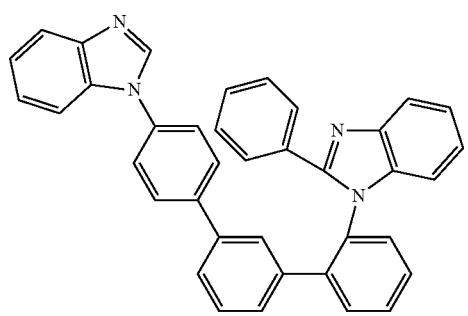
52
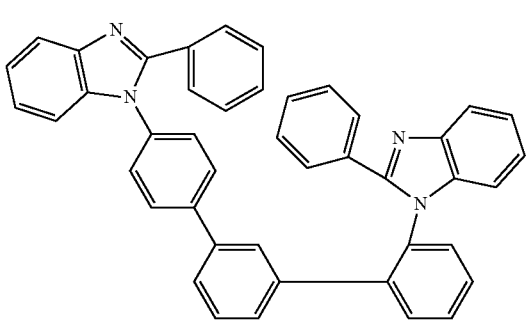
53
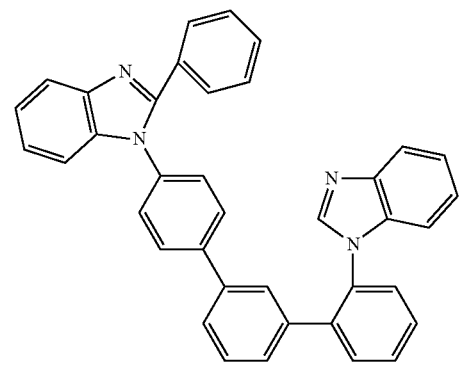
54
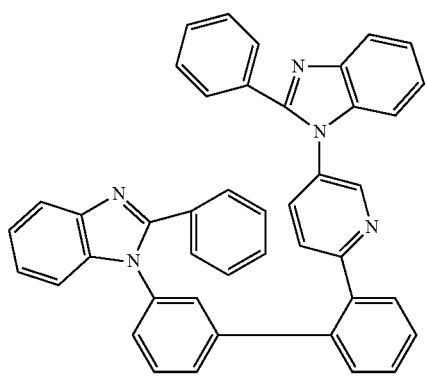

-continued
55
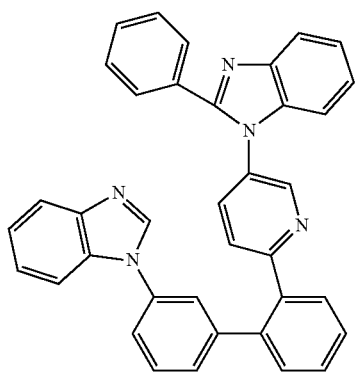
56
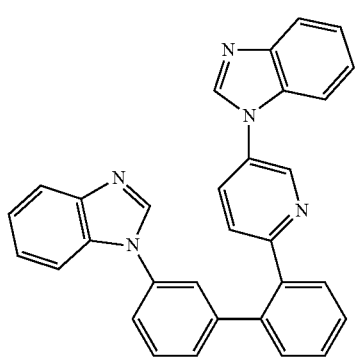
57
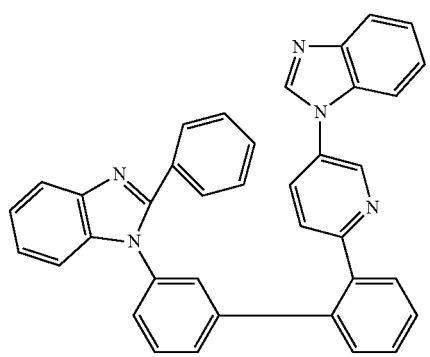
58
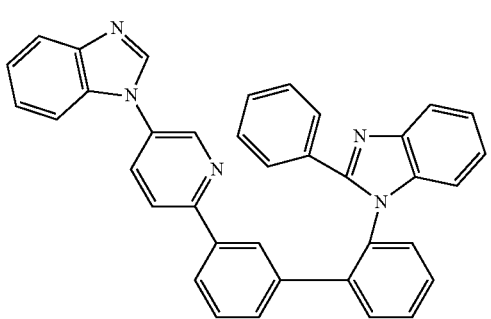
-continued
59
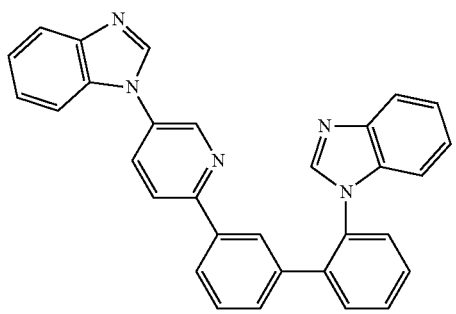
60
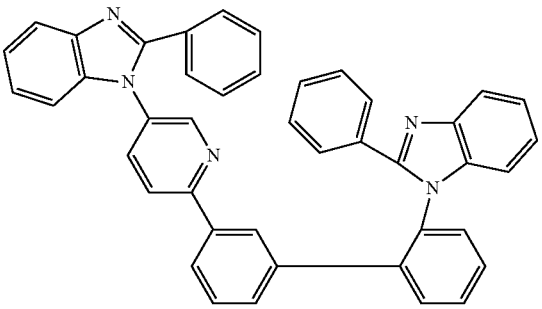
61
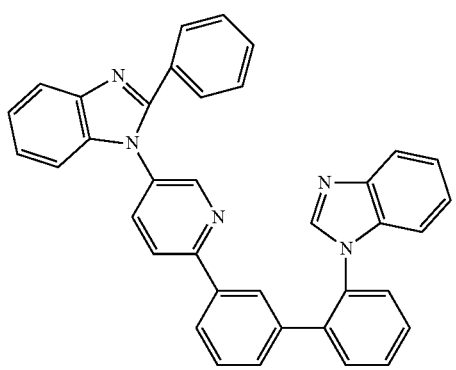
62
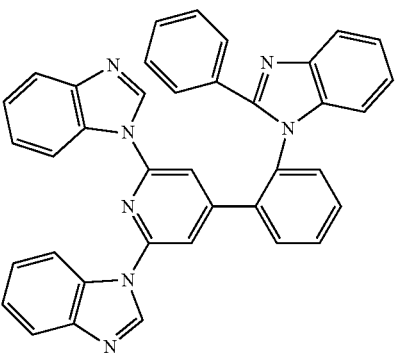

63
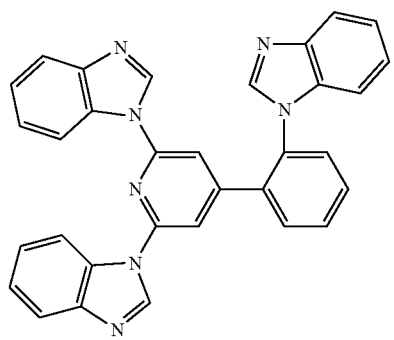
64
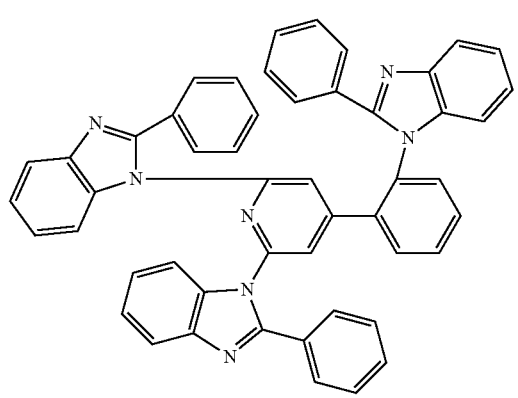
65
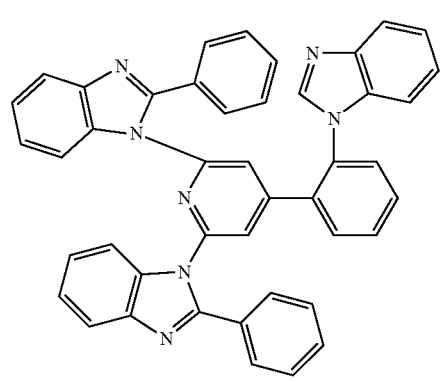
66
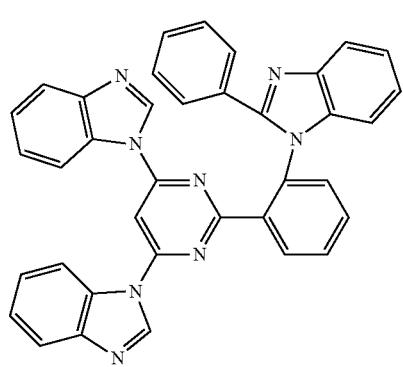
67
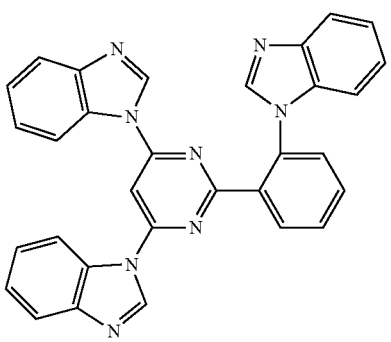
68
69
70
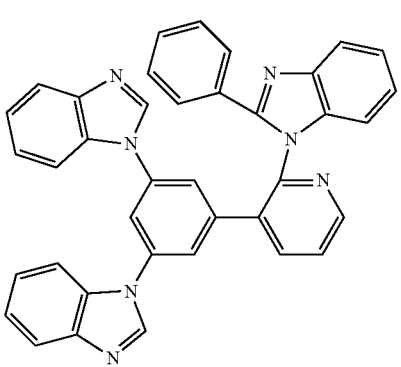

71
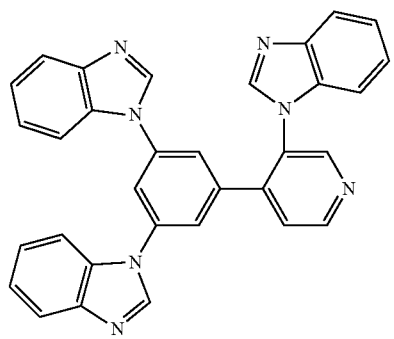
72
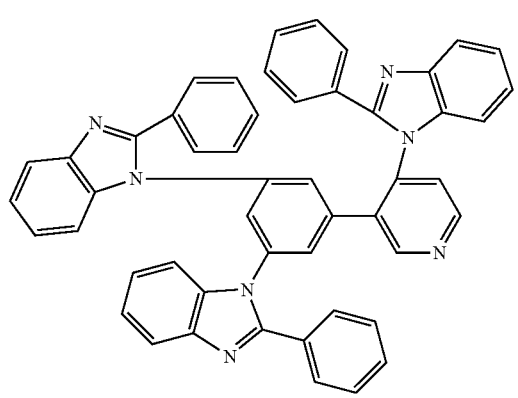
73
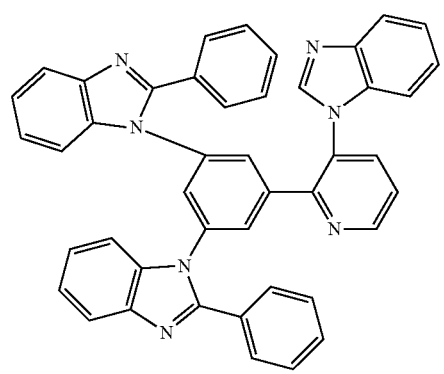
74
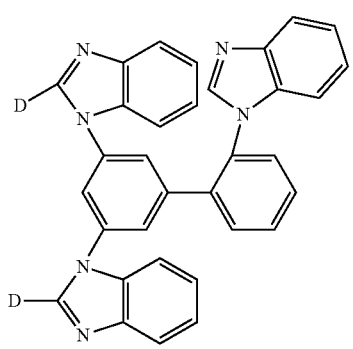
75
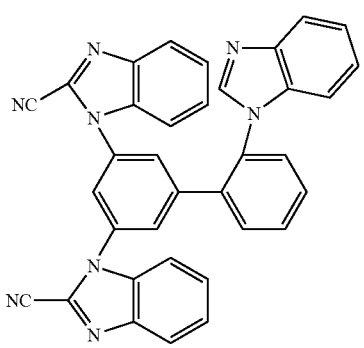
76
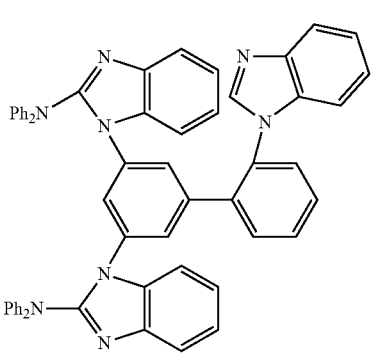
77
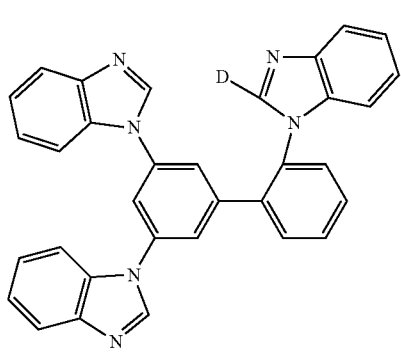
78
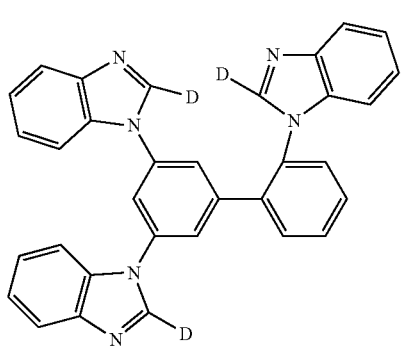

-continued

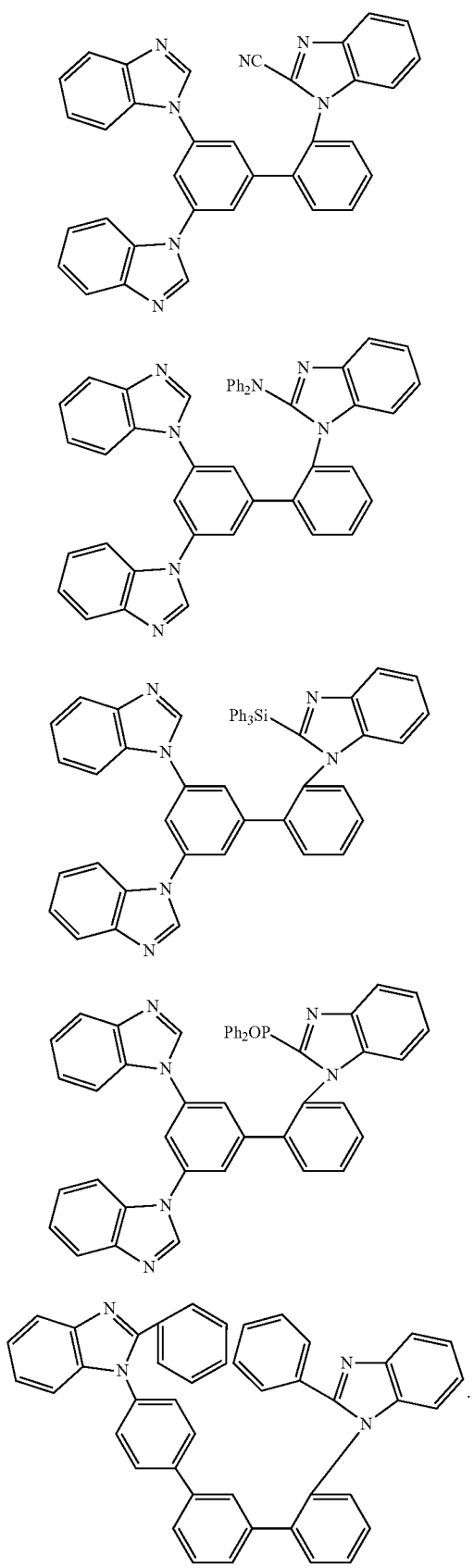

In the organic electroluminescence device 10 of an embodiment illustrated in FIGS. 1 to 4, the emission layer EML may include a host and a dopant, and the emission layer EML may include the polycyclic compound represented by Formula 1 as a host material. However, embodiments are not limited thereto. For example, the electron transport region ETR may include the polycyclic compound represented by Formula 1 as a host material.

The polycyclic compound of an embodiment may be a thermally activated delayed fluorescence host, or a phosphorescence host. The emission layer EML including the polycyclic compound of an embodiment may emit phosphorescence or thermally activated delayed fluorescence. For example, the emission layer EML may emit thermally activated delayed fluorescence.

The polycyclic compound of an embodiment may have a lowest triplet excitation energy level (T1 level) of about 2.8 eV or more which is relatively high. This is a lowest triplet excitation energy level suitable to be applied as a host material of the emission layer EML of the organic electroluminescence device which emits thermally activated delayed fluorescence.

In some embodiments, the polycyclic compound of an embodiment includes a benzimidazole group at the ortho-position of the aromatic 6-membered ring, and thus a twist may occur between the two aromatic 6-membered rings. Accordingly, the polycyclic compound of an embodiment may have a high lowest triplet excitation energy level.

Therefore, the organic electroluminescence device of an embodiment may include the polycyclic compound of the present disclosure as a blue phosphorescence host or a thermally activated delayed fluorescence host to exhibit high efficiency, long service life, and low voltage characteristics.

The emission layer EML may include one, two, or more of the polycyclic compounds of Compound Group 1 as described above.

The emission layer EML in the organic electroluminescence device 10 of an embodiment may further include any suitable materials, which are generally available in the art, as a host material in addition to the polycyclic compound of an embodiment as described above. For example, the emission layer EML may include, as a host material, at least one selected from among bis[2-(diphenylphosphino)phenyl] ether oxide (DPEPO), 4,4'-Bis(carbazol-9-yl)biphenyl (CBP), 1,3-bis(carbazol-9-yl)benzene (mCP), 2,8-Bis(diphenylphosphoryl)dibenzo[b,d]furan (PPF), 4,4',4''-Tris (carbazol-9-yl)-triphenylamine (TCTA), and 1,3,5-tris(1-phenyl-1H-benzo[d]imidazole-2-yl)benzene (TPBi). However, embodiments are not limited thereto, for example, tris(8-hydroxyquinolino)aluminum (Alq₃), poly(N-vinylcarbazole) (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethylbiphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO3), octaphenylcyclotetra siloxane (DPSiO4), etc. may be used as a host material.

The emission layer EML of an embodiment may employ, without limitation, any suitable dopant material generally available in the art. In an embodiment, the emission layer EML may further include, as a dopant material, styryl derivatives (e.g., 1,4-bis[2-(3-N-ethylcarbazoryl)vinyl]benzene (BCzVB), 4-(di-p-tolylamino)-4'-[(di-p-tolylamino) styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene), etc.

Further, the emission layer EML may include any suitable phosphorescence dopant material generally available in the art. For example, a metal complex including iridium (Ir), platinum (Pt), palladium (Pd), osmium (Os), aurum (Au), titanium (Ti), zirconium (Zr), hafnium (Hf), europium (Eu), terbium (Tb), or thulium (Tm) may be used as a phosphorescence dopant. In some embodiments, iridium(III) bis(4, 6-difluorophenylpyridinato-N,C2') (Flrpic), Bis(2,4-difluorophenylpyridinato) (Flr6), or platinum octaethyl porphyrin (PtOEP) may be used as a phosphorescence dopant. However, embodiments are not limited thereto.

In the organic electroluminescence device 10 of an embodiment shown in FIGS. 1 to 4, the electron transport region ETR is provided on the emission layer EML. The electron transport region ETR may include, but is not limited to, at least one of the hole blocking layer HBL, the electron transport layer ETL, or the electron injection layer EIL.

The electron transport region ETR may have a multilayer structure having a single layer formed of a single material, a single layer formed of materials different from each other, or a plurality of layers formed of materials different from each other.

The electron transport region ETR may include the polycyclic compound represented by Formula 1 as described above. In some embodiments, the polycyclic compound of an embodiment may be included in a layer which is in contact with the emission layer EML among a plurality of layers as described above. For example, the polycyclic compound of an embodiment may be included in the electron transport layer ETL. However, embodiments are not limited thereto. In addition to the electron transport layer ETL, the hole blocking layer HBL, or the electron injection layer EIL may include the polycyclic compound of an embodiment. Because, with respect to the polycyclic compound, the same descriptions of the polycyclic compound included in the emission layer EML may be applied, duplicative descriptions thereof will not be repeated.

The polycyclic compound of an embodiment may include two aromatic 6-membered rings and a benzimidazole group which is substituted at the two aromatic 6-membered rings (e.g., a benzimidazole group which is substituted at each of the two aromatic 6-membered rings), and thereby having excellent electron transporting characteristics.

In addition, the benzimidazole group is substituted at the ortho-position with respect to a single bond which links the two aromatic 6-membered rings, and, as a result, a twist may occur between the two aromatic 6-membered rings. Accordingly, the benzimidazole group may have a high lowest triplet excitation energy level. For example, by having the benzimidazole group substituted at the ortho-position with respect to a single bond which links the two aromatic 6-membered rings, the two aromatic 6-membered rings may be twisted with respect to one another such that the two aromatic 6-membered rings do not lie in a same plane, thereby increasing the lowest triplet excitation energy level of the polycyclic compound.

Therefore, the organic electroluminescence device 10 of an embodiment may include the compound of an embodiment in the electron transport region ETR, and thereby achieving high efficiency and long service life. For example, the organic electroluminescence device 10 of an embodiment may include the compound of an embodiment in the hole blocking layer HBL, and thereby achieving high efficiency and long service life. However, embodiments are not limited thereto, a plurality of layers in the electron transport region ETR may include the polycyclic compound of an embodiment without limitation.

For example, the electron transport region HTR may have a single layer structure of an electron injection layer EIL or an electron transport layer ETL, or a single layer structure formed of electron injection materials or electron transport materials. In addition, the electron transport region ETR may have a single layer structure formed of materials different from each other, or a structure of electron transport layer ETL/electron injection layer EIL, hole blocking layer HBL/electron transport layer ETL/electron injection layer (EIL) which are sequentially laminated from the emission layer EML, but embodiments are not limited thereto. The electron transport region ETR may have a thickness, for example, from about 1,000 Å to about 1,500 Å. The plurality of layers in the electron transport region ETR may include the polycyclic compound of an embodiment.

The electron transport region ETR may be formed by using various suitable methods such as a vacuum deposition method, a spin coating method, a casting method, a Langmuir-Blodgett (LB) method, an inkjet printing method, a laser printing method, and/or a laser induced thermal imaging (LITI) method.

If the electron transport region ETR includes the electron transport layer ETL, the electron transport region ETR may include an anthracene-based compound. However, embodiments are not limited thereto, and the electron transport region may include, for example, tris(8-hydroxyquinolinato) aluminum (Alq3), 1,3,5-tri[(3-pyridyl)-phen-3-yl]benzene, 2,4,6-tris(3'-(pyridin-3-yl)biphenyl-3-yl)-1,3,5-triazine,2-(4-(N-phenylbenzoimidazolyl-1-ylphenyl)-9,10-dinaphthylanthracene, 1,3,5-Tri(1-phenyl-1H-benzo[d]imidazol-2-yl) phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2, 4-triazole (TAZ), 4-(naphthalen-1-yl)-3,5-diphenyl-4H-1,2, 4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate) (Bebq2), 9,10-di (naphthalene-2-yl)anthracene (ADN), 1,3-Bis[3,5-di(pyridin-3-yl)phenyl]benzene (BmPyPhB), or a mixture thereof. The thickness of the electron transport layers ETL may be from about 100 Å to about 1,000 Å, for example, from about 150 Å to about 500 Å. If the thickness of the electron transport layers ETL satisfies the above-described range, suitable or satisfactory electron transport characteristics may be achieved without substantially increasing in driving voltage.

When the electron transport region ETR includes the electron injection layer EIL, the electron transport region ETR may be formed using metal halides such as LiF, NaCl, CsF, RbCl, RbI, and CuI, lanthanum metals such as Yb, metal oxides such as $Li_2O$ and BaO, Lithium quinolate (8-hydroxyl-Lithium quinolate), etc., but embodiments are not limited thereto. The electron injection layer EIL may be also formed of a mixture of an electron transport material and an organo metal salt. The organo metal salt may be a material having an energy band gap of about 4 eV or more. For example, the organo metal salt may include metal acetate, metal benzoate, metal acetoacetate, metal acetylacetonate or metal stearate. The electron injection layers EIL may have a thickness from about 1 Å to about 100 Å, and from about 3 Å to about 90 Å. If the thickness of the electron injection layers EIL satisfies the above-described range, suitable or satisfactory electron injection characteristics may be achieved without substantially increasing in driving voltage.

As described above, the electron transport region ETR may include the hole blocking layer HBL. The hole blocking layer HBL may include, for example, at least one of 2,9-dimethyl-4,7-diphenyl-1,10-phenanthroline (BCP), or 4,7-diphenyl-1,10-phenanthroline (Bphen), but is not limited thereto.

The second electrode EL2 may be on the electron transport region HTR. The second electrode EL2 may be a common electrode or acathode. The second electrode EL2 may be a transmissive electrode, a transflective electrode, or a reflective electrode. When the second electrode EL2 is the transmissive electrode, the second electrode EL2 may be formed of transparent metal oxides, for example, indium tin oxide (ITO), indium zinc oxide (IZO), zinc oxide (ZnO), indium tin zinc oxide (ITZO), etc.

When the second electrode EL2 is the transflective electrode or the reflective electrode, the second electrode EL2 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) including the same. In some embodiments, the first electrode EL1 may have a multi-layered structure including a reflective layer or transflective layer and a transparent conductive layer formed of indium tin oxide (ITO), indium zinc oxide (IZO), zinc oxide (ZnO), and/or indium tin zinc oxide (ITZO).

In some embodiments, the second electrode EL may be coupled to an auxiliary electrode. When the second electrode EL2 is coupled to the auxiliary electrode, resistance of the second electrode EL2 may be decreased.

In some embodiments, a capping layer CPL may be further on the second electrode EL2 of the organic electroluminescence device 10 of an embodiment. The capping layer CPL may include, for example, α-NPD, NPB, TPD, m-MTDATA, Alq3, CuPc, N4,N4,N4',N4'-tetra (biphenyl-4-yl) biphenyl-4,4'-diamine (TPD15), 4,4',4"-Tris (carbazol sol-9-yl) triphenylamine (TCTA), etc.

In the organic electroluminescence device 10, as a voltage is applied to the first electrode EL1 and the second electrode EL2, respectively, the holes injected from the first electrode EL1 are moved through the hole transport region HTR to the emission layer EML, and the electrons injected from the second electrode EL2 are moved through the electron transport region ETR to the emission layer EML. The electrons and holes are recombined in the emission layer EML to generate excitons and emit light when the excitons return to a ground state from an excited state.

In the organic electroluminescence device 10, as a voltage is applied to the first electrode EL1 and the second electrode EL2, respectively, the holes injected from the first electrode EL1 are moved through the hole transport region HTR to the emission layer EML, and the electrons injected from the second electrode EL2 are moved through the electron transport region ETR to the emission layer EML. The electrons and holes are recombined in the emission layer EML to generate excitons and emit light when the excitons return (e.g., transition) to a ground state from an excited state.

The polycyclic compound according to an embodiment of the present disclosure includes the benzimidazole group which is substituted at the ortho-position with respect to a single bond which links the two aromatic 6-membered rings, and thereby a twist may occur between the two aromatic 6-membered rings (e.g., the two aromatic 6-membered rings may be twisted with respect to one another such that the two aromatic 6-membered rings do not lie in a same plane).

Accordingly, the polycyclic compound of an embodiment may have a lowest triplet excitation energy level (T1 level) of about 2.8 eV or more (e.g., 2.8 eV to 3.5 eV) which is relatively high, and excellent electron transport characteristics.

The polycyclic compound of an embodiment may have a lowest triplet excitation energy level (T1 level) of about 2.8 eV or more (e.g., 2.8 eV to 3.5 eV), which is relatively high. Therefore, the organic electroluminescence device 10 of an embodiment may use the polycyclic compound of an embodiment as a host to emit blue phosphorescence or thermally activated delayed fluorescence. Furthermore, when the polycyclic compound of an embodiment is included in the electron transport region ETR of the organic electroluminescence device 10, the polycyclic compound of an embodiment may exhibit high electron mobility to serve as excellent electron transport.

Accordingly, the organic electroluminescence device 10 of an embodiment may include the polycyclic compound containing two aromatic 6-membered rings and a benzimidazole group which is substituted at the ortho-position of any one selected from among the two aromatic 6-membered rings, and thereby have high efficiency and long service life characteristics.

Hereinafter, a polycyclic compound according to an embodiment of the present disclosure and an organic electroluminescence device of an embodiment of the present disclosure will be explained in more detail with reference to examples and comparative examples. In addition, the examples below are exemplified for assisting the understanding of the present disclosure, and the scope of the present disclosure is not limited thereto.

1. Synthetic Examples

A polycyclic compound according to an embodiment of the present disclosure may be synthesized, for example, as follows. However, in the following descriptions, a synthetic method of the polycyclic compound is provided as an example, but the synthetic method according to an embodiment of the present disclosure is not limited to the following examples.

A. Synthesis of Compound 1

Reaction Formula 1-1

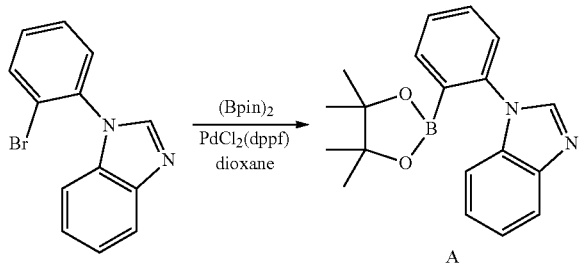

(1) Synthesis of Intermediate Compound A

In an argon atmosphere, in a 100 mL three-neck flask, 1-(2-bromophenyl)-1H-Benzimidazole*(9.35 g, 34.2 mmol), bis(pinacolato)diboron (13.04 g, 51.4 mmol), PdCl$_2$(dppf) (1.25 g, 1.71 mmol) and potassium acetate (KOAc)

(10.1 g, 103 mmol) were added and dissolved in dioxane (171 mL), and heated and stirred at 120° C. for 24 hours. After air cooling, water was added to fractionate an organic layer, and then solvents were removed by distillation. The resulting crude product was purified by a silica gel column chromatography to obtain Compound A which is a white solid (1.65 g, yield: 15%). By FAB-MS measurement of the obtained purified product, it was identified that the molecular weight of Compound A was 320 Thus, it was identified that Intermediate A, a target product was obtained.

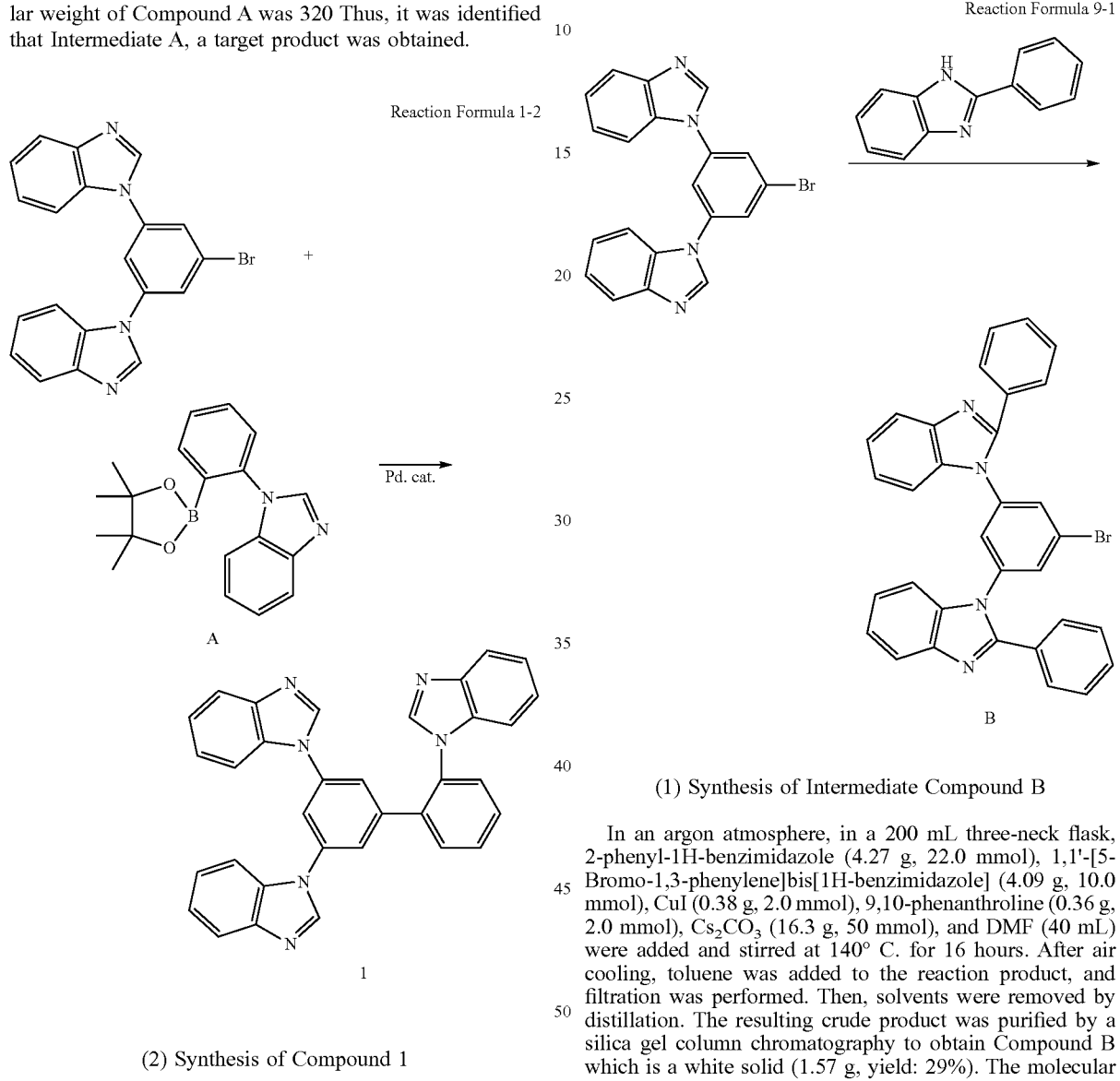

(2) Synthesis of Compound 1

In an argon atmosphere, in a 100 mL three-neck flask, 1,1'-[5-Bromo-1,3-phenylene]bis[1H-benzimidazole] (2.00 g, 5.1 mmol), Intermediate Compound A (1.65 g, 5.1 mmol), Pd(OAc)$_2$ (0.058 g, 0.26 mmol), PPh$_3$ (0.27 g, 1.0 mmol), K2CO3 (3.27 g, 15.4 mmol), toluene (20 mL), ethanol (6 mL), and water (2 mL) were added and heated and stirred at 100° C. for 4 hours. After air cooling, water was added to fractionate an organic layer, and then solvents were removed by distillation. The resulting crude product was purified by a silica gel column chromatography to obtain Compound 1 which is a white solid (1.52 g, yield: 59%). By FAB-MS measurement of the obtained purified product, it was identified that the molecular weight of Compound 1 was 502 and δ (a chemical shift value) of Compound 1 measured in 1H-NMR (CDCl$_3$) measurement was [7.98 (1H), 7.86-7.82 (3H), 7.74-7.64 (6H), 7.56 (1H), 7.45 (1H), 7.36-7.34 (3H), 7.32-7.26 (5H), 7.20 (2H)]. Thus, it was identified that Compound 1, a target product was obtained.

B. Synthesis of Compound 9

(1) Synthesis of Intermediate Compound B

In an argon atmosphere, in a 200 mL three-neck flask, 2-phenyl-1H-benzimidazole (4.27 g, 22.0 mmol), 1,1'-[5-Bromo-1,3-phenylene]bis[1H-benzimidazole] (4.09 g, 10.0 mmol), CuI (0.38 g, 2.0 mmol), 9,10-phenanthroline (0.36 g, 2.0 mmol), Cs$_2$CO$_3$ (16.3 g, 50 mmol), and DMF (40 mL) were added and stirred at 140° C. for 16 hours. After air cooling, toluene was added to the reaction product, and filtration was performed. Then, solvents were removed by distillation. The resulting crude product was purified by a silica gel column chromatography to obtain Compound B which is a white solid (1.57 g, yield: 29%). The molecular weight of Compound B measured by FAB-MS measurement was 541.

Reaction Formula 9-2

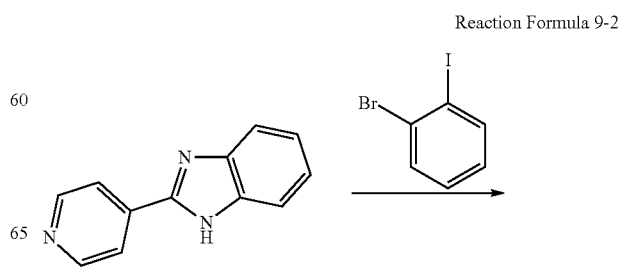

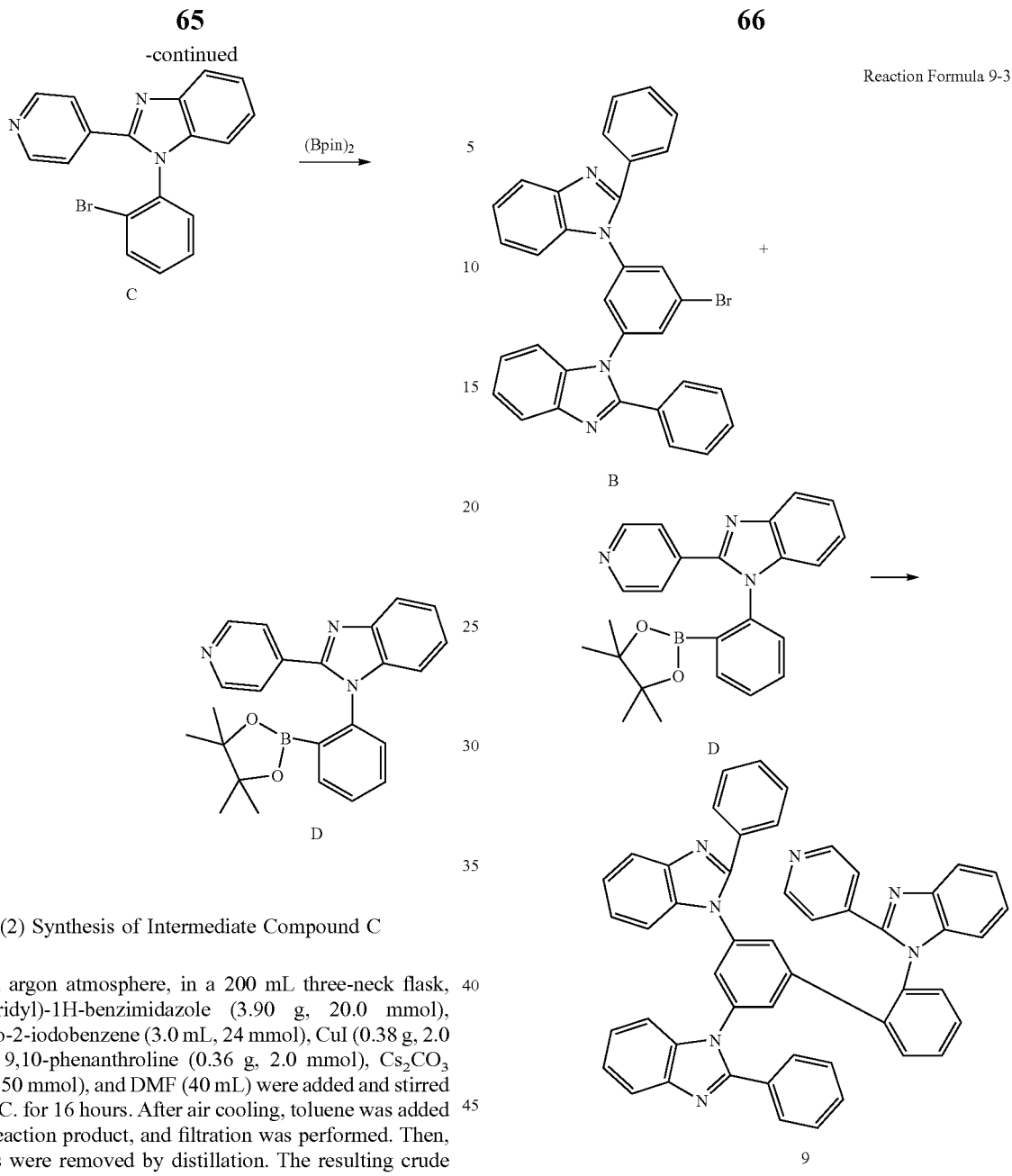

Reaction Formula 9-3

(2) Synthesis of Intermediate Compound C

In an argon atmosphere, in a 200 mL three-neck flask, 2-(4-pyridyl)-1H-benzimidazole (3.90 g, 20.0 mmol), 1-bromo-2-iodobenzene (3.0 mL, 24 mmol), CuI (0.38 g, 2.0 mmol), 9,10-phenanthroline (0.36 g, 2.0 mmol), $Cs_2CO_3$ (16.3 g, 50 mmol), and DMF (40 mL) were added and stirred at 140° C. for 16 hours. After air cooling, toluene was added to the reaction product, and filtration was performed. Then, solvents were removed by distillation. The resulting crude product was purified by a silica gel column chromatography to obtain Compound C which is a white solid (2.73 g, yield: 39%). The molecular weight of Compound C measured by FAB-MS measurement was 350.

(3) Synthesis of Intermediate Compound D

In an argon atmosphere, in a 200 mL three-neck flask, Compound C (2.66 g, 7.6 mmol), bis(pinacolato)diboron (2.89 g, 11.4 mmol), $PdCl_2(dppf)$ (0.31 g, 0.38 mmol), KOAc (2.24 g, 22.8 mmol), and dioxane (40 mL) were added and stirred at 120° C. for 24 hours. After air cooling, water was added to fractionate an organic layer, and then solvents were removed by distillation. The resulting crude product was purified by a silica gel column chromatography to obtain Compound D which is a white solid (0.97 g, yield: 32%). The molecular weight of Compound D measured by FAB-MS measurement was 397.

(4) Synthesis of Compound 9

In an argon atmosphere, in a 100 mL three-neck flask, Compound B (1.30 g, 2.4 mmol), Compound D (0.96 g, 2.4 mmol), $Pd(OAc)_2$ (0.027 g, 0.12 mmol), Xantphos (0.14 g, 0.24 mmol), $K_3PO_4$ (0.98 g, 7.2 mmol), toluene (12 mL), ethanol (4.0 mL), and water (1.0 mL) were added and heated and stirred at 100° C. for 4 hours. After air cooling, water was added to fractionate an organic layer, and then solvents were removed by distillation. The resulting crude product was purified by a silica gel column chromatography to obtain Compound 9 which is a white solid (1.12 g, yield: 64%). By FAB-MS measurement of the obtained purified product, it was identified that the molecular weight of Compound 9 was 731 and δ (a chemical shift value) of Compound 9 measured in 1H-NMR ($CDCl_3$) measurement was [8.78(2H), 8.58-8.54(3H), 8.28(4H), 8.09(2H), 7.99

(2H), 7.83-7.75(5H), 7.66(1H), 7.55-7.48(11H), 7.28(3H)]. Thus, it was identified that Compound 9, a target product was obtained.

C. Synthesis of Compound 27

Reaction Formula 27

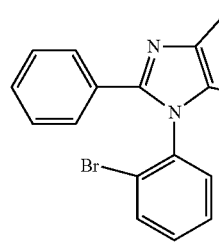

→

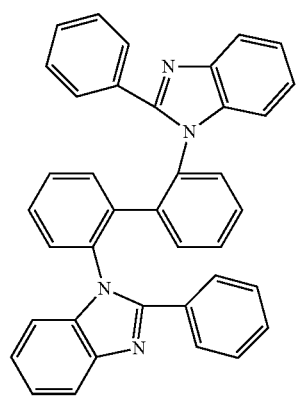

(1) Synthesis of Compound 27

In an argon atmosphere, in a 100 mL three-neck flask, 1-(2-bromophenyl)-2-phenyl-1H-Benzimidazole (3.49 g, 10.0 mmol), NMP (20 mL), and Cu(I) thiophene-2-carboxylate (4.77 g, 25.0 mmol) were added and stirred at 180° C. for 24 hours. After air cooling, the reactant was filtered by adding toluene, and then the solvent was distilled. The resulting crude product was purified by a silica gel column chromatography to obtain Compound 27 which is a white solid (0.70 g, yield: 26%). By FAB-MS measurement of the obtained purified product, it was identified that the molecular weight of Compound 27 was 538 and δ (a chemical shift value) of Compound 1 measured in 1H-NMR (CDCl$_3$) measurement was [8.56(2H), 8.28(4H), 7.83-7.75(6H), 7.66 (2H), 7.55-7.48(10H), 7.28(2H)]. Thus, it was identified that Compound 27, a target product was obtained.

2. Evaluation of Energy Level of Compound

Table 1 below shows the lowest excitation triplet energy level (T1 level, eV) of Example Compound 1, and Comparative Example Compound c2 and c3. In Table 1, T1 value (eV) was calculated using density functional theory (DFT) utilizing the B3LYP hybrid functional and the 6-31G(d) basis set using a Gaussian 09 program, available from Gaussian Inc.

Example Compound

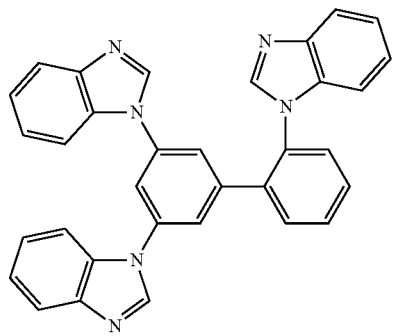

1

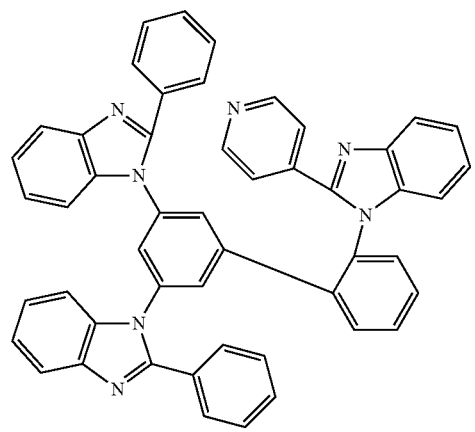

9

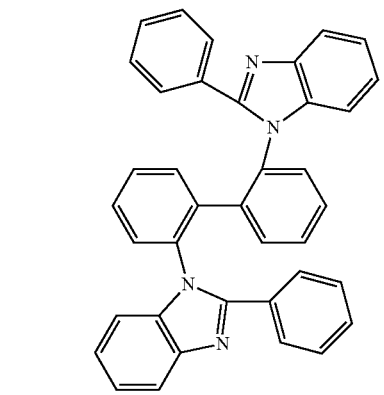

27

Comparative Example Compound c1
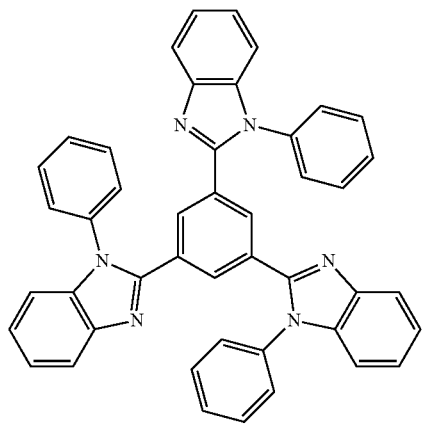

c2
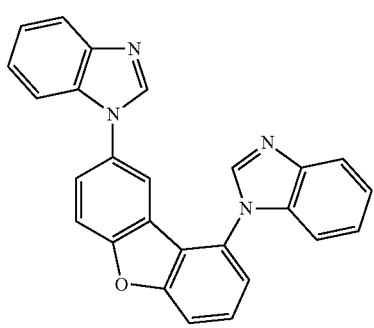

c3
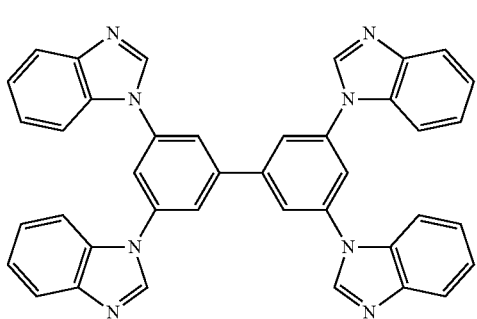

c4
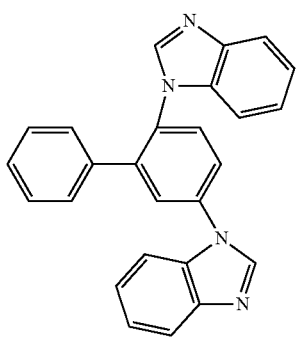

TABLE 1

| Host | T1 [eV] |
|---|---|
| Example Compound 1 | 3.27 |
| Comparative Example Compound c1 | 3.01 |
| Comparative Example Compound c2 | 3.09 |
| Comparative Example Compound c3 | 3.12 |

Referring to the results of Table 1 above, the lowest excitation triplet energy level (T1) of Example Compound 1 is 3.27 eV, which is higher than the lowest excitation triplet energy levels (T1) of Comparative Example Compounds c1 to c3, which are 3.01 eV, 3.09 eV, and 3.12 eV, respectively.

3. Manufacture and Evaluation of Organic Electroluminescence Device Including Polycyclic Compound Manufactures 1 and 3 of organic electroluminescence devices included the polycyclic compound of the present disclosure as a host material, and a phosphorescence dopant and a TADF dopant, respectively. Manufactures 2 and 4 of organic electroluminescence devices included the polycyclic compound of the present disclosure as a hole transport region material, and a phosphorescence dopant and a TADF dopant, respectively.

A material of each layer used in Manufactures 1 to 4 of the organic electroluminescence devices is as follows.

Functional Layer Compound

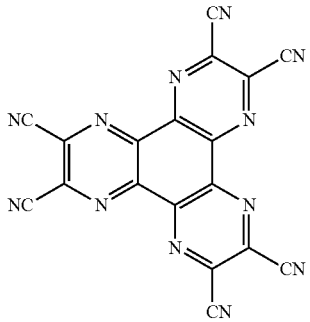

HAT-CN

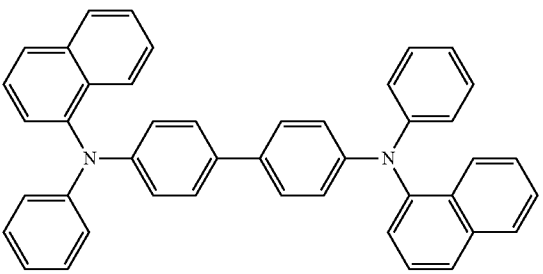

NPB

-continued

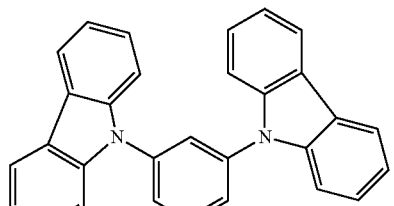

mCP

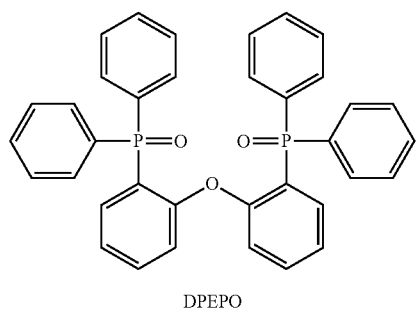

DPEPO

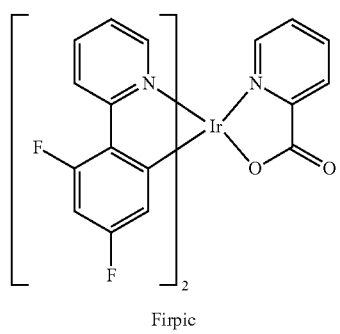

Firpic

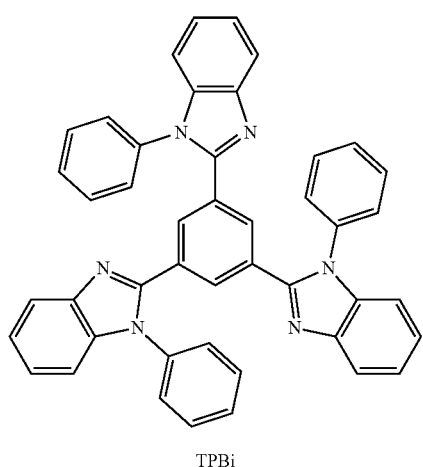

TPBi

-continued

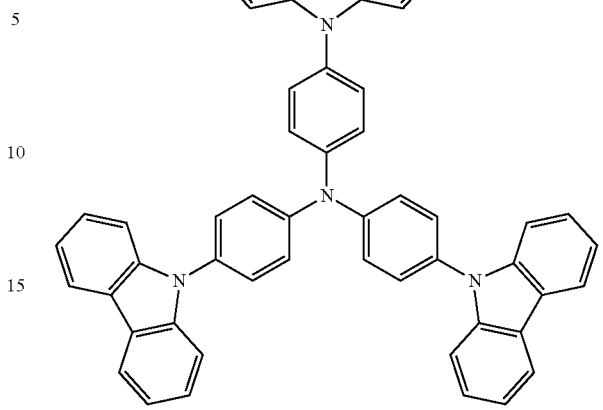

TCTA

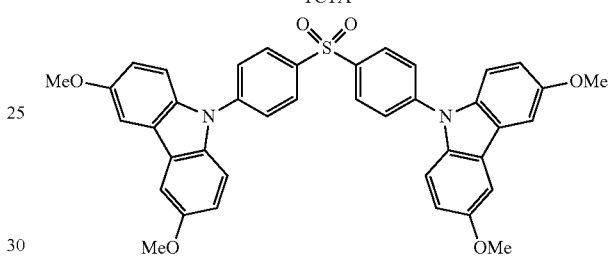

DMOC-DPS

To evaluate properties of the manufactured organic electroluminescence devices, the maximum luminous efficiency and the luminance half-life were measured and the results are shown in Tables 2 to 5. The luminance half-life is represented with respect to the time taken to reduce the luminance to about 50% of an initial luminance of 100 cd/m$^2$. In Tables 2 to 5, the maximum luminous efficiency and the luminance half-life are evaluated with respect to the maximum luminous efficiency and the luminance half-life (100%), in which Comparative Example Compound c1 is used as an emission layer material or the electron transport region material.

Manufacture 1 of Organic Electroluminescence Device

An organic electroluminescence device of an embodiment including the polycyclic compound of an embodiment in the emission layer was manufactured as follows. Compounds 1, 9, and 27 as described above were used as a host material of the emission layer to manufacture the organic electroluminescence devices of Examples 1 to 3, respectively. Compounds c1 to c4 as described above were used as a host material of the emission layer to manufacture the organic electroluminescence devices of Comparative Examples 1 to 4, respectively. A phosphorescence material was used as a luminous material.

After ITO having a thickness of about 150 nm was patterned on a glass substrate, a first electrode was formed. An electrode substrate was washed with pure water and cleansed utilizing ultrasonic waves (e.g., sonication) for about 20 minutes, and then treated with ozone for about 10 minutes by irradiation with ultraviolet rays. After cleansing, the electrode substrate was introduced to a vacuum chamber to laminate organic materials as follows.

1,4,5,8,9,12-Hexaazatriphenylenehexacarbonitrile (HAT-CN) was deposited on the first electrode to form a hole injection layer having a thickness of about 10 nm, and then N,N'-di(naphthalene-1-yl)-N,N'-diphenyl-benzidine (NPB) was deposited thereon to form a hole transport layer having a thickness of about 40 nm. Then, 1,3-Bis(N-carbazolyl) benzene (mCP) was deposited thereon to form an electron blocking layer having a thickness of about 10 nm.

On the electron blocking layer, an emission layer, in which Firpic was doped by about 8% to Example Compounds or Comparative Example Compounds of the present disclosure, was formed to a thickness of about 20 nm. Specifically, the emission layer was deposited by doping Firpic to Compounds 1, 9, and 27 in Examples 1 to 3, respectively, and was deposited by doping Firpic to Compounds c1 to c4 in Comparative Examples 1 to 4, respectively.

On the emission layer, bis[2-(diphenylphosphino)phenyl] ether oxide (DPEPO) was deposited to form a hole blocking layer having a thickness of about 10 nm, and then 2,2',2"-(1,3,5-Benzinetriyl)-tris(1-phenyl-1-H-benzimidazole) (TPBi) was deposited thereon to form an electron transport layer having a thickness of about 30 nm. Then, 8-Hydroxyquinolinolato-lithium (Liq) was deposited thereon to form an electron injection layer having a thickness of about 2 nm. Then, aluminum (Al) was deposited thereon to form a second electrode having a thickness of about 120 nm to manufacture an organic electroluminescence device. The manufactured organic electroluminescence devices were sealed in a nitrogen atmosphere, and the evaluation was carried out in the atmosphere at room temperature.

TABLE 2

| Examples of manufactured devices | Host | Maximum luminous Efficiency | Luminance life |
|---|---|---|---|
| Example 1 | Example Compound 1 | 130% | 110% |
| Example 2 | Example Compound 9 | 130% | 120% |
| Example 3 | Example Compound 27 | 120% | 130% |
| Comparative Example 1 | Comparative Example Compound c1 | 100% | 100% |
| Comparative Example 2 | Comparative Example Compound c2 | 105% | 90% |
| Comparative Example 3 | Comparative Example Compound c3 | 80% | 60% |
| Comparative Example 4 | Comparative Example Compound c4 | 60% | 60% |

Referring to the results of Table 2, when the polycyclic compounds according to examples of the present disclosure each was used as a host material of the emission layer of each of the organic electroluminescence devices, high efficiency and a long service life may be achieved. Specifically, it can be seen that Examples 1 to 3 exhibit high efficiency and long service life characteristics compared to Comparative Examples 1 to 4. With regard to the polycyclic compound of the present disclosure, a benzimidazole group is substituted at the ortho-position of aromatic 6-membered rings with respect to a single bond, such that a twist occurs between the two aromatic 6-membered rings which are linked by a single bond. Accordingly, the polycyclic compound of an embodiment may have a high lowest triplet excitation energy level (Ti level) of about 2.8 eV or more (e.g., 2.8 eV to 3.5 eV), and the organic electroluminescence device may include the polycyclic compound of an embodiment in the emission layer to exhibit high efficiency and long service life characteristics.

In the case of Comparative Example Compound c1, only one phenyl group is included in the center thereof, and thus the service life is reduced due to the low durability of the molecule (Comparative Example Compound c1).

In the case of Comparative Example Compound c2, a dibenzofuranyl group is formed by cross-linking two phenyl groups via an oxygen atom, and in the case of Comparative Example Compound c3, the degree of a twist of the compound is small because a substituent is not at the ortho-position. Therefore, in Comparative Examples 1 to 3, luminous efficiency and service life characteristics of the devices are reduced because a lowest excitation triplet energy level (T1 level) of a host material of the emission layer is reduced, as compared to the devices of the Examples.

In the case of Comparative Example Compound c4, a benzimidazole group is substituted at only one benzene ring of a biphenyl group, thus electron and hole transport properties are low as compared to the Example Compounds, and thereby luminous efficiency and service life are reduced.

Manufacture 2 of Organic Electroluminescence Device

An organic electroluminescence device of an embodiment including the polycyclic compound of an embodiment in the electron transport region was manufactured as follows. Each of Compounds 1, 9, and 27 as described above was used as a material of the hole blocking layer in the electron transport region to manufacture the organic electroluminescence devices of Examples 4 to 6. In Comparative Examples 5, 6, 7, and 8, each of Compounds c1, c2, c3, and c4 was used as a material of the hole blocking layer to manufacture the organic electroluminescence devices. A phosphorescence material was used as a luminous material.

From the formation of a first electrode to the formation of an electron blocking layer, the same processes as those described above (Manufacture 1 of Organic Electroluminescence Device) were carried out.

On the electron blocking layer, an emission layer, in which Firpic was doped by about 8%, was formed to a thickness of about 20 nm using DPEPO as a host material. Each of the Example Compounds and the Comparative Example Compounds was deposited on the emission layer to form a hole blocking layer having a thickness of about 10 nm. That is, with respect to the formed hole blocking layer, Compounds 1, 9, and 27 were deposited in Examples 4 to 6, respectively, and Compounds c, c2, c3, and c4 were deposited in Comparative Examples 5 to 8, respectively.

On each hole blocking layer, TPBi was deposited to form an electron transport layer having a thickness of about 30 nm, and Liq was deposited thereon to form an electron injection layer having a thickness of about 2 nm. Finally, aluminum (Al) was deposited thereon to form a second electrode having a thickness of about 120 nm to manufacture organic electroluminescence devices. The manufactured organic electroluminescence devices were sealed in a nitrogen atmosphere, and the evaluation was carried out in the atmosphere at room temperature.

TABLE 3

| Examples of manufactured devices | Hole blocking layer | Maximum luminous Efficiency | Luminance half-life |
|---|---|---|---|
| Example 4 | Example Compound 1 | 130% | 120% |
| Example 5 | Example Compound 9 | 130% | 120% |
| Example 6 | Example Compound 27 | 120% | 140% |
| Comparative Example 5 | Comparative Example Compound c1 | 100% | 100% |
| Comparative Example 6 | Comparative Example Compound c2 | 105% | 90% |

TABLE 3-continued

| Examples of manufactured devices | Hole blocking layer | Maximum luminous Efficiency | Luminance half-life |
|---|---|---|---|
| Comparative Example 7 | Comparative Example Compound c3 | 80% | 60% |
| Comparative Example 8 | Comparative Example Compound c4 | 60% | 80% |

Referring to the results of Table 3, when the polycyclic compounds according to examples of the present disclosure each was used as a material of the electron transport region of each of the organic electroluminescence devices, high efficiency and a long service life may be achieved. Specifically, it can be seen that Examples 4 to 6 exhibit high efficiency and long service life characteristics as compared to Comparative Examples 5 to 8. With regard to the polycyclic compound of the present disclosure, a benzimidazole group is substituted at the ortho-position of aromatic 6-membered rings with respect to a single bond, such that a twist occurs between the two aromatic 6-membered rings which are linked by a single bond. Accordingly, the polycyclic compound of an embodiment may have excellent electron mobility, and the organic electroluminescence device includes the polycyclic compound of an embodiment in the electron transport region, thereby exhibiting high efficiency and long service life characteristics.

In the case of Comparative Example Compound c1, only one phenyl group is included in the center thereof, and thus the service life is reduced due to the low durability of the molecule (Comparative Example Compound c1).

In the case of Comparative Example Compound c2, two phenyl groups are cross-linked, and in the case of Comparative Example Compound c3, the degree of a twist of the compound is small because a substituent is not at the ortho-position.

Therefore, in Comparative Examples 1 to 3, luminous efficiency and service life characteristics of the devices are reduced by reducing the electron mobility of a material of the hole blocking layer, as compared to the devices of the Examples.

In the case of Comparative Example Compound c4, a benzimidazole group is substituted at only one benzene ring of a biphenyl group, thus electron and hole transport properties are low compared to Example Compounds, thereby reducing luminous efficiency and service life.

Manufacture 3 of Organic Electroluminescence Device

An organic electroluminescence device of an embodiment including the polycyclic compound of an embodiment in the emission layer was manufactured as follows. Each of Example Compounds 1, 9, and 27 as described above were used as a host material of the emission layer to manufacture the organic electroluminescence devices of Examples 7, 8, and 9. Each of Comparative Example Compounds c1, c2, c3, and c4 as described above was used as a host material of the emission layer to manufacture the organic electroluminescence devices of Comparative Examples 9, 10, 11, and 12. A TADF material was used as a luminous material.

After ITO having a thickness of about 150 nm was patterned on a glass substrate, a first electrode was formed. An electrode substrate was washed with pure water and cleansed by ultrasonic waves for about 20 minutes, and then treated with ozone for about 10 minutes by irradiation with ultraviolet rays. After cleansing, the substrate was heated at 250° C., and then the substrate was introduced to a vacuum chamber to laminate organic materials as follows. N,N'-diphenyl-N, N'-bis(1-naphthyl)-1,10-biphenyl-4,4'-diamine (α-NPD) was deposited on the first electrode to form a hole injection layer having a thickness of about 30 nm, and then 4,4',4"-tris(N-carbazolyl)triphylamine (TCTA) was deposited thereon to form a hole transport layer having a thickness of about 20 nm. Then, 1,3-Bis(N-carbazolyl)benzene (mCP) was deposited thereon to form an electron blocking layer having a thickness of about 10 nm.

On the electron blocking layer, using each of Example Compounds or Comparative Example Compounds of the present disclosure as a host material, bis[4-(3,6-dimethoxy-carbazole)phenyl]sulfone (DMOC-DPS) was doped by 10% to form an emission layer having a thickness of about 20 nm. That is, the formed emission layer was deposited by doping DMOC-DPS to Compounds 1, 9, and 27 in Examples 7 to 9, respectively, and was deposited by doping DMOC-DPS to Compounds c1 to c4 in Comparative Examples 9 to 12, respectively.

On the emission layer, DPEPO was deposited to form a hole blocking layer having a thickness of about 10 nm, and then TPBi was deposited thereon to form an electron transport layer having a thickness of about 30 nm. Then, Liq was deposited thereon to form an electron injection layer having a thickness of about 2 nm. Then, Al was deposited thereon to form a second electrode having a thickness of about 120 nm to manufacture organic electroluminescence devices. The manufactured organic electroluminescence devices were sealed in a nitrogen atmosphere, and the evaluation was carried out in the atmosphere at room temperature.

TABLE 4

| Examples of manufactured devices | Host | Maximum luminous Efficiency | Luminance half-life |
|---|---|---|---|
| Example 7 | Example Compound 1 | 130% | 110% |
| Example 8 | Example Compound 9 | 130% | 120% |
| Example 9 | Example Compound 27 | 120% | 130% |
| Comparative Example 9 | Comparative Example Compound c1 | 100% | 100% |
| Comparative Example 10 | Comparative Example Compound c2 | 105% | 90% |
| Comparative Example 11 | Comparative Example Compound c3 | 80% | 60% |
| Comparative Example 12 | Comparative Example Compound c4 | 60% | 80% |

Referring to the results of Table 4, when the polycyclic compounds according to examples of the present disclosure each was used as a host material of the emission layer of each of the organic electroluminescence devices, high efficiency and a long service life may be achieved. Specifically, it can be seen that Examples 7, 8, and 9 exhibit high efficiency and long service life characteristics compared to Comparative Examples 9, 10, 11, and 12.

Manufacture 4 of Organic Electroluminescence Device

An organic electroluminescence device of an embodiment including the polycyclic compound of an embodiment in the electron transport region was manufactured as follows. Each of Example Compounds 1, 9, and 27 as described above was used as a material of the hole blocking layer in the electron transport region to manufacture each of the organic electroluminescence devices of Examples 10 to 12. In Comparative Examples 13 to 16, each of Comparative Example Compounds c1, c2, c3, and c4 was used as a material of the hole blocking layer to manufacture the organic electroluminescence devices. A TADF material was used as a luminous material.

From the formation of a first electrode to the formation of an electron blocking layer, the same processes as those described above (Manufacture 3 of Organic Electroluminescence Device) were carried out.

On the electron blocking layer, an emission layer having a thickness of about 20 nm, in which DMOC-DPS was doped by about 10%, was formed using DPEPO as a host material. Each of Example Compounds and Comparative Example Compounds was deposited on the emission layer to form a hole blocking layer having a thickness of about 10 nm. That is, with respect to the formed hole blocking layer, Compounds 1, 9, and 27 were deposited in Examples 10, 11, and 12, respectively, and Compounds c1, c2, c3, and c4 were deposited in Comparative Examples 13, 14, 15, and 16, respectively.

On each hole blocking layer, TPBi was deposited to form an electron transport layer having a thickness of about 30 nm, and Liq was deposited thereon to form an electron injection layer having a thickness of about 2 nm. Finally, Al was deposited thereon to form a second electrode having a thickness of about 120 nm to manufacture an organic electroluminescence device. The manufactured organic electroluminescence devices were sealed in a nitrogen atmosphere, and the evaluation was carried out in the atmosphere at room temperature.

TABLE 5

| Examples of manufactured devices | Hole blocking layer | Maximum luminous Efficiency | Luminance half-life |
|---|---|---|---|
| Example 10 | Example Compound 1 | 130% | 120% |
| Example 11 | Example Compound 9 | 130% | 130% |
| Example 12 | Example Compound 27 | 120% | 130% |
| Comparative Example 13 | Comparative Example Compound c1 | 100% | 100% |
| Comparative Example 14 | Comparative Example Compound c2 | 105% | 90% |
| Comparative Example 15 | Comparative Example Compound c3 | 80% | 60% |
| Comparative Example 16 | Comparative Example Compound c4 | 60% | 80% |

Referring to the results of Table 5, when the polycyclic compounds according to examples of the present disclosure each was used as a material of the electron transport region of each of the organic electroluminescence devices, high efficiency and a long service life may be achieved. Specifically, it can be seen that Examples 10, 11, and 12 exhibit high efficiency and long service life characteristics compared to Comparative Examples 13, 14, 15, and 16. The polycyclic compound of the present disclosure includes the polycyclic compound containing a benzimidazole group which is substituted at the ortho-position of the two aromatic 6-membered rings with respect to a single bond which links the two aromatic 6-membered rings, and thereby a twist may occur between the two aromatic 6-membered rings. Accordingly, the polycyclic compound of an embodiment may have a lowest triplet excitation energy level (T1 level) of about 2.8 eV or more (e.g., 2.8 eV to 3.5 eV) which is relatively high, and excellent electron transport characteristics.

The organic electroluminescence device of an embodiment of the present disclosure may have high efficiency along with long service life and low drive voltage characteristics due to including an embodiment of the polycyclic compound having a stable structure including the two aromatic 6-membered rings which are linked by a single bond.

The organic electroluminescence device according to an embodiment of the present disclosure may achieve high efficiency and long service life.

The polycyclic compound according to an embodiment of the present disclosure may be applied in the organic electroluminescence device to achieve high efficiency and long service life.

Although described with reference to example embodiments of the present disclosure, it will be understood that various changes and modifications of the subject matter of the present disclosure may be made by one skilled in the art or one having ordinary knowledge in the art without departing from the spirit and scope of the present disclosure as hereinafter claimed.

Hence, the technical scope of the present disclosure is not limited to the detailed descriptions in the specification, but it should be determined only by reference of the appended claims, and equivalents thereof.

What is claimed is:

1. An organic electroluminescence device comprising:
   a first electrode;
   a second electrode facing the first electrode; and
   a plurality of organic layers between the first electrode and the second electrode,
   wherein at least one organic layer of the plurality of organic layers comprises a polycyclic compound containing two aromatic 6-membered rings which are linked by a single bond, and each of the two aromatic 6-membered rings is substituted with one or more benzimidazole groups,
   wherein at least one of the two aromatic 6-membered rings is substituted with at least two benzimidazole groups,
   wherein the benzimidazole groups are bonded to the two aromatic 6-membered rings through the nitrogen atom of the benzimidazole groups,
   wherein each of the two aromatic 6-membered rings comprises a carbon atom or a nitrogen atom as an atom for forming a ring, and
   wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, Zn, a compound of two or more thereof, a mixture of two or more thereof, and oxides thereof.

2. The organic electroluminescence device of claim 1, wherein at least one of the plurality of benzimidazole groups is substituted at an ortho-position of any one between the two aromatic 6-membered rings with respect to the single bond.

3. The organic electroluminescence device of claim 1, wherein a number of the plurality of benzimidazole groups is 3 to 4.

4. The organic electroluminescence device of claim 1, wherein each of the plurality of benzimidazole groups is substituted at a ortho-position or a meta-position of a respective one of the two aromatic 6-membered rings with respect to the single bond.

5. The organic electroluminescence device of claim 1, wherein a lowest triplet excitation energy level ($T_1$ level) of the polycyclic compound is 2.8 eV or more.

6. The organic electroluminescence device of claim 1, wherein the plurality of organic layers comprise a hole transport region, an emission layer, and an electron transport region, wherein the emission layer comprises the polycyclic compound.

7. The organic electroluminescence device of claim 6, wherein the emission layer has phosphorescence luminescence or thermally activated delayed fluorescence luminescence characteristics.

8. The organic electroluminescence device of claim 6, wherein a maximum luminous wavelength of the emission layer is 440 nm to 500 nm.

9. The organic electroluminescence device of claim 1, wherein the plurality of organic layers comprise a hole transport region, an emission layer, and an electron transport region, wherein the electron transport region comprises the polycyclic compound.

10. An organic electroluminescence device comprising:
a first electrode;
a second electrode facing the first electrode; and
a plurality of organic layers between the first electrode and the second electrode,
wherein at least one organic layer of the plurality of organic layers comprises a polycyclic compound represented by Formula 1 below:

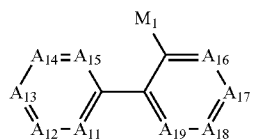

[Formula 1]

wherein, in Formula 1 above,
$A_{11}$ to $A_{19}$ are each independently N or CR,
R is a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 6 to 30 carbon atoms for forming a ring, or $M_2$, or is combined with an adjacent group to form a ring,
at least two selected from among $A_{11}$ to $A_{15}$ are $CM_2$, and
$M_1$ and $M_2$ are each independently represented by Formula 2 below:

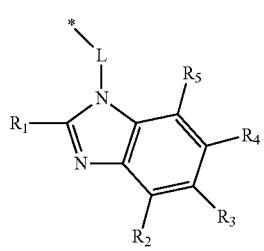

[Formula 2]

wherein, in Formula 2 above,
$R_1$ to $R_5$ are each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or are combined with an adjacent group to form a ring, and L is a direct linkage, a substituted or unsubstituted arylene group having 6 to 30 carbon atoms, or a substituted or unsubstituted heteroarylene group having 2 to 30 carbon atoms, wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, Zn, a compound of two or more thereof, a mixture of two or more thereof, and oxides thereof.

11. The organic electroluminescence device of claim 10, wherein the polycyclic compound represented by Formula 1 is represented by any one selected from Formula 1-1 to Formula 1-7 below:

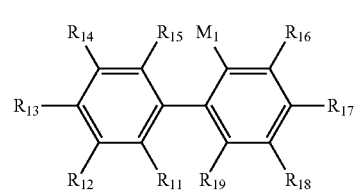

[Formula 1-1]

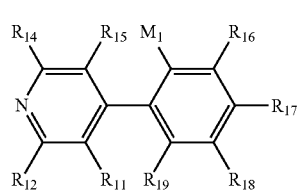

[Formula 1-2]

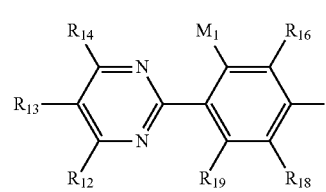

[Formula 1-3]

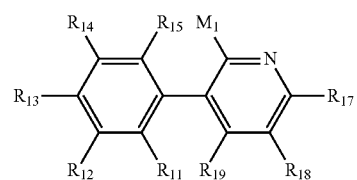

[Formula 1-4]

[Formula 1-5]

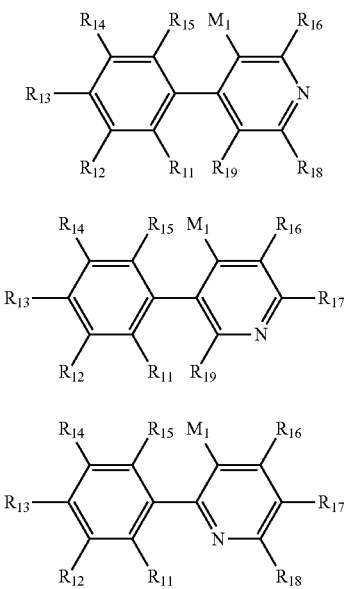

[Formula 1-6]

[Formula 1-7]

wherein, in Formula 1-1 to Formula 1-7, $R_{11}$ to $R_{19}$ are each independently a hydrogen atom, or represented by Formula 2, at least two selected from among $R_{11}$ to $R_{15}$ are represented by Formula 2, and $M_1$ is the same as that defined with respect to Formula 1.

12. The organic electroluminescence device of claim 10, wherein a substituent represented by the Formula 2 above is represented by any one selected from among Formula 2-1 to Formula 2-4 below:

[Formula 2-1]

[Formula 2-2]

[Formula 2-3]

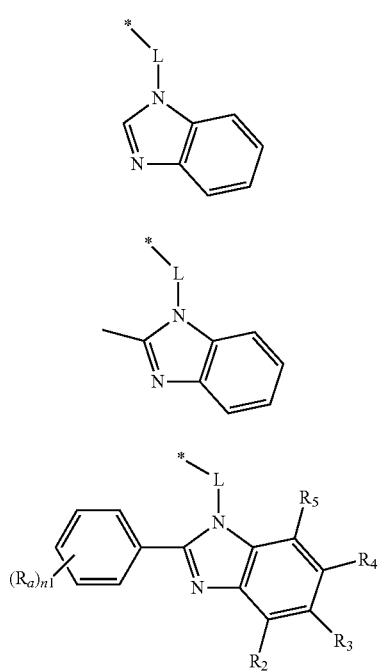

[Formula 2-4]

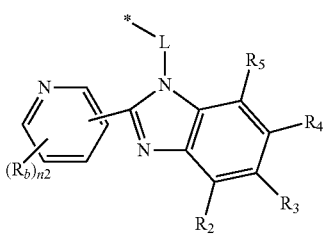

wherein, in Formula 2-1 to Formula 2-4, $R_a$ to $R_b$ are each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or are combined with an adjacent group to form a ring, $n_1$ and $n_2$ are each independently an integer of 0 to 4, and $R_2$ to $R_5$ and L are the same as those defined with respect to Formula 2.

13. The organic electroluminescence device of claim 10, wherein two to three selected from among $A_{11}$ to $A_{19}$ are $CM_2$.

14. The organic electroluminescence device of claim 10, wherein a lowest triplet excitation energy level ($T_1$ level) of the polycyclic compound is 2.8 eV or more.

15. The organic electroluminescence device of claim 10, wherein the polycyclic compound represented by Formula 1 above is any one selected from among compounds represented by Compound Group 1 below:

[Compound Group 1]

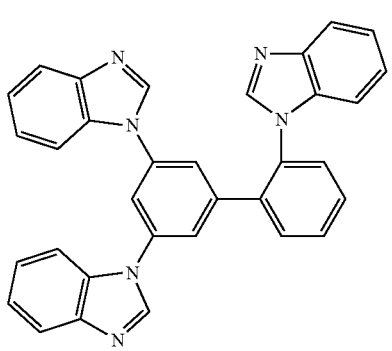

1

2
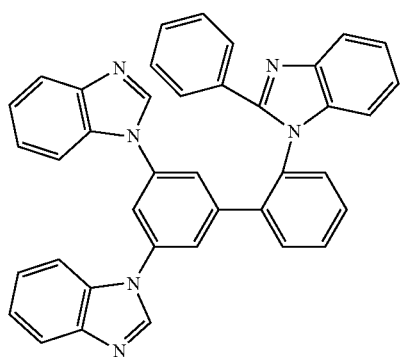
3
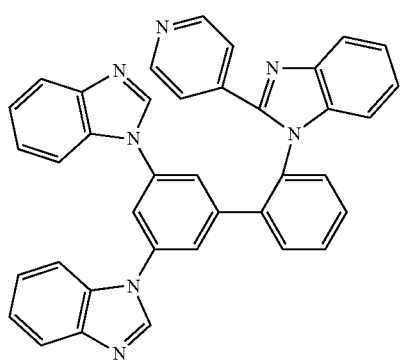
4
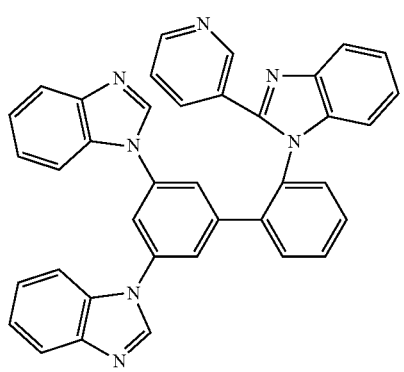
5
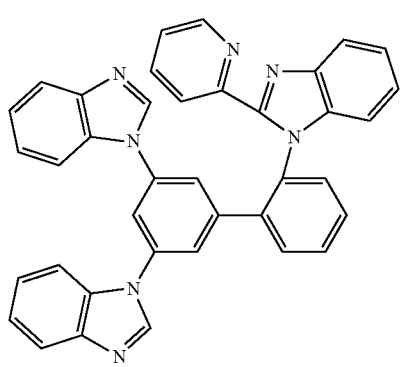
6
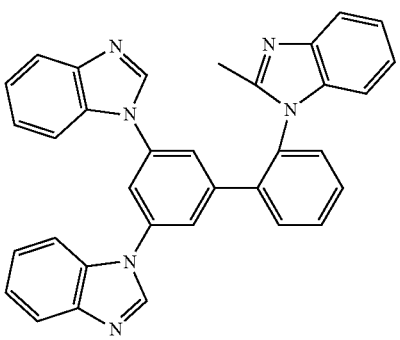
7
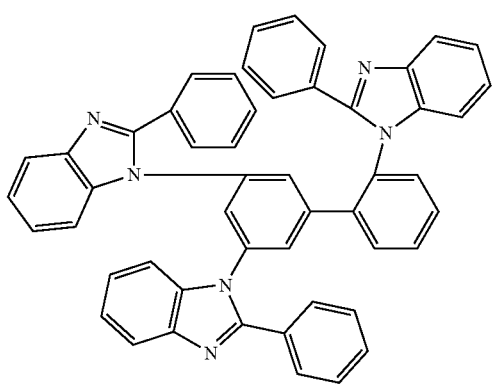
8
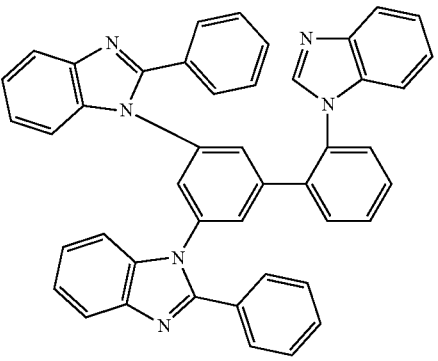
9
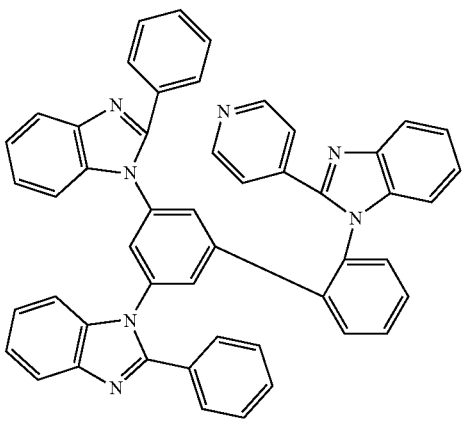

10
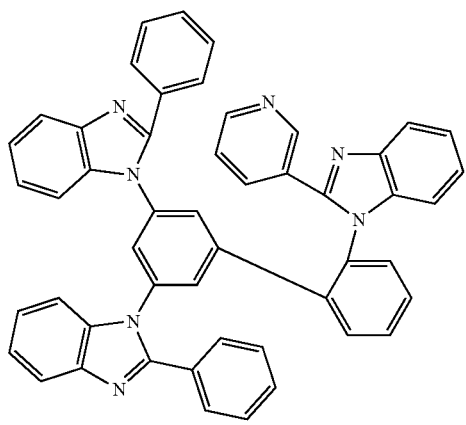
11
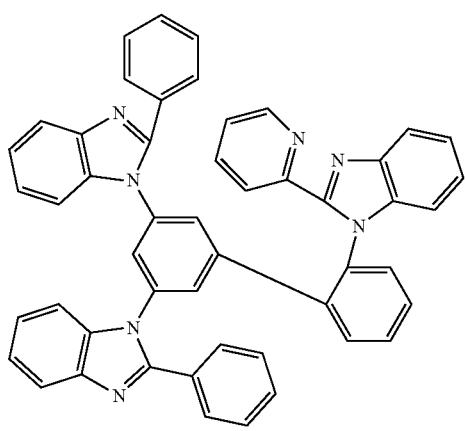
12
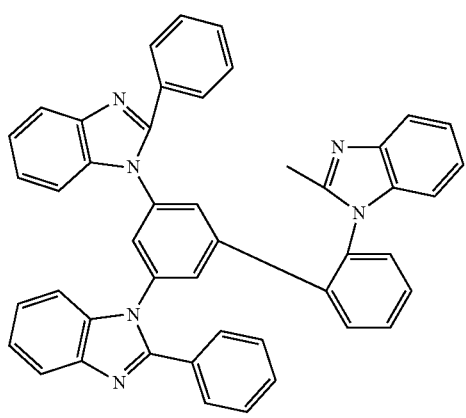
13
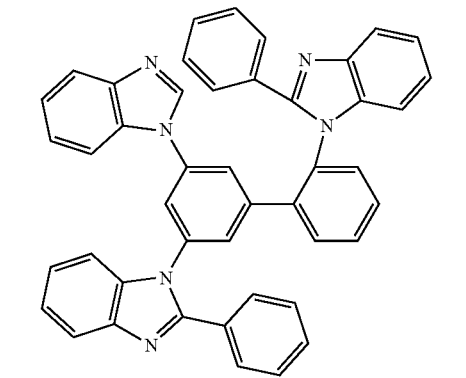
14
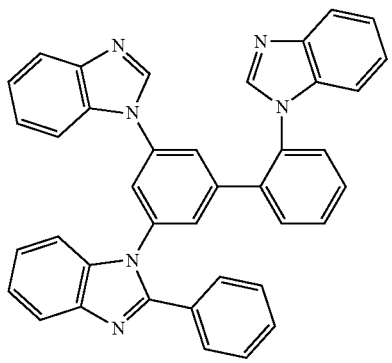
15
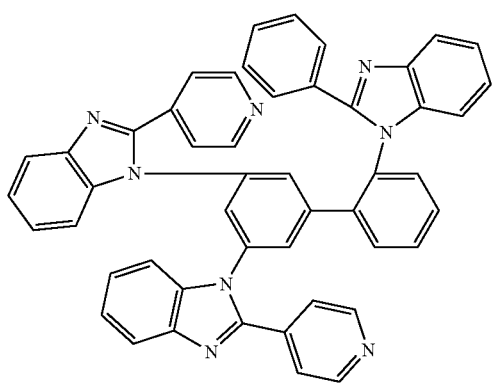
16
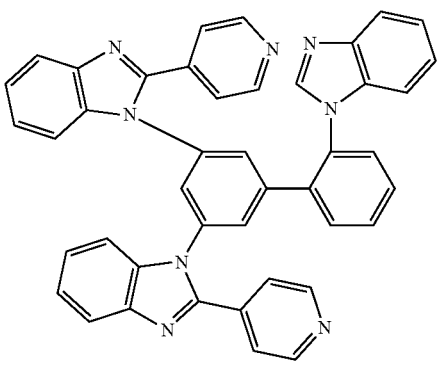
17
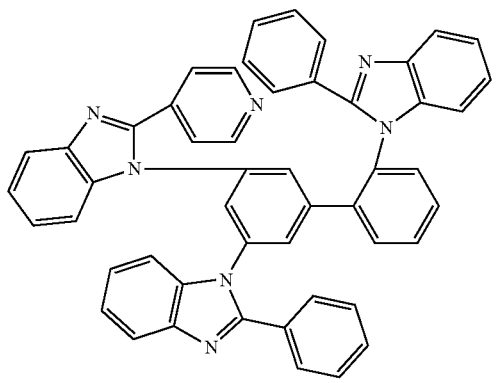

18
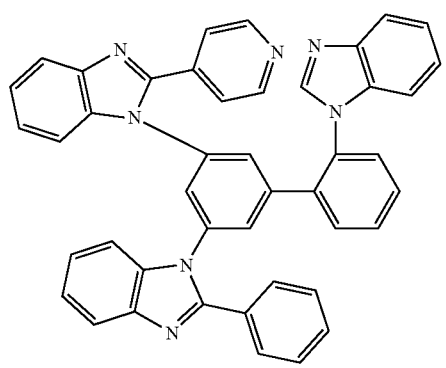
19
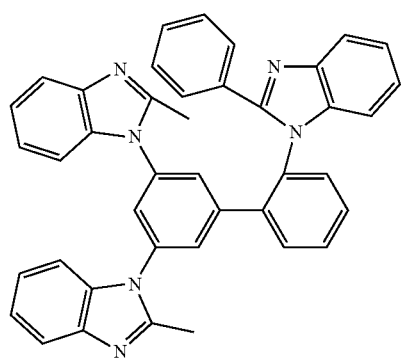
28
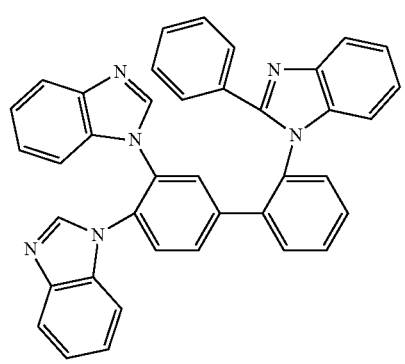
29
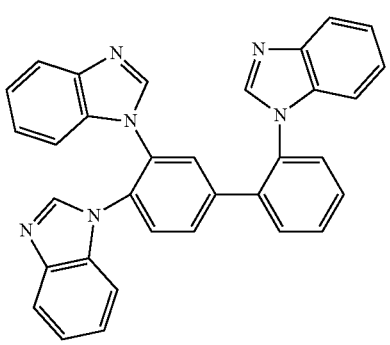
30
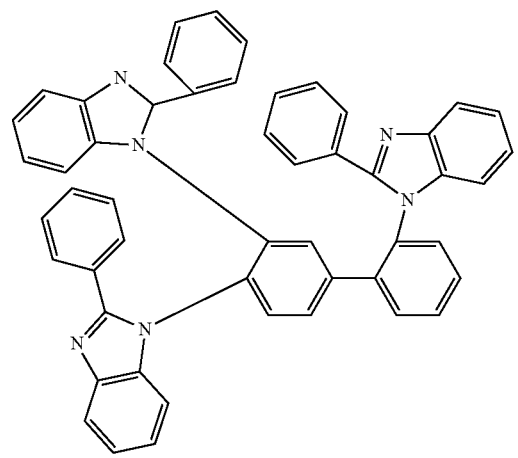
31
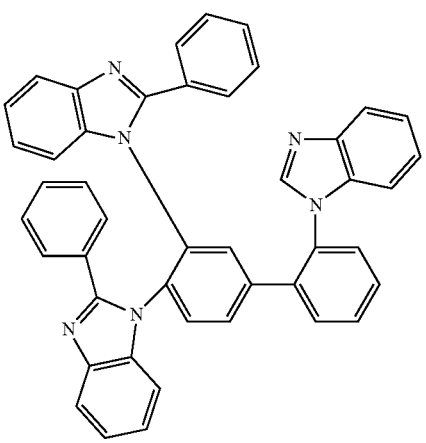
32
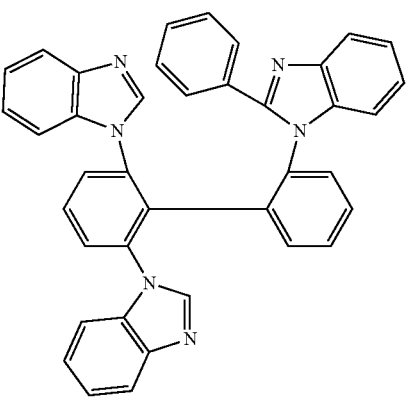
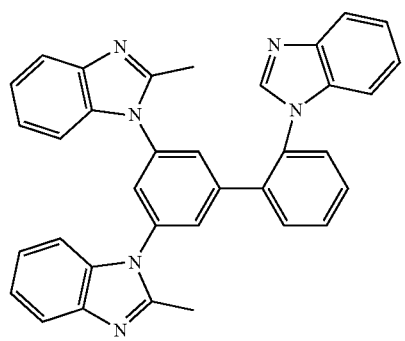

33
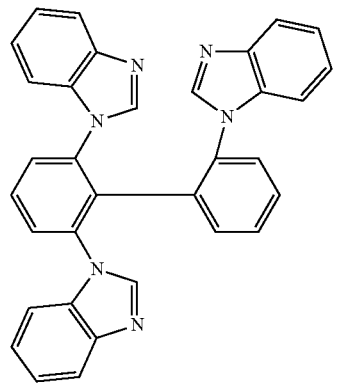
34
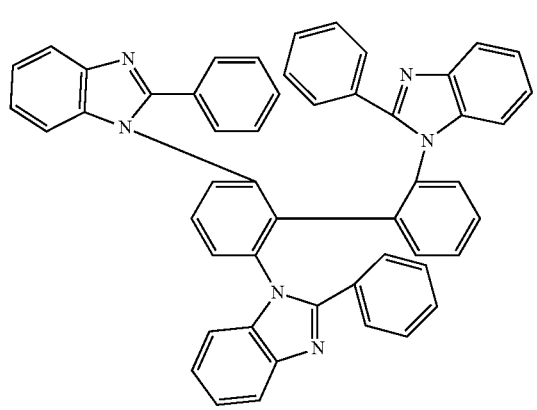
35
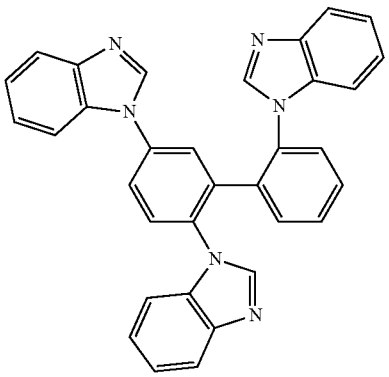
37
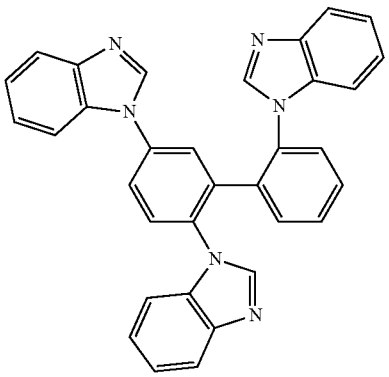
38
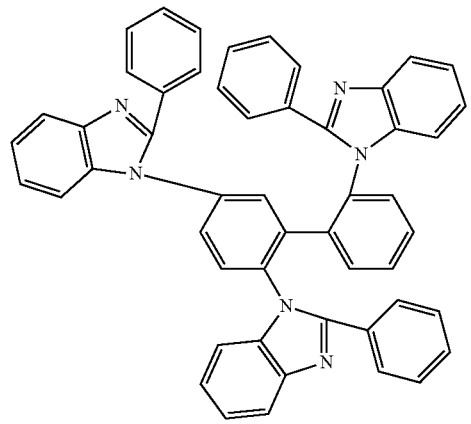
39
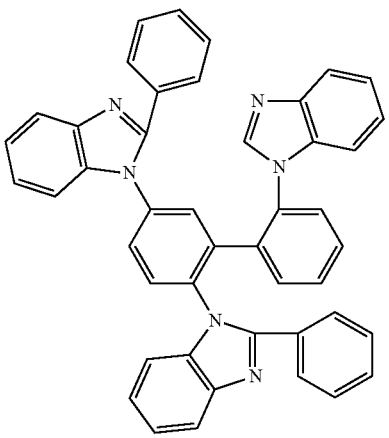
40
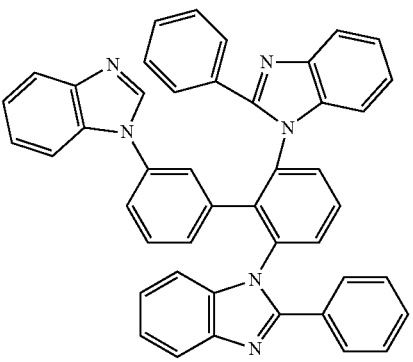

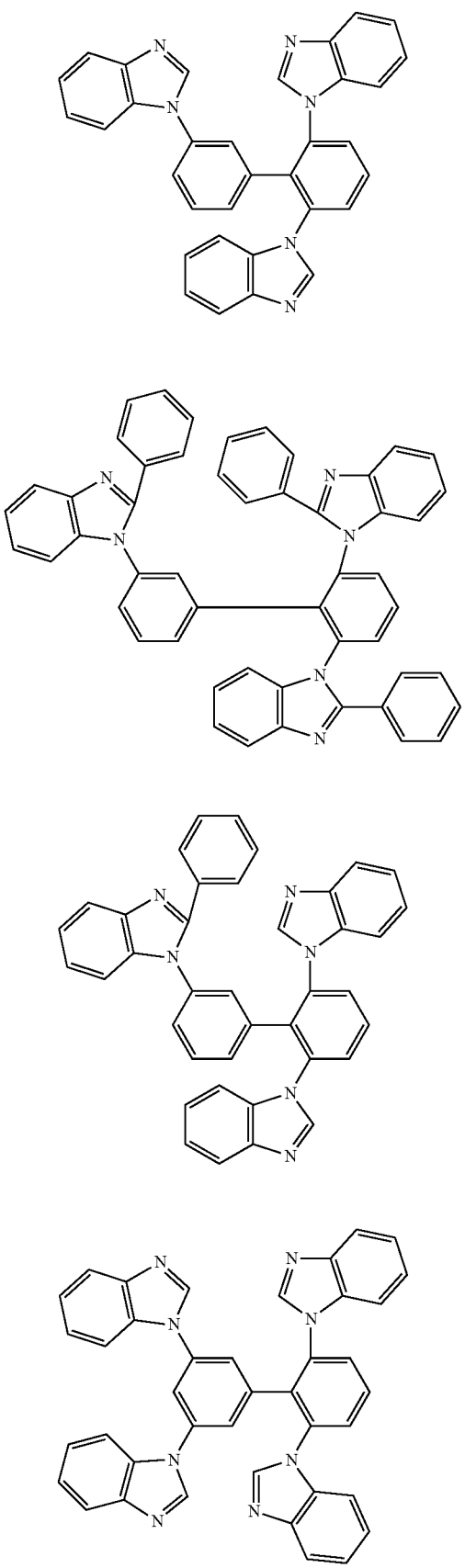
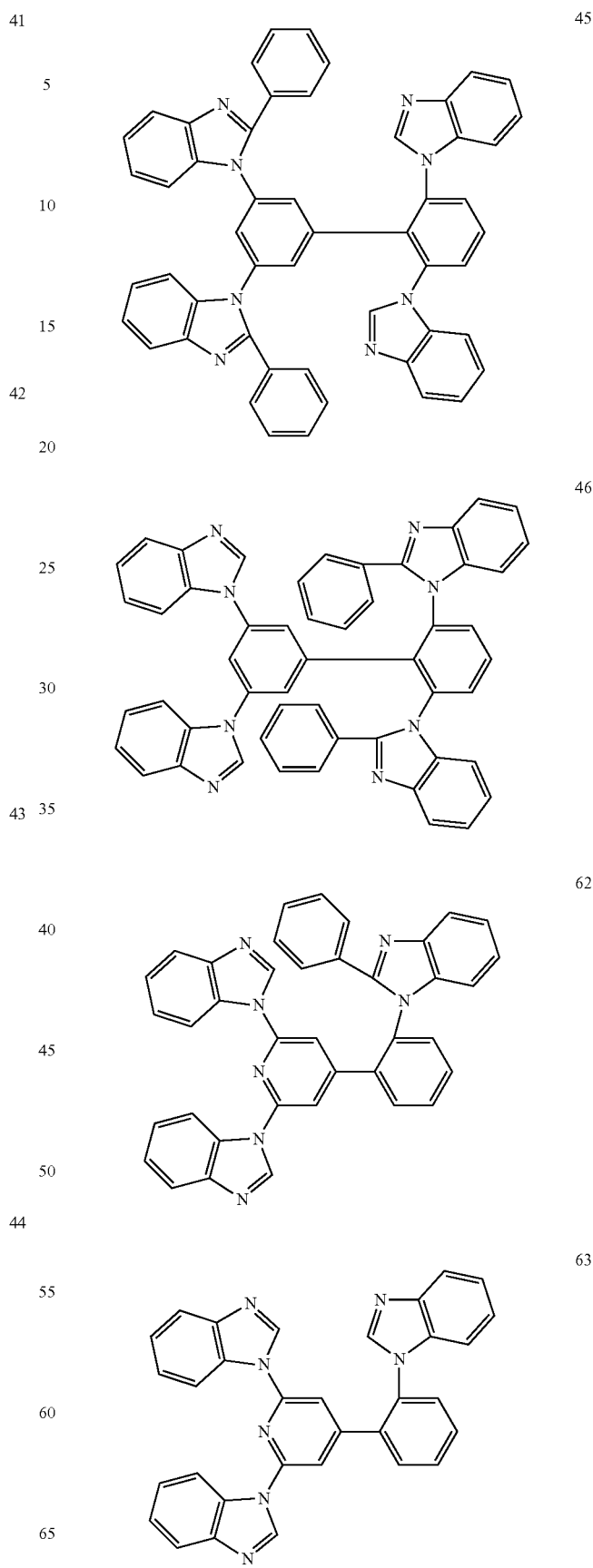

-continued
64
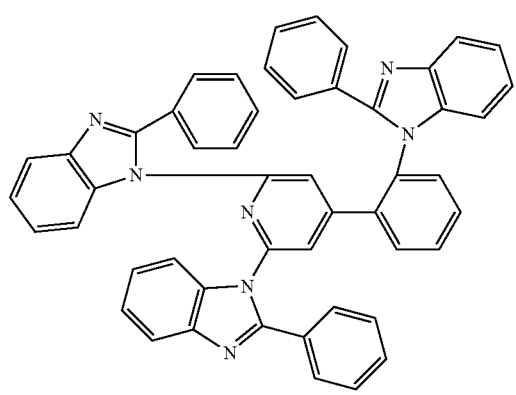
65
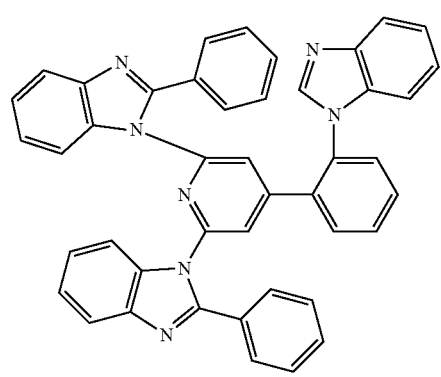
66
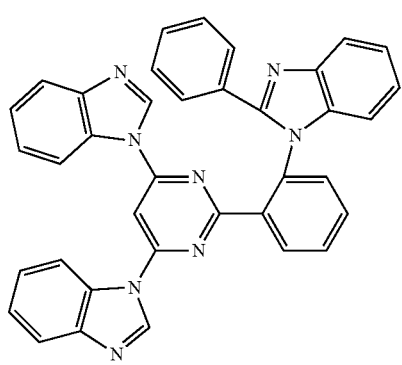
67
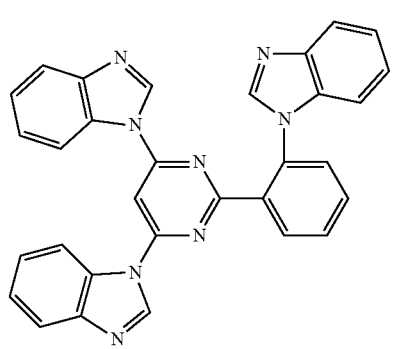
-continued
68
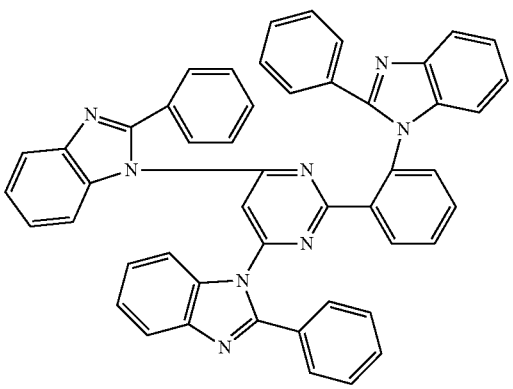
69
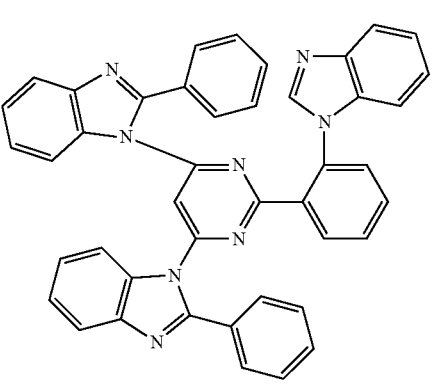
70
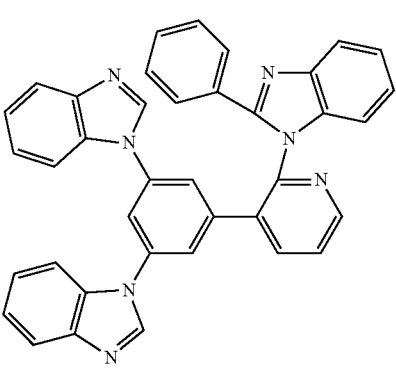
71
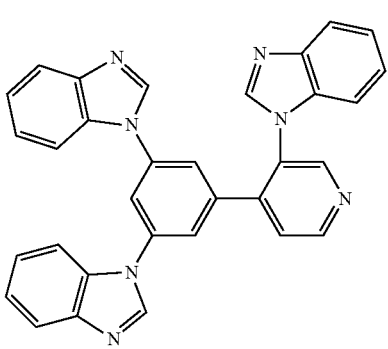

72
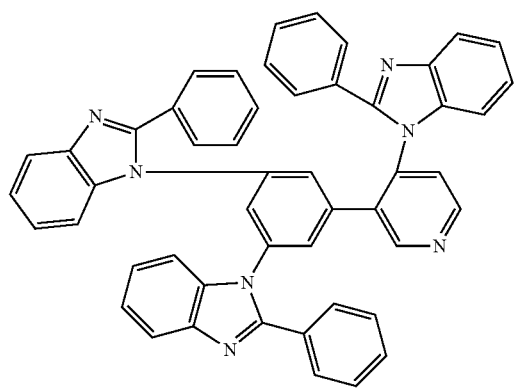
73
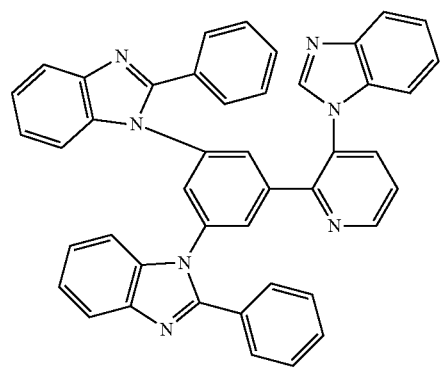
74
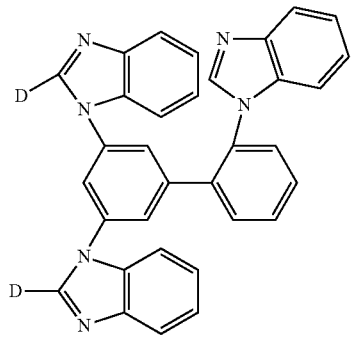
76
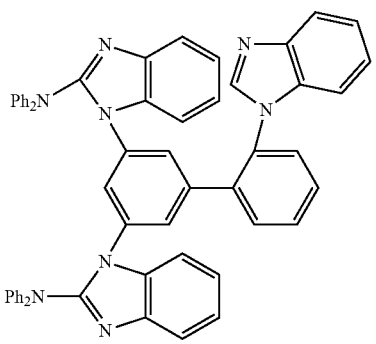
77
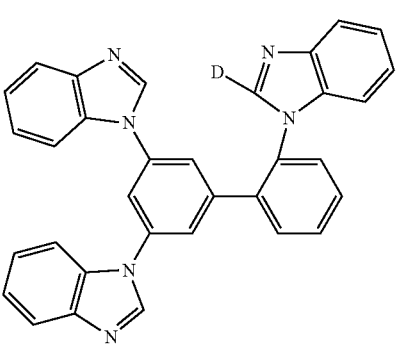
78
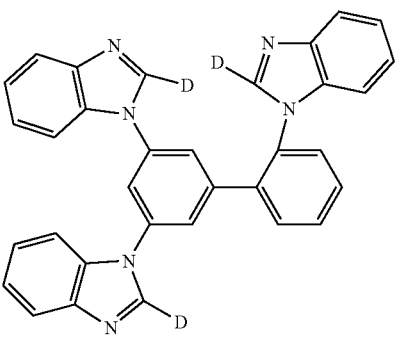
79
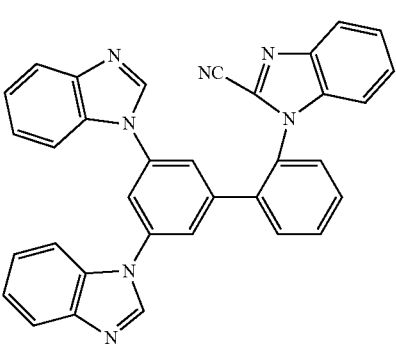
75

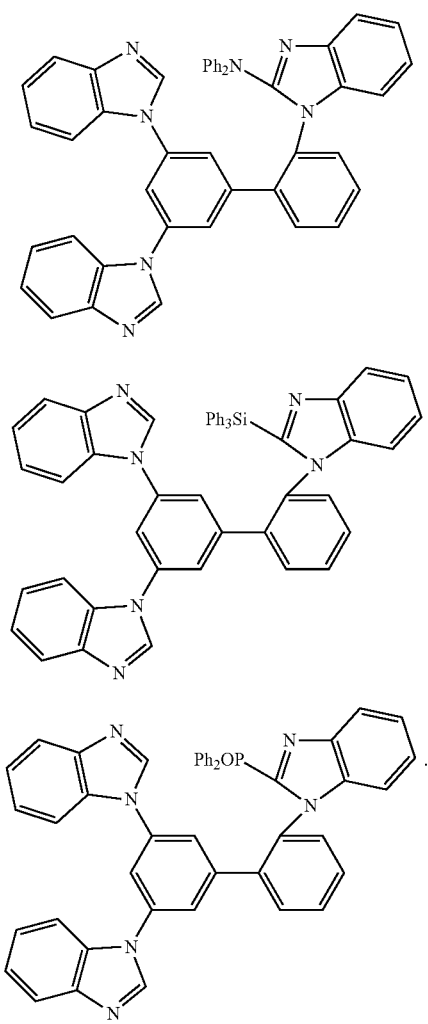

16. A polycyclic compound represented by Formula 1 below:

[Formula 1]

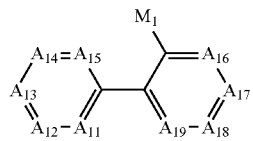

wherein, in Formula 1 above, $A_{11}$ to $A_{19}$ are each independently N or CR, R is a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 6 to 30 carbon atoms for forming a ring, or $M_2$, or is combined with an adjacent group to form a ring, $M_1$ and $M_2$ are each independently represented by Formula 2 below, at least two selected from among $A_{11}$ to $A_{15}$ are $CM_2$, and

[Formula 2]

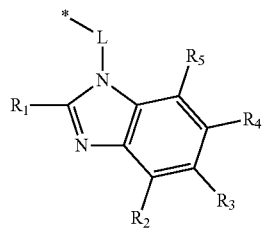

wherein, in Formula 2 above, $R_1$ to $R_5$ are each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or are combined with an adjacent group to form a ring, and L is a direct linkage, a substituted or unsubstituted arylene group having 6 to 30 carbon atoms, or a substituted or unsubstituted heteroarylene group having 2 to 30 carbon atoms.

17. The polycyclic compound of claim 16, wherein the polycyclic compound represented by Formula 1 above is represented by any one selected from Formula 1-1 to Formula 1-7 below:

[Formula 1-1]

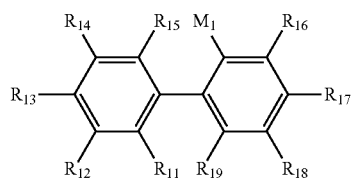

[Formula 1-2]

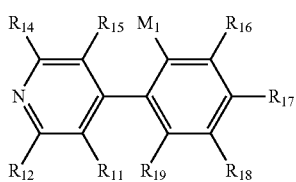

-continued

[Formula 1-3]
[Formula 1-4]
[Formula 1-5]
[Formula 1-6]
[Formula 1-7]

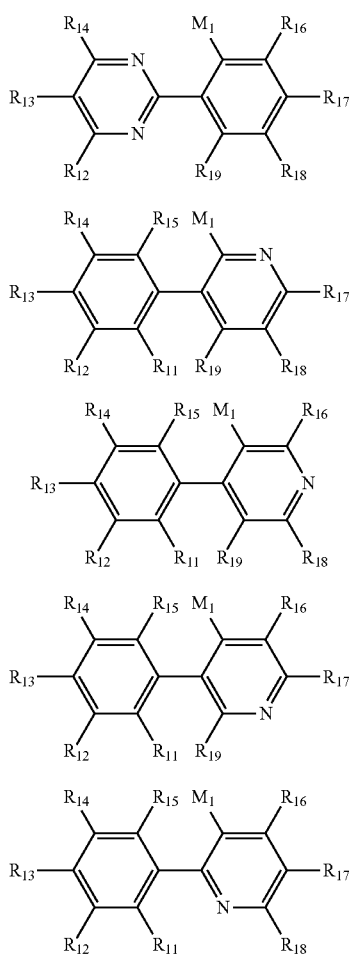

in Formula 1-1 to Formula 1-7,
$R_{11}$ to $R_{19}$ are each independently a hydrogen atom, or represented by Formula 2,
at least two selected from among $R_{11}$ to $R_{15}$ are represented by Formula 2, and
$M_1$ is the same as that defined with respect to Formula 1.

18. The polycyclic compound of claim 16, wherein a substituent represented by the Formula 2 above is represented by any one selected from Formula 2-1 to Formula 2-4 below:

[Formula 2-1]

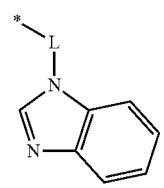

[Formula 2-2]

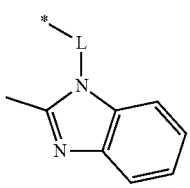

-continued

[Formula 2-3]

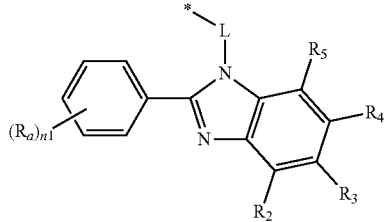

[Formula 2-4]

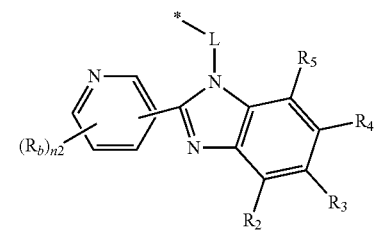

wherein, in Formula 2-1 to Formula 2-4,
$R_a$ to $R_b$ are each independently a hydrogen atom, a deuterium atom, a halogen atom, a cyano group, a substituted or unsubstituted amine group, a substituted or unsubstituted silyl group, a substituted or unsubstituted oxy group, a substituted or unsubstituted thio group, a substituted or unsubstituted sulfinyl group, a substituted or unsubstituted sulfonyl group, a substituted or unsubstituted carbonyl group, a substituted or unsubstituted boron group, a substituted or unsubstituted phosphine oxide group, a substituted or unsubstituted sulfide group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or are combined with an adjacent group to form a ring,
$n_1$ and $n_2$ are each independently an integer of 0 to 4, and
$R_2$ to $R_5$ and L are the same as those defined with respect to Formula 2.

19. The polycyclic compound of claim 16, wherein a lowest triplet excitation energy level (T1 level) of the polycyclic compound is 2.8 eV or more.

20. The polycyclic compound of claim 14, wherein the polycyclic compound represented by Formula 1 above is any one selected from among compounds represented by Compound Group 1 below:

1

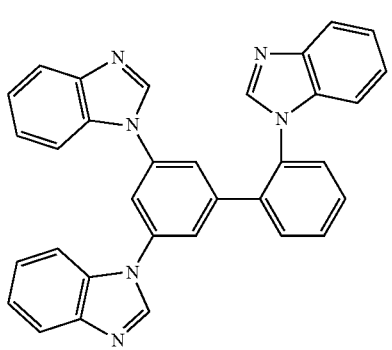

101
-continued
2
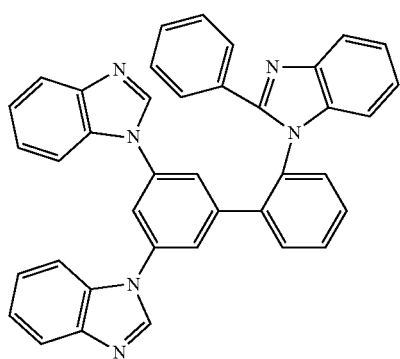
3
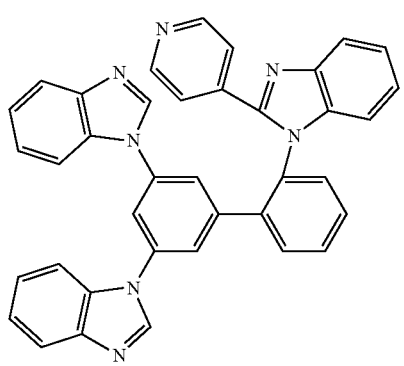
4
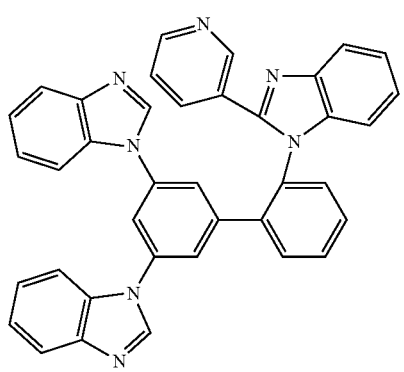
5
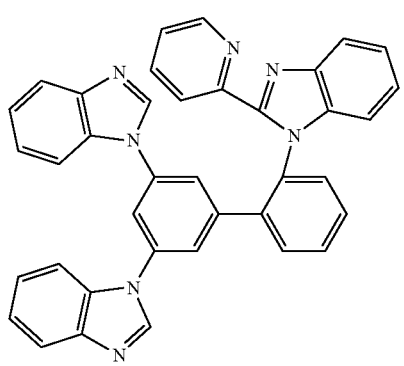
102
-continued
6
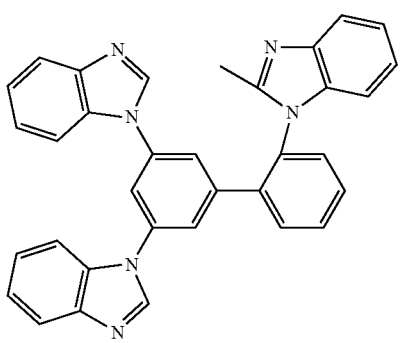
7
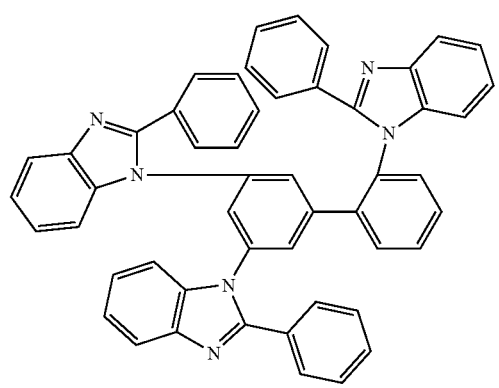
8
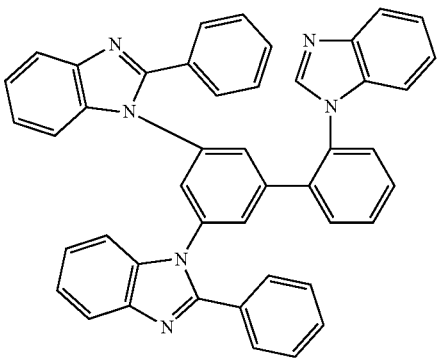
9
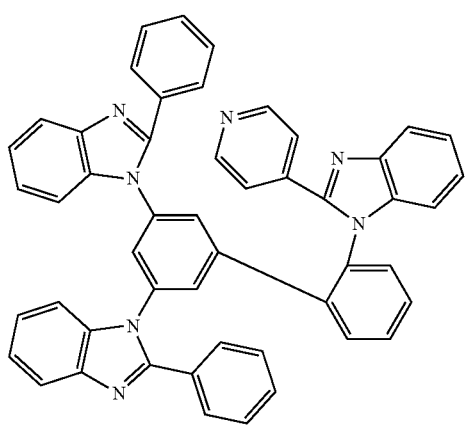

10
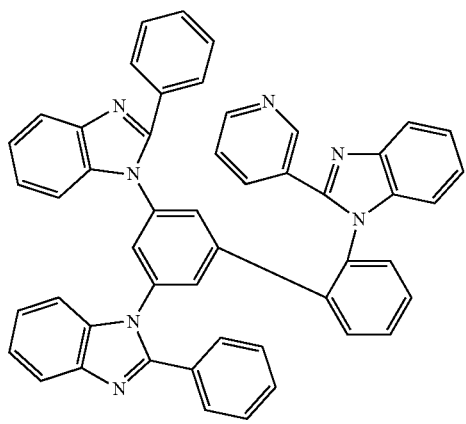
11
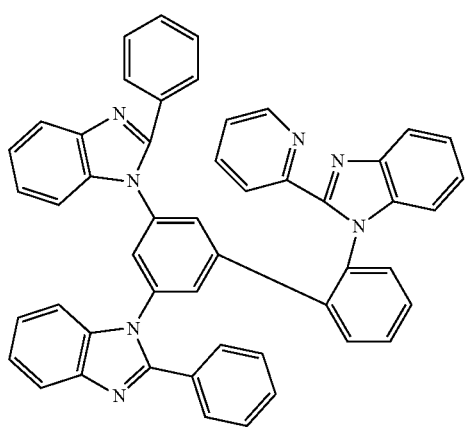
12
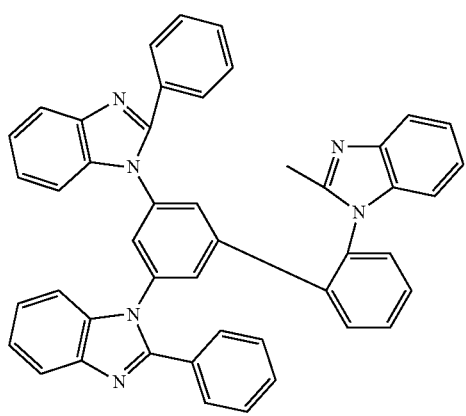
13
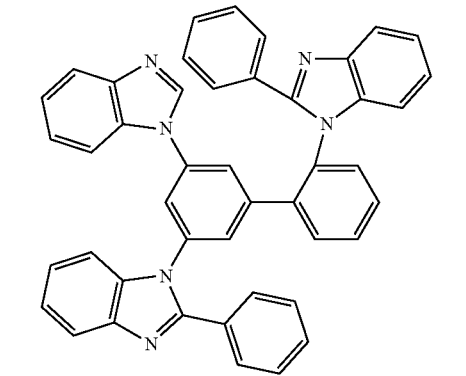
14
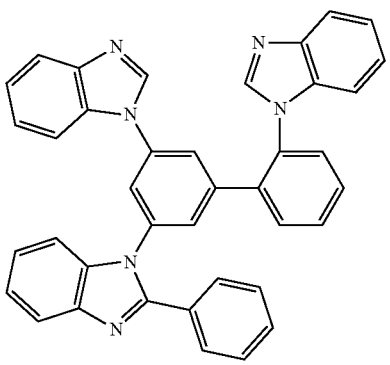
15
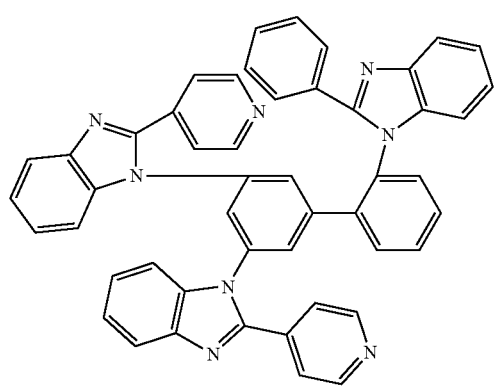
16
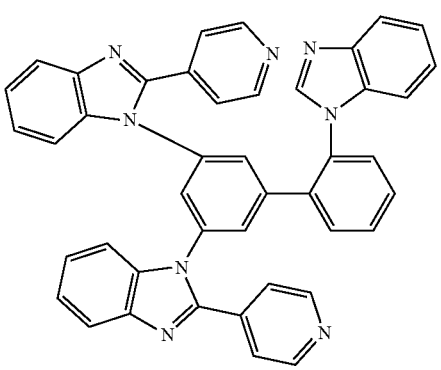
17
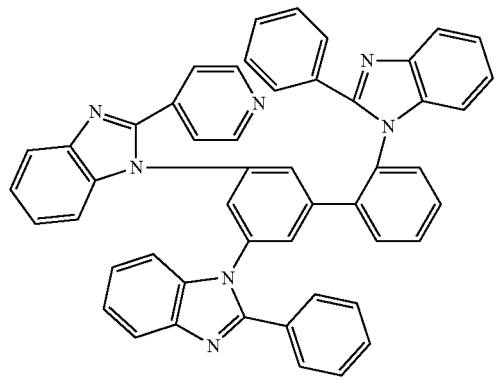

18
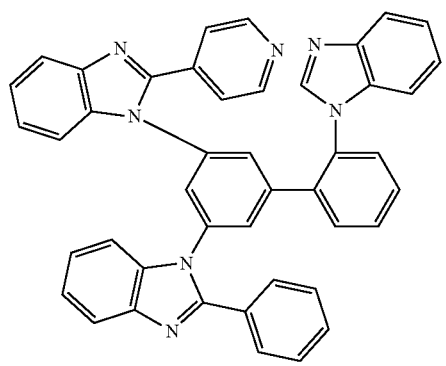
19
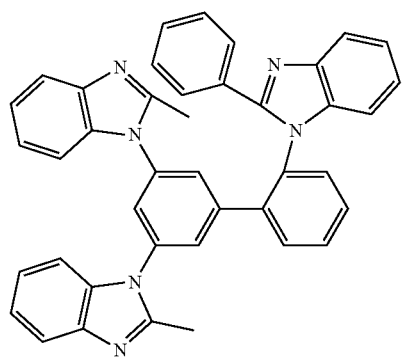
20
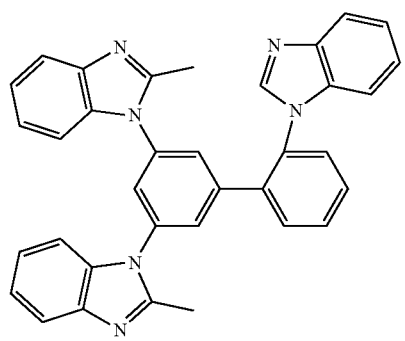
28
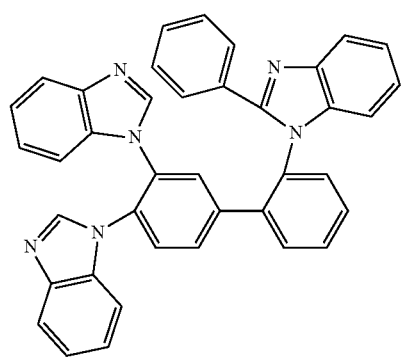
29
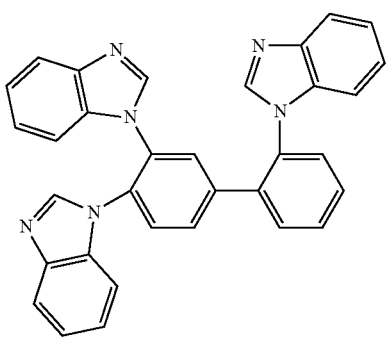
30
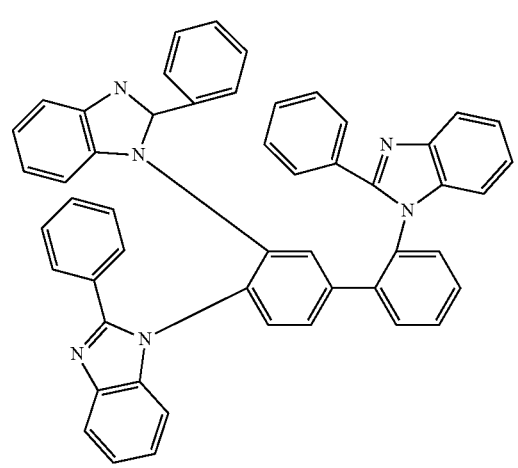
31
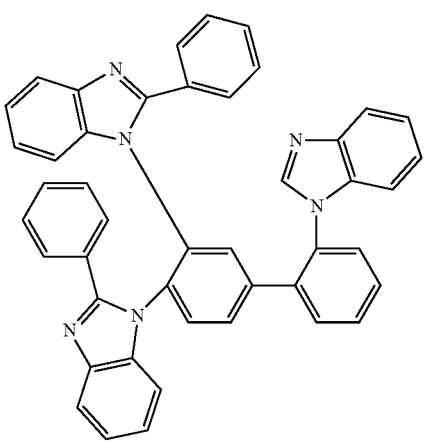
32
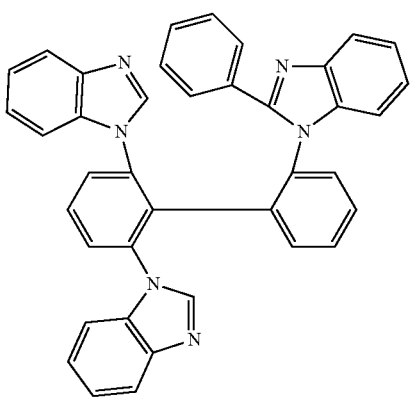

33
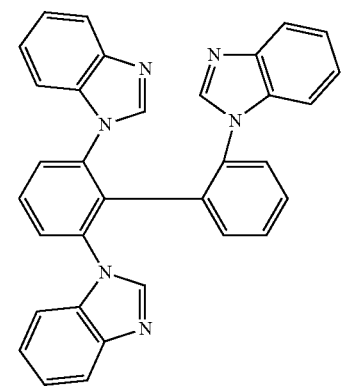
34
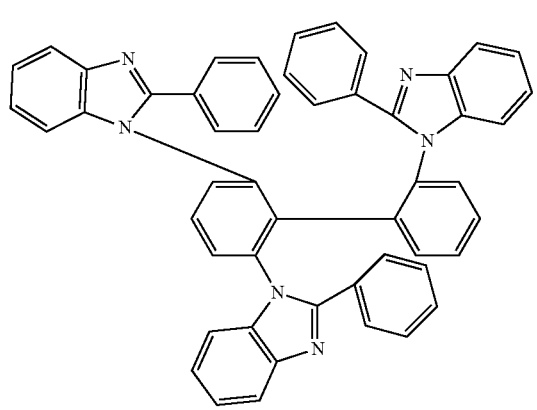
35
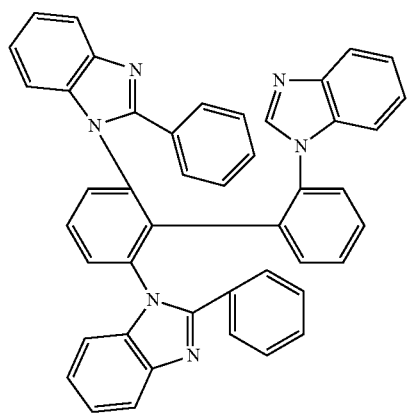
36
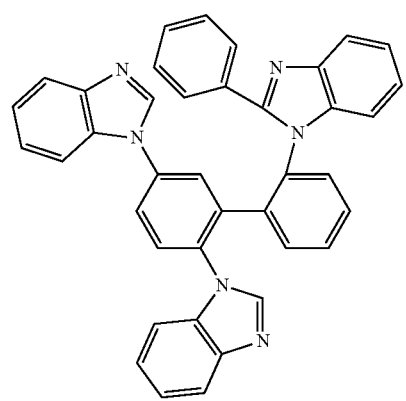
37
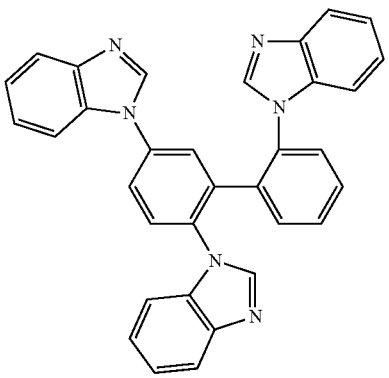
38
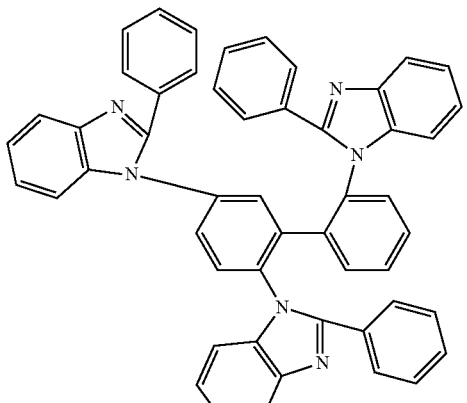
39
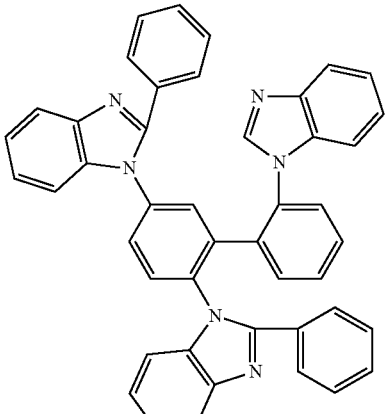
40
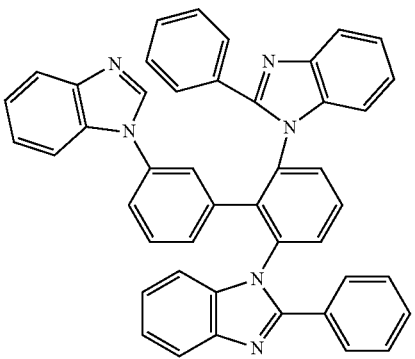

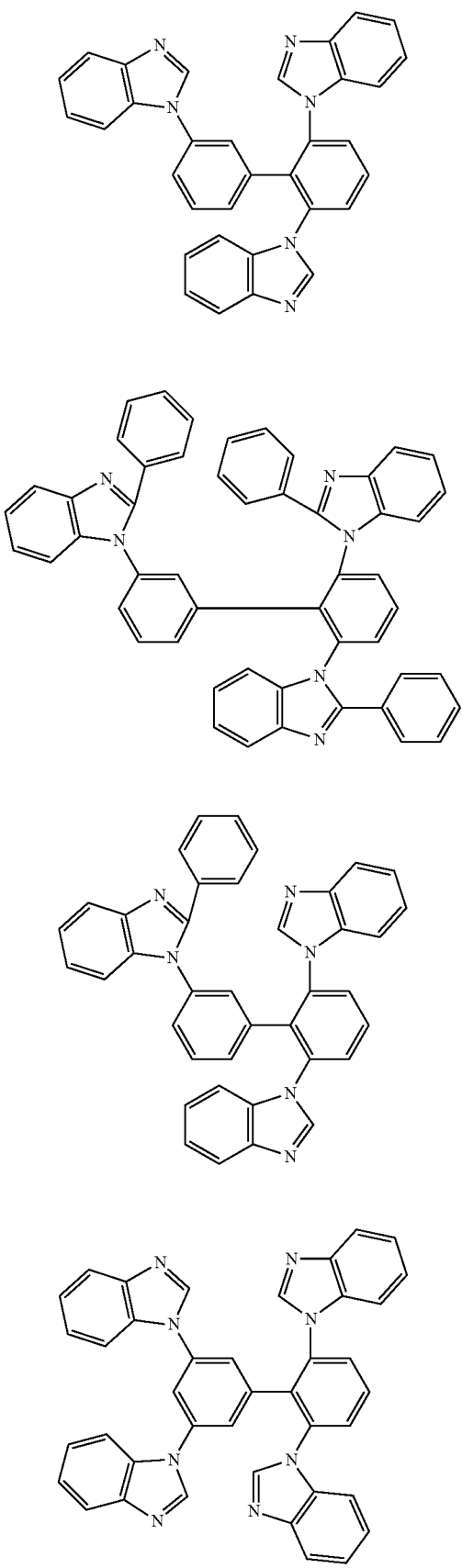
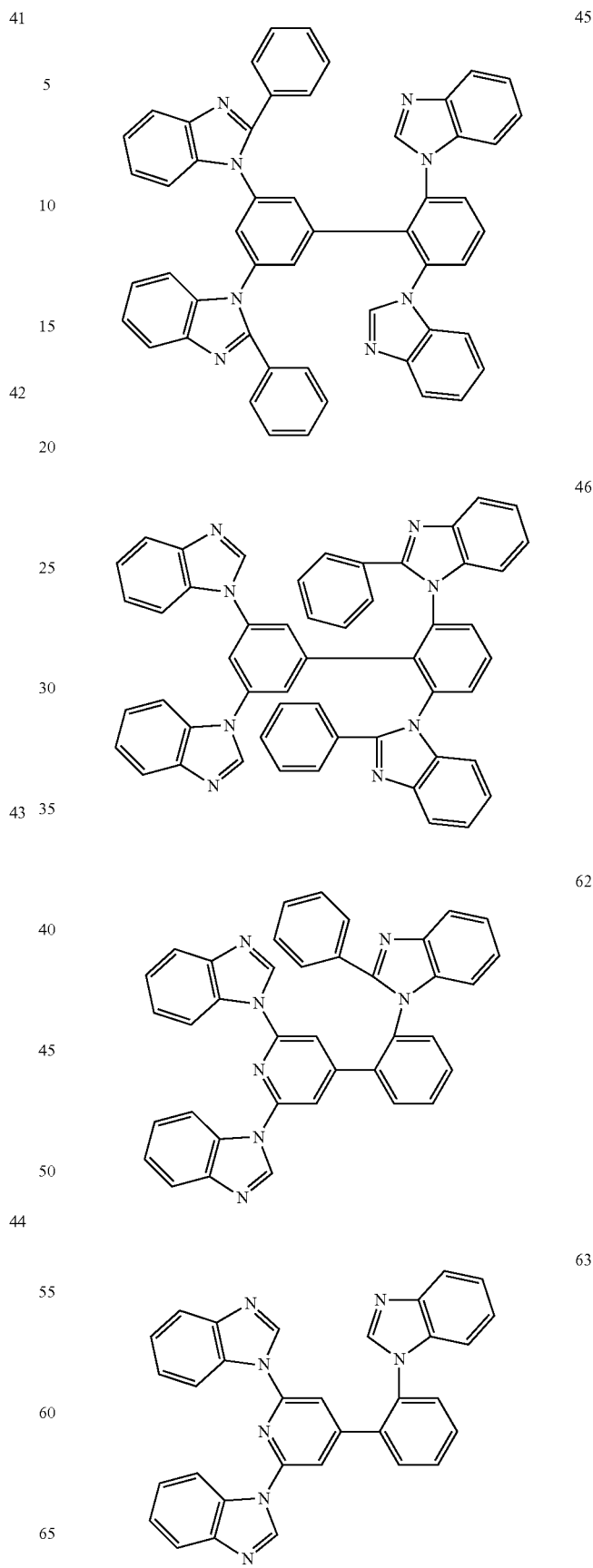

64
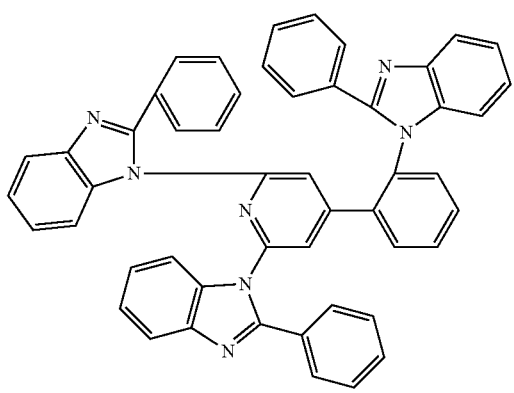
65
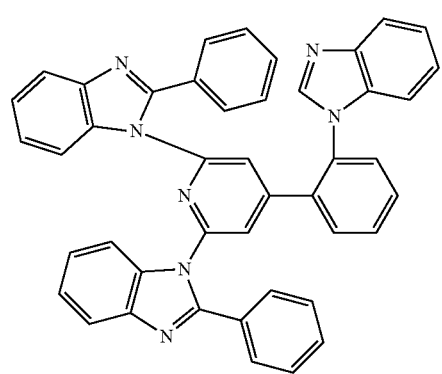
66
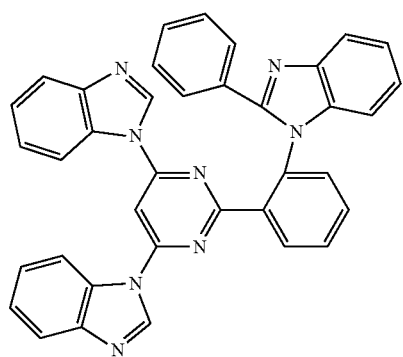
67
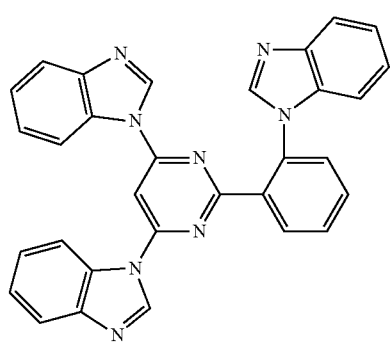
68
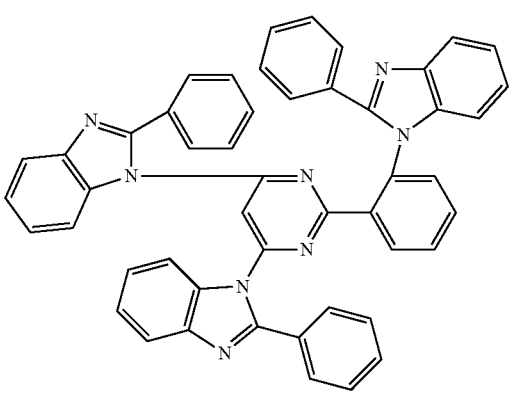
69
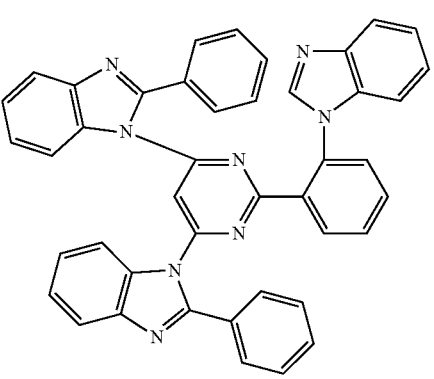
70
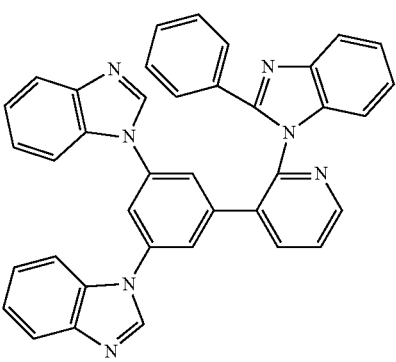
71
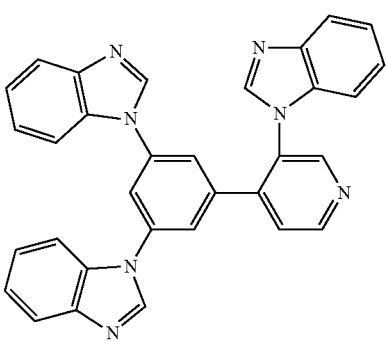

72
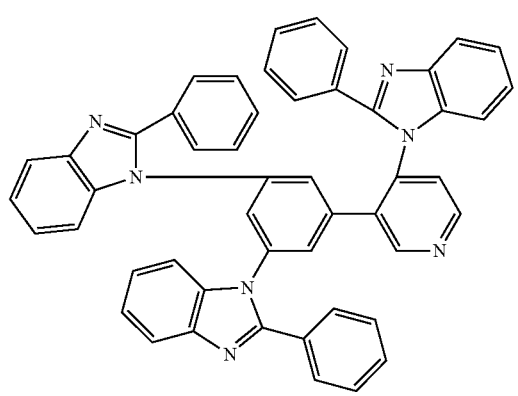
73
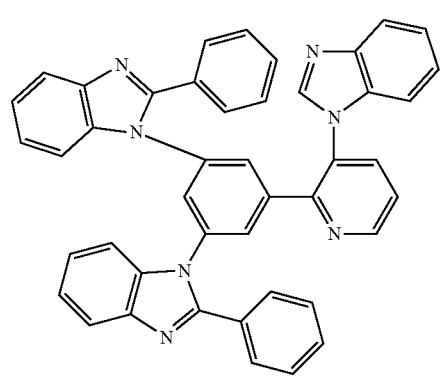
74
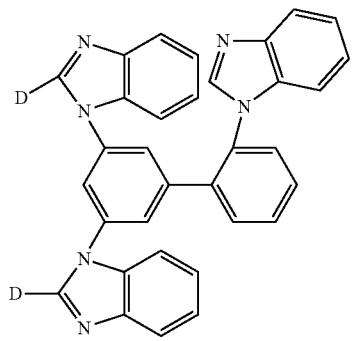
75
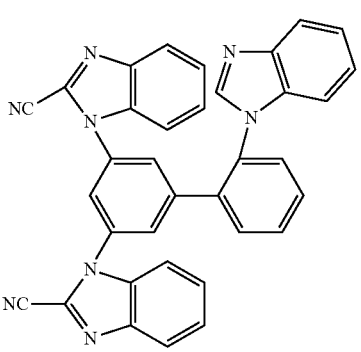
76
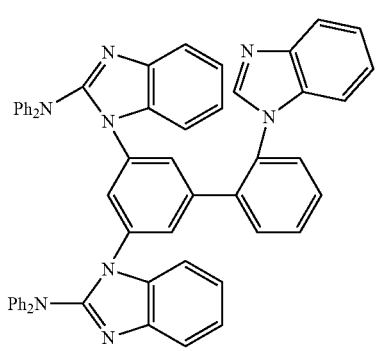
77
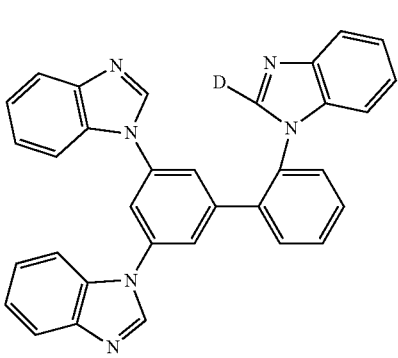
78
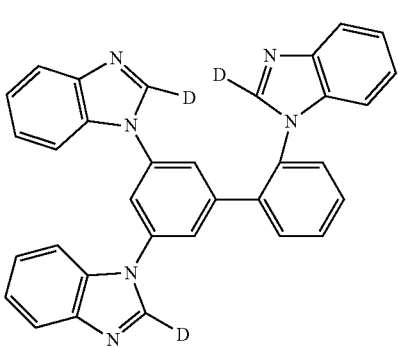

79
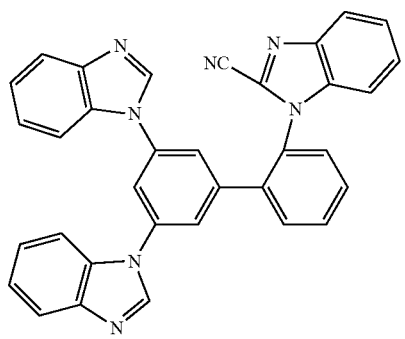
80
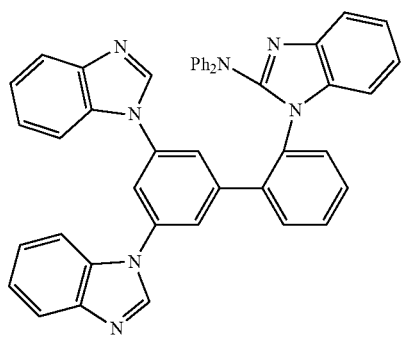
81
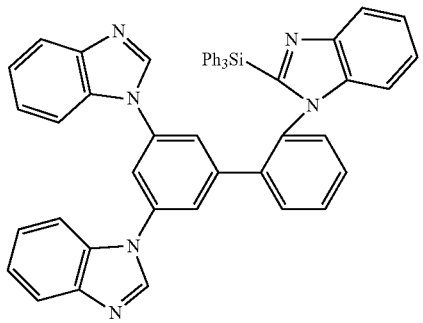
82
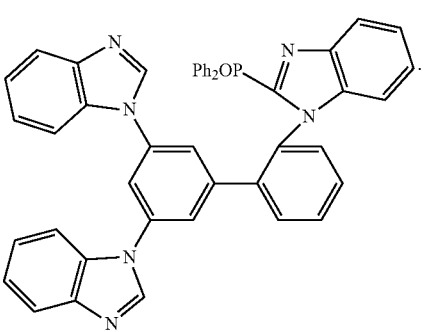
* * * * *

UNITED STATES PATENT AND TRADEMARK OFFICE
CERTIFICATE OF CORRECTION

PATENT NO. : 12,052,915 B2
APPLICATION NO. : 16/931273
DATED : July 30, 2024
INVENTOR(S) : Akinori Yamatani et al.

Page 1 of 3

It is certified that error appears in the above-identified patent and that said Letters Patent is hereby corrected as shown below:

In the Claims

In Column 88, Lines 16-34, in Claim 15, in Compound 30, delete " 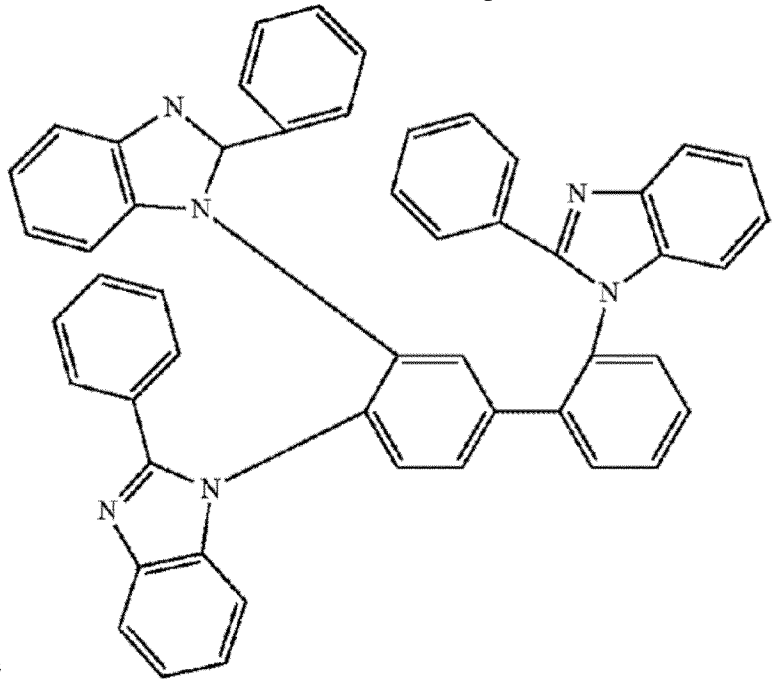 " and insert Signed and Sealed this
Thirty-first Day of December, 2024

Derrick Brent
*Acting Director of the United States Patent and Trademark Office*

CERTIFICATE OF CORRECTION (continued)
U.S. Pat. No. 12,052,915 B2

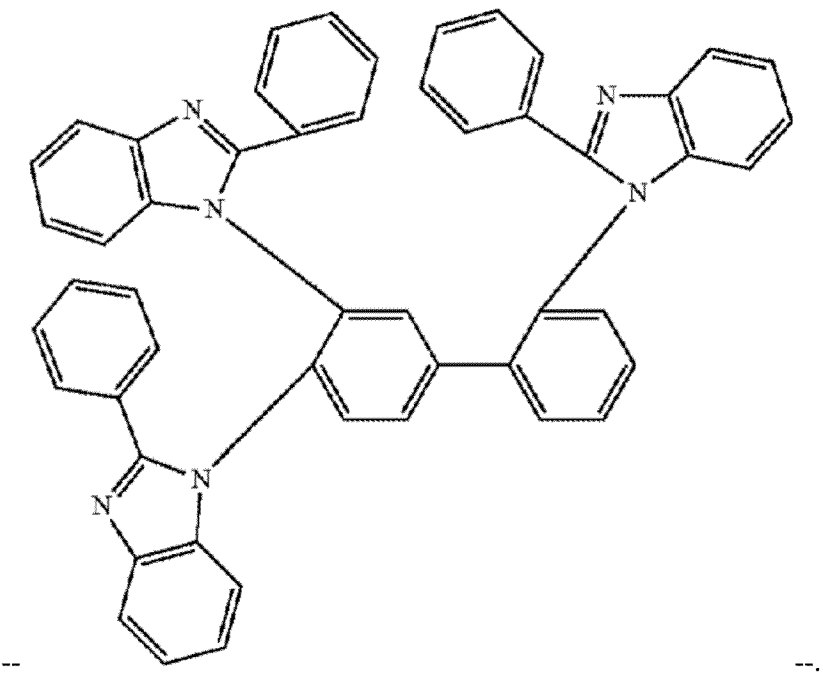

-- --.

In Column 106, Lines 16-34, in Claim 20, in Compound 30,

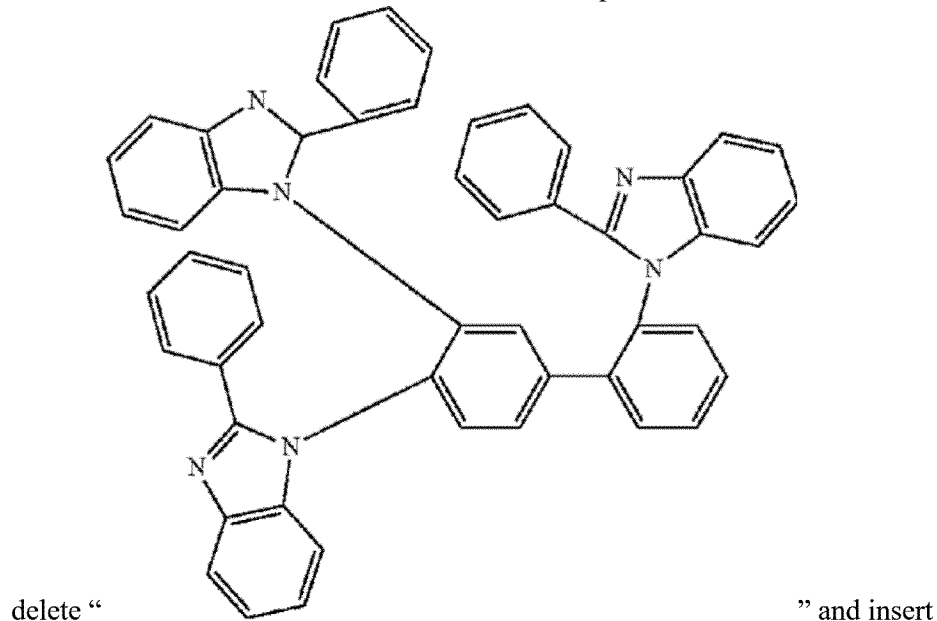

delete " " and insert

CERTIFICATE OF CORRECTION (continued)
U.S. Pat. No. 12,052,915 B2

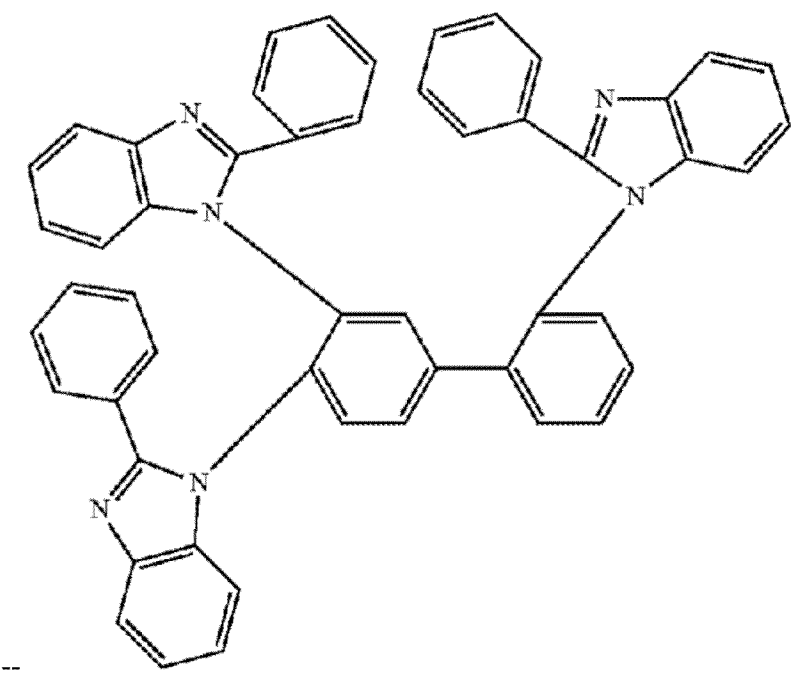

-- -.